United States Patent [19]
Copeland et al.

[11] Patent Number: 6,103,473
[45] Date of Patent: Aug. 15, 2000

[54] MUTAGENICITY SCREENING METHOD USING HUMAN DNA POLYMERASE OR CATALYTIC POLYPEPTIDE

[75] Inventors: William C. Copeland, Durham, N.C.; Teresa S. -F. Wang, Palo Alto, Calif.

[73] Assignee: Board of Trustees of the Leland Stanford Jr. University, Stanford, Calif.

[21] Appl. No.: 09/156,842

[22] Filed: Sep. 18, 1998

Related U.S. Application Data

[62] Division of application No. 07/792,600, Nov. 15, 1991, Pat. No. 6,008,045.

[51] Int. Cl.⁷ .............................. C12Q 1/68; C12Q 1/48; C12P 19/34
[52] U.S. Cl. .............................. 435/6; 435/15; 435/91.1; 435/91.2
[58] Field of Search .............................. 435/6, 15, 91.1, 435/91.2

[56] References Cited

U.S. PATENT DOCUMENTS

| | | | |
|---|---|---|---|
| 4,745,051 | 5/1988 | Smith et al. | 435/68 |
| 4,879,236 | 11/1989 | Smith et al. | 435/235 |
| 4,916,122 | 4/1990 | Chu et al. | 514/50 |

OTHER PUBLICATIONS

Stillman, Ann. Rev. Cell Biol. 5:197 (1989).
Challberg and Kelly, Ann. Rev. Biochem. 58:671 (1989).
Tsurimoto et al., Nature 346:534 (1990).
Wang, Ann. Rev. Biochem. 60:513 (1991).
Wong et al., J. Biol. Chem. 261:7958 (1986).
Maniatis, et al., in: *Molecular Cloning, A Laboratory Manual*, pp. 224–246, (Cold Spring Harbor Laboratory, NY 1982).
Bollum, J. Biol. Chem. 235:2399 (1960).
Mechali et al., J. Biol. Chem. 255:2114 (1980).
Kaguni et al., Proc. Natl. Acad. Sci. USA 80:2221 (1983).
Chang et al., J. Biol. Chem. 259:14679 (1984).
Plevani et al., J. Biol. Chem. 260:7102 (1985).
Grosse and Krauss, J. Biol. Chem. 260:1881 (1985).
Wang et al., J. Biol. Chem. 259:1854 (1984).
Lehman and Kaguni, J. Biol. Chem. 264:4265 (1989).
Tanaka et al., J. Biol. Chem. 257:8386 (1982).
Wong et al., The EMBO Journal 7:37 (1988).
Lathe, J. Mol. Biol. 183:1 (1985).
Okayama and Berg, Mol. Cell. Biol. 2:161 (1982).
Proudfoot and Brownlee, Nature 263:211 (1976).
Cleary et al., Cell 47:19 (1986).
Dale et al., Plasmid 13:31 (1985).
Vialard et al., J. Virology 64:37 (1990).
Tabor and Richardson, Proc. Natl. Acad. Sci. USA 82:1074 (1985).
Summers and Smith, Bulletin No. 1555, Texas Agriculture Experimentation Station (College Station, TX) (1988).
Hsi et al., Nucleic Acids Res. 18:6231 (1990).
Fisher and Korn, J. Biol. Chem. 252:6528 (1977).
Brooke et al., J. Biol. Chem. 266:3005 (1991).
Kornberg, *DNA Replication*, p. 121 and p. 329 (Freeman and Co.) (1980).
Syvaoja and Linn, J. Biol. Chem. 264:2489 (1989).
Kunkel et al., Mol. Cell. Biol. 9:4447 (1989).
Dornreiter et al., EMBO J. 9:3329 (1990).
De Jong et al., J. Mag. Res. 80:197 (1988).
Lanford, Virol. 167:72 (1988).
Okayama and Berg, Mol. Cell. Biol. 3:280 (1983).
Yang et al., Nature 353:628 (1991).
Hunkapiller et al., Methods in Enzymol. 91:399 (1983).
Luckow, in: *Recombinant DNA Technology and Applications*, pp. 97–152, (Prokop, Bajpai, and Ho, Eds.) (McGraw–Hill, Inc., New York, NY, 1991).
Wang et al., Federation Amer. Soc. Exper. Biol. J. 3:14–21 (1989).
Robins, Chem. & Eng., Jan. 27, 1986, pp. 28–40.
Copeland et al., in: Eukaryotic DNA Replication. Cold Spring Harbor Laboratory, p. 156 (1991).
Copeland and Wang, J. Biol. Chem. 266:22739 (1991).

*Primary Examiner*—Kenneth R. Horlick
*Attorney, Agent, or Firm*—Medlen & Carroll, LLP

[57] ABSTRACT

The human DNA polymerase α catalytic polypeptide has been functionally over-expressed by a recombinant baculovirus in insect cells at >1000 fold higher levels than that found in cultured normal human cells.

4 Claims, 24 Drawing Sheets

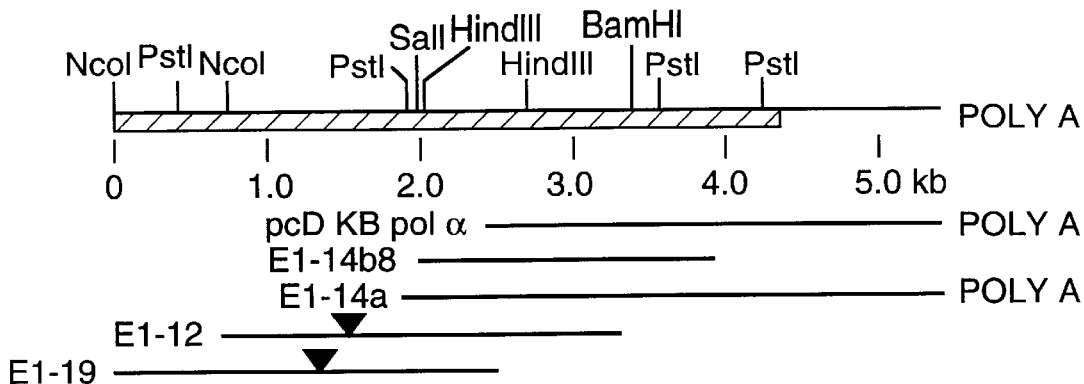

SUMMATION OF MUTATIONS IN POLYMERASE α cDNA CLONES:

E1-19 FRAMESHIFT MUTATION:

NUCLEOTIDE
POSITION 1336:  EI-12: 5'-G AAC TAT GCT TTT GAG ATA CCT G-3'
  E1-19: 5'-G AAC TAT GCT TT G AGA TAC CTG -3'
  BC2#: 5'-G AAC TAT GCA TT C GAG ATA CCT G-3'

E1-12 FRAMESHIFT MUTATION:

NUCLEOTIDE
POSITION 1519-1538:
 EMBO paper: 5'-GTA AAA AA G TCC ACA GCT CTT AAT CAG-3'
    V   K   K   S   T   A   L   N   Q
 E1-12: 5'-GTA AAA AA G TCC ACA GCT CTT GAA TCA GCC AGT
    V   K   K   S   T   A   L   E   S   A   S
 E1-19: 5'-GTA AAA A GT CCA CAG CTC TTG AAT CAG -3'
    V   K   S   P   Q   L   L   N   Q E1-14b8 MISSENCE MUTATION:

NULCEOTIDE
POSITION 2526:  E1-14b8: GGA (Gly)
  E1-14a: GCA (Ala)

FROM FIG. 3A →

TO FIG. 3C →

```
CTACTTAGGAAGTTTCTCCCGGATGTCTCTTGTTGGGACACATTGATCAAGAAGGTGATAG  960
  Y  L  G  S  F  L  P  D  V  S  C  W  D  I  D  Q  E  G  D  S  - 315
CAGTTTCTCAGTGCAAGAAGTTCAAGTGGATTCCAGTCCACCTCCCATTGGTAAAGGGGC   1020
  S  F  S  V  Q  E  V  Q  V  D  S  S  H  L  P  L  V  K  G  A  - 335
AGATGAGGAACAAGTATTCCACTTTTATTGGTTGGATGCTTATGAGGATCAGTACAACCA   1080
  D  E  E  Q  V  F  H  F  Y  W  L  D  A  Y  E  D  Q  Y  N  Q  - 355
ACCAGGTGTGGTATTTCTGTTTGGGAAAGTTTGGATTGAATCAGCCGAGACCCATGTGAG   1140
  P  G  V  V  F  L  F  G  K  V  W  I  E  S  A  E  T  H  V  S  - 375
CTGTTGTGTCATGGTGAAAAATATCGAGGAACGCTTTACTTCCTTCCCGTGAAATGAA    1200
  C  C  V  M  K  N  I  E  R  T  L  Y  F  L  P  R  E  M  K   - 395
AATTGATCTAAATACGGGGAAAGAAACAGGAACTCCAATTTCAATGAAGGATGTTTATGA   1260
  I  D  L  N  T  G  K  E  T  P  I  S  M  K  D  V  Y  E   -  415
GGAATTTGATGAGAAAATAGCTAAAACATATGTAAAAATCATGAAGTTCAAGTCTAAGCCAGT   1320
  E  F  D  E  K  I  A  T  K  Y  K  I  M  K  F  K  S  K  P  V  - 435
GGAAAAGAACTATGCTTTTGAGATACCTCCAGATGTTCCAGAGAAAATCTGAGTACTTGGAAGT   1380
  E  K  N  Y  A  F  E  I  P  D  V  P  E  K  S  E  Y  L  E  V  - 455
TAAATACTCGGCTGAAATGCCAACACATCTAGCGCTTGGAACCTGTGTTCTTGATGAAAGATCAAAGG 1440
  K  Y  S  A  E  M  P  Q  L  P  Q  D  L  K  G  E  T  F  S  H - 475
TGTATTTGGACCAACACATCTAGCCTGGAACCTGTGTTCTTGATGAACAGAAAGATCAAAGG 1500
  V  F  G  T  N  T  S  S  L  E  F  L  M  N  R  K  I  K  G  -  495
ACCTTGTTGGCTTGAAGTAAAAAGTCCACAGTCTCTTGAATCAGCCAGTCAGTTGGTGTAA   1560
  P  C  W  L  E  V  K  S  P  Q  L  L  N  Q  P  V  S  W  C  K - 515
AGTTGAGGCAATGGCTTTGAAACCAGACCTGGTGAATGTAATTAAGGATGTCAGTCCACC   1620
  V  E  A  M  A  L  K  P  D  L  V  N  V  I  K  D  V  S  P  P - 535
ACCGGCTTGTCGTGATGGCTTTCAGCATGAAGACAATGCAGAAGAACCATCAAAA       1680
  P  L  V  M  A  F  S  M  K  T  M  Q  N  A  K  N  H  Q  N  -  555
TGAGATTATTGCTATGCCAGCTTTTGGTCCATCACAGTTTGCATTGGATAAAGCAGCCCC  1740
  E  I  I  A  M  A  A  L  V  H  H  S  F  A  L  D  K  A  A  P - 575
```

FIG. 3C

```
AAGCCTCCCTTTCAGTCACACTTTCTGTGTGTCTAAACCAAGGACTGTATTTTCC      1800
 K  P  P  F  Q  S  H  F  C  V  V  S  K  P  K  D  C  I  F  P    -595
ATATGCTTTCAAAGAAGTCATTGAGAAAAAGAATGTGAAGGTTGAGGTTGCTGCAACAGA  1860
 Y  A  F  K  E  V  I  E  K  K  N  V  K  V  E  V  A  T  E       -615
AAGAACACTGCTAGGTTTTTTCCTTGCAAAAGTTCACAAAGTTGATCCTGATATCATTGT  1920
 K  N  T  L  G  F  F  L  A  K  V  H  K  I  D  P  D  I  I  V    -635
GGGTCATAATATTTATGGGTTTGAACTGGAAGTACTGCAGAGAATTAATGTGTGCAA     1980
 G  H  N  I  Y  G  F  E  L  E  V  L  L  Q  R  I  N  V  C  K    -655
AGCTCCTCACTGGTCCAAGATAGGTCGACTGAAGCGATCCAACATGCCAAAGCTTGGGGG  2040
 A  P  H  W  S  K  I  G  R  L  K  R  S  N  M  P  K  L  G  G    -675
CCGGAGTGGATTTGGTGAAAGAATGCTACCTGTGGTGAATGATCTGTGATGTGGAAAT   2100
 R  S  G  F  G  E  R  N  A  T  C  G  R  M  I  C  D  V  E  I    -695
TTCAGCAAGGAATTCGTTGATTCGTTGTAAAAGCTACCATCTGTCTGAACTTGTTCAGCAGAT 2160
 S  A  K  E  L  I  R  C  K  S  Y  H  L  S  E  L  V  Q  I       -715
TCTAAAAACTGAAAGGGTTGTAATCCCAATGGAAAATATACAAAATATGTACAGTGAATC  2220
 L  K  T  E  R  V  V  I  P  M  E  N  I  Q  N  M  Y  S  E  S    -735
TTCTCAACTGTTATACCTGTTGCTTGAGCTAAAGTTCTTCCATTAGCATTGCAGATCACTAACATCGCTGGAACAT 2280
 S  Q  L  L  Y  L  L  E  H  T  W  K  D  A  K  F  I  L  Q  I    -755
CATGTGTGAGCTAAATGTTCTTCCATTAGCATTGCAGATCACTAACATCGCTGGAACAT  2340
 M  C  E  L  N  V  L  P  L  A  L  Q  I  T  N  I  A  G  N  I    -775
TATGTCCAGGACGCTGATGGGTGGACGATCCGAGCGTAACGAGTTCTTGTTGCTTCATGC 2400
 Y  V  P  G  R  *  W  V  D  D  P  S  V  T  S  S  C  S  S  C    -795
ATTTTACGAAAACAACTATATTGTGCCTGACAAGCAGATTTTCAGAAAGCCTCAGCAAA  2460
 M  S  R  T  L  M  G  G  R  S  E  R  N  E  F  L  L  H  A       -815
ACTGGGAGATGAAGATGAAGAAATTGATGGAGAATACCAATAAATACAAGAAAGGACGTAA 2520
 F  Y  E  N  N  Y  I  V  P  D  K  Q  I  F  R  K  P  Q  K       -835
GAAAGCAGCTTATGCTGGAGGCTTGGTTTTGGACCCCAAAGTTGGTTTTATGATAAGTT  2580
 K [A] A  Y  A  G  G  L  V  L  D  P  K  V  G  F  Y  D  K  F    -855
```

FROM FIG. 3B

FROM FIG. 3C →

TO FIG. 3E →

```
CATTTGCTTCTCAACAGTCTATATCCTTCCATCATTCAGGAATTTAACATTTG      2640
 I   L   L   D   F   N   S   L   Y   P   S   I   I   Q   E   F   N   I   C      -875
TTTTACAACAGTACAAAGAGTTGCTTCAGAGGCACAGAAAGTTACAGAGGATGGAGAACA  2700
 F   T   T   V   Q   R   V   A   S   E   A   Q   K   V   T   E   D   C   E   Q  -895
AGAACAGATCCCTGAGTTGCCAGATCCAAGCTTAGAGAAATGGGCATTTTGCCCAGAGAT  2760
 E   Q   I   P   E   L   P   D   P   S   L   E   M   G   I   L   P   R   E   I  -915
CCGGAAAACTGGTAGAACGGAGAAAACAAGTCAAACAGTAATGAAACAGCAAGACTTAAA  2820
 R   K   L   V   E   R   R   K   Q   V   K   Q   L   M   K   Q   Q   D   L   N  -935
TCCAGACCTTATTCTTCAGTATGACATTCGACAGAAGGCTTTGAAGCTTCACAGGAACAG  2880
 P   D   L   I   L   Q   Y   D   I   R   Q   K   A   L   K   L   T   A   N   S  -955
TATGTATGGTTGCCTGGGATTTTCCTATAGCAGATTTTACGCCAAACCACTGGCTGCCTT  2940
 M   Y   G   C   L   G   F   S   Y   S   R   F   Y   A   K   P   L   A   A   L  -975
GGTGACATACAAAGGAAAGGAGATTTTGATGCATACAGAAGAGATGGTACAAAAGATGAA  3000
 V   T   Y   K   G   R   E   I   L   M   H   T   K   E   M   V   Q   K   M   N  -995
TCTTGAAGTTATTTATGGAGACACATTGATGGGAAACAAGGTAAAAAGTGAAGTGAATAAGTTGTACAAACT  3060
 L   E   V   I   Y   G   D   T   D   S   I   M   I   N   T   N   S   T   N   L  -1015
GGAAGAAGTATTTAAGTTACTGATGATGGGGTTTTCAAGTCTCTGCTACTGCTGAAAAAGAAGTA  3120
 E   E   V   F   K   L   G   N   K   V   K   S   E   V   N   K   L   Y   K   L  -1035
GCTTGAAATAGACATTGATGGTGTTGAGCCAACGTCGGATGGAATTATGTCACCAAACAGGAGCTCAA  3180
 L   E   I   D   I   D   G   V   F   K   S   L   L   L   K   K   K   Y   L  -1055
CGCTGCTCTGGTCTTGTTGAGCCAACGTCGGATGGAATTATGTCACCAAACAGGAGCTCAA  3240
 A   A   L   V   E   P   T   S   D   G   N   Y   V   T   K   Q   E   L   K  -1075
AGGATTAGATATAGTTAGAAGAGATTGGTGTGATCTTGCTAAAGACACTGGAAACTTTGT  3300
 R   L   D   I   V   R   R   D   W   C   D   L   A   K   D   T   G   N   F   V  -1095
GATTGGCCAGATTCTTTCTGATCAAAGCCGGACACTATAGTGGAAAACATTCAGAAGAGAG  3360
 I   G   Q   I   L   S   D   Q   S   R   D   T   I   V   E   N   I   Q   K   R  -1115
GCTGATAGAAATTGGAGAAATGTGTAAATGGGAGTGTCCCAGTGAGCCAGTTGAAAT  3420
 L   I   E   I   C   E   N   V   L   N   G   S   V   P   V   S   Q   F   E   I  -1135
```

FIG. 3E

FROM FIG. 3D

TO FIG. 3F

```
TAACAAGGCATTGACAAAGGATCCCCAGGATTACCCTGATAAAAAAGCCTACCTCATGT    3480
 N  K  A  L  T  K  D  P  Q  D  Y  P  D  K  K  S  L  P  H  V   -1155
ACATGTTGCCCTCTGGATAAATTCTCAAGGAGGCAGAAAGGTGAAAGCTGGAGATACTGT    3540
 H  V  A  L  W  I  N  S  Q  G  G  R  K  V  K  A  G  D  T  V   -1175
GTCATATGTCATCTGTCAGGATGGATCAAACCTCACTGCAAGTCAGAGGGCCTATGCGCC    3600
 S  Y  V  I  C  Q  D  G  S  N  L  T  A  S  Q  R  A  Y  A  P   -1195
TGAGCAGTGCAGAAACAGGATAATCTAACCATTGACACACCCAGTACTACCTGGCCCAGCA    3660
 E  Q  L  Q  K  Q  D  N  L  T  I  D  T  Q  Y  L  A  Q  Q       -1215
GATCCACCCAGTCGTGGCTCGGATCGTGAACCAATAGACGGAATTGATGCTGTCCTCAT     3720
 I  H  P  V  A  R  I  C  E  P  I  D  G  I  D  A  V  L  I      -1235
TGCAACGTGGGGACTTGACCCCAATTTAGAGTTCATCATTATCATAAAGATGA           3780
 A  T  W  L  G  L  D  P  T  Q  F  R  V  H  H  Y  H  K  D  E   -1255
AGAGAATGATGCTCACTTGGTGCCCAGCACAGTCCACTGATGAAGAGAAATACAGGGA      3840
 E  N  D  A  L  L  G  G  P  A  Q  L  T  D  E  E  K  Y  R  D   -1275
CTGTGAAAGATTCAAATGTCCATGCCCTACATGTGGAACTGAGAATATTTATGATAATGT    3900
 C  E  R  F  K  C  P  C  P  T  C  G  T  E  N  I  Y  D  N  V   -1295
CTTTGATGGTTCGGGAACAGATATGGAGCCCAGCTGTATCGTTGTCAGTAACATCGATTG    3960
 F  D  G  S  G  T  D  M  E  P  S  L  Y  R  C  S  N  I  D  C   -1315
TAAGGCTTCACCTCTGACCTTTACAGTACTGTCAAACTGAGCAACAAATTGATCATGGAGATTAG    4020
 K  A  S  P  L  T  F  T  V  L  S  N  K  L  I  M  D  I  R      -1335
ACGTTTCATTAAAAAGTACTATGATGGCTGGTTGATATGTGAAGAGCCAACCTGTCGCAA    4080
 R  F  I  K  K  Y  Y  D  G  W  L  I  C  E  E  P  T  C  R  N   -1355
TCGAACTCGTCACTTCCCCCTTCAATTCTCCCGAACTGGGCCTCTTTGCCCAGCCTGCAT    4140
 R  T  R  H  L  P  L  Q  F  S  R  T  G  P  L  C  P  A  C  M   -1375
GAAAGCTACACTTCAACCAGAGTATTCTGACAAGTCCCTGTACACCCAGCAGTGTGCTTTA    4200
 K  A  T  L  Q  P  E  Y  S  D  K  S  L  Y  T  Q  L  C  F  Y   -1395
CCGGTACATTTTTGATGCGGAGTGTGCACTGGAGAAAACTTACCGATCATGAGAAAGA      4260
 R  Y  I  F  D  A  E  C  A  L  E  K  L  T  T  D  H  E  K  D   -1415
```

FIG. 3F

```
TAAATTGAAGAAGCAATTTTTACCCCCAAAGTTCTGCAGGACTACAGAAAACTCAAGAA    4320
 K  L  K  K  Q  F  F  T  P  K  V  L  Q  D  Y  R  K  L  K  N   -1435
CACAGCAGAGCAATTCTTGTCCCGAAGTGGCTACTCCGAAGTGAATCTGAGCAAACTCTT    4380
 T  A  E  Q  F  L  S  R  S  G  Y  S  E  V  N  L  S  K  L  F   -1455
CGCTGGTTGTGCCGTGAAATCCTAAGGAGTAACCAAGGAGGGGTAGTTG              4440
 R  W  L  C  R  E  S  *                                        -1462
 A  G  C  A  V  K  S  *
AAAAATCCCAGCTTCCTCTGTGCCTCCACTCTGGCCCTAAATGCTCTTCCTCCAGCATCTGTT    4500
TCTCCCTTGGGACTGTGTCTCATGTTGTGTGAATGTAGACCAGGAAAGGGGCTGCAAA    4560
AATGTGAGTCTAATGTTCGTAAGCATCAGAAATTCCTGTCTTCATATTAAGATGTAC    4620
TGCTTTAAAACACAACTCCAGAGCCCCCAAGCTCCCCAAGCTCCTGAAGAC            4680
CCGGTTTCTGAGGAGGGAAATTGTACTTGGATTGAGAGTAGCTGAATGTAAGTGACC    4740
CCAGGCTTTGCTCAGGCTTTAGCCTATGCTCCCCCACATAAAGAGAGCTTCTCAGAG    4800
CCTGACTGAAGAGCTGACGTTTTGCTTTTCATATGCCAATTAAACCCGGTCTAAATCCA    4860
AATGCTTCCAGCCATCCAGGAGTTAGAAGCCTTGCACTCACTAAATAGATTAAACAGAGCAGGCTTG    4920
GCTGAGGGGAAGATTAGAAGTCCAAAGTTTATACAACAAGAAAGCACAT            4980
TTTGTTGAATTGTCTCCAAAGTCTAAATACTCTAACAATCATTACATGTGTAGGGGTTACGGTGAGGATCA    5040
TCCCTTTTGCCCCTTAAATACTCTAACAATCCATTAACATGTGTAGGGGTTACGGTGAGGATCA    5100
TGAAAATAATTTGATACTCTTAACAATCCATTAACATGTGTAGGGGTTACGGTGAGGATCA    5160
TGTGTTGTATTCGAAAAAACGGGAGAGGGATGCTTAATTGGCCCTGCTATTTTT        5220
TCTCATTTCTTCACAATAGGACCGTCTTTGGCAGCAGCAAAATGTATTTCAGTATGGCAG    5280
TCTTTCCTCTTACATTATTGGTAAGATTATACTAACAAAATGTTTCCCCTGTACAAT    5340
TATGCTGTGTTTTAAAAAAACATTGACCTGTGTGTTTTTATAAAAGAAGTATGTTGT    5400
GCCTTCTTCTTAAGAATAAAGTTTTCTAAAGGG                              5433
```

↑ FROM FIG. 3E

M13mp18   5'- AGGCATCGAAGCTTGGCACTGGCCGTCG-3'
               TTCGAACCGTGACCGGCAGC-5'

M13mp18   5'-GTCGTGACTGGGAAAACCCTGGCG-3'
             CAGCACTGACCCTTTTGGGACCGC-5'

SEQUENCE LISTING

<160> NUMBER OF SEQ ID NOS: 35

<210> SEQ ID NO 1
<211> LENGTH: 4440
<212> TYPE: DNA
<213> ORGANISM: Homo sapiens

<400> SEQUENCE: 1

| | | | | | |
|---|---|---|---|---|---|
| ggggagattc | gggaccatgg | cacctgtgca | cggcgacgac | tctctgtcag | attcagggag | 60 |
| ttttgtatct | tctcgagccc | ggcgagaaaa | aaaatcaaag | aagggcgcc | aagaagccct | 120 |
| agaaagactg | aaaaaggcta | aagctggtga | aagtataaa | tatgaagtcg | aggacttcac | 180 |
| aggtgtttat | gaagaagttg | atgaagaaca | gtattcgaag | ctggttcagg | cacgccagga | 240 |
| tgatgactgg | attgtggatg | atgatggtat | tggctatgtg | aagatggcc | gagagatttt | 300 |
| tgatgatgac | cttgaagatg | atgcccttga | tgctgatgag | aaaggaaaag | atggtaaagc | 360 |
| acgcaataaa | gacaagagga | atgtaaagaa | gctcgcagtg | acaaaaccga | acaacattaa | 420 |
| gtcaatgttc | attgcttgtg | ctggaaagaa | aactgcagat | aaagctgtag | acttgtccaa | 480 |
| ggatggtctg | ctaggtgaca | ttctacagga | tcttaacact | gagacacctc | aaataactcc | 540 |
| accacctgta | atgatactga | agaagaaaag | atccattgga | gcttcaccga | atcctttctc | 600 |
| tgtgcacacc | gccacggcag | ttccttcagg | aaaaattgct | tcccctgtct | ccagaaagga | 660 |
| gcctccatta | actcctgttc | ctcttaaacg | tgctgaattt | gctggcgatg | atgtacaggt | 720 |
| cgagagtaca | gaagaagagc | aggagtcagg | ggcaatggag | tttgaagatg | gtgactttga | 780 |
| tgagcccatg | gaagttgaag | aggtggacct | ggagcctatg | gctgccaagg | cttgggacaa | 840 |
| agagagtgag | ccagcagagg | aagtgaaaca | agaggcggat | tctgggaaag | ggaccgtgtc | 900 |
| ctacttagga | agttttctcc | cggatgtctc | ttgtttggac | attgatcaag | aaggtgatag | 960 |
| cagtttctca | gtgcaagaag | ttcaagtgga | ttccagtcac | ctcccattgg | taaaaggggc | 1020 |
| agatgaggaa | caagtattcc | actttattg | gttggatgct | tatgaggatc | agtacaacca | 1080 |
| accaggtgtg | gtatttctgt | ttgggaaagt | ttggattgaa | tcagccgaga | cccatgtgag | 1140 |
| ctgttgtgtc | atggtgaaaa | atatcgagcg | aacgctttac | ttccttcccc | gtgaaatgaa | 1200 |
| aattgatcta | aatacgggga | agaaacagg | aactccaatt | tcaatgaagg | atgtttatga | 1260 |
| ggaatttgat | gagaaaatag | caacaaaata | taaaattatg | aagttcaagt | ctaagccagt | 1320 |
| ggaaaagaac | tatgcttttg | agataccctga | tgttccagaa | aaatctgagt | acttggaagt | 1380 |
| taaatactcg | gctgaaatgc | cacagcttcc | tcaagatttg | aaaggagaaa | ctttttctca | 1440 |
| tgtatttggg | accaacacat | ctagcctgga | actgttcttg | atgaacagaa | agatcaaagg | 1500 |
| accttgttgg | cttgaagtaa | aaagtccaca | gctcttgaat | cagccagtca | gttggtgtaa | 1560 |
| agttgaggca | atggctttga | aaccagacct | ggtgaatgta | attaaggatg | tcagtccacc | 1620 |
| accgcttgtc | gtgatggctt | tcagcatgaa | gacaatgcag | aatgcaaaga | accatcaaaa | 1680 |
| tgagattatt | gctatggcag | ctttggtcca | tcacagtttt | gcattggata | aagcagcccc | 1740 |
| aaagcctccc | tttcagtcac | acttctgtgt | tgtgtctaaa | ccaaaggact | gtattttcc | 1800 |
| atatgctttc | aaagaagtca | ttgagaaaaa | gaatgtgaag | gttgaggttg | ctgcaacaga | 1860 |
| aagaacactg | ctaggttttt | tccttgcaaa | agttcacaaa | attgatcctg | atatcattgt | 1920 |
| gggtcataat | atttatgggt | ttgaactgga | agtactactg | cagagaatta | atgtgtgcaa | 1980 |
| agctcctcac | tggtccaaga | taggtcgact | gaagcgatcc | aacatgccaa | agcttgggg | 2040 |

```
ccggagtgga tttggtgaaa gaaatgctac ctgtggtcga atgatctgtg atgtggaaat   2100
ttcagcaaag gaattgattc gttgtaaaag ctaccatctg tctgaacttg ttcagcagat   2160
tctaaaaact gaaagggttg taatcccaat ggaaaatata caaaatatgt acagtgaatc   2220
ttctcaactg ttatacctgt tggaacacac ctggaaagat gccaagttca ttttgcagat   2280
catgtgtgag ctaaatgttc ttccattagc attgcagatc actaacatcg ctgggaacat   2340
tatgtccagg acgctgatgg gtggacgatc cgagcgtaac gagttcttgt tgcttcatgc   2400
attttacgaa aacaactata ttgtgcctga caagcagatt ttcagaaagc ctcagcaaaa   2460
actgggagat gaagatgaag aaattgatgg agataccaat aaatacaaga aggacgtaa    2520 gaaagcagct tatgctggag cttggtttt ggaccccaaa gttggttttt atgataagtt    2580
cattttgctt ctggacttca acagtctata tccttccatc attcaggaat ttaacatttg   2640
ttttacaaca gtacaaagag ttgcttcaga ggcacagaaa gttacagagg atggagaaca   2700
agaacagatc cctgagttgc cagatccaag cttagaaatg ggcattttgc ccagagagat   2760
ccggaaactg gtagaacgga gaaaacaagt caaacagcta atgaaacagc aagacttaaa   2820
tccagacctt attcttcagt atgacattcg acagaaggct ttgaagctca cagcgaacag   2880
tatgtatggt tgcctgggat tttcctatag cagattttac gccaaaccac tggctgcctt   2940
ggtgacatac aaaggaaggg agattttgat gcatacgaaa gagatggtac aaaagatgaa   3000
tcttgaagtt atttatggag atacagattc aattatgata acaccaata gcaccaatct    3060 ggaagaagta tttaagttgg gaaacaaggt aaaaagtgaa gtgaataagt tgtacaaact   3120
gcttgaaata gacattgatg gggttttcaa gtctctgcta ctgctgaaaa aaagaagta    3180 cgctgctctg gttgttgagc caacgtcgga tgggaattat gtcaccaaac aggagctcaa   3240
aggattagat atagttagaa gagattggtg tgatcttgct aaagacactg gaaactttgt   3300
gattggccag attctttctg atcaaagccg ggacactata gtggaaaaca ttcagaagag   3360
gctgatagaa attggagaaa atgtgctaaa tggcagtgtc ccagtgagcc agtttgaaat   3420
taacaaggca ttgacaaagg atccccagga ttaccctgat aaaaaaagcc tacctcatgt   3480
acatgttgcc ctctggataa attctcaagg aggcagaaag gtgaaagctg agatactgt    3540 gtcatatgtc atctgtcagg atggatcaaa cctcactgca agtcagaggg cctatgcgcc   3600
tgagcagctg cagaaacagg ataatctaac cattgacacc cagtactacc tggcccagca   3660
gatccaccca gtcgtggctc ggatctgtga accaatagac ggaattgatg ctgtcctcat   3720
tgcaacgtgg ttgggacttg accccaccca atttagagtt catcattatc ataaagatga   3780
agagaatgat gctctacttg gtggcccagc acagctcact gatgaagaga aatacaggga   3840
ctgtgaaaga ttcaaatgtc catgccctac atgtggaact gagaatattt atgataatgt   3900
ctttgatggt tcgggaacag atatggagcc cagcttgtat cgttgcagta acatcgattg   3960
taaggcttca cctctgacct ttacagtaca actgagcaac aaattgatca tggacattag   4020
acgtttcatt aaaaagtact atgatggctg gttgatatgt aagagccaa cctgtcgcaa    4080 tcgaactcgt caccttcccc ttcaattctc ccgaactggg cctcttgcc cagcctgcat    4140 gaaagctaca cttcaaccag agtattctga caagtccctg tacacccagc tgtgcttta    4200 ccggtacatt tttgatgcgg agtgtgcact ggagaaactt actaccgatc atgagaaaga   4260
taaattgaag aagcaatttt ttacccccaa agttctgcag gactacagaa aactcaagaa   4320
cacagcagag caattcttgt cccgaagtgg ctactccgaa gtgaatctga gcaaactctt   4380
```

```
cgctggttgt gccgtgaaat cctaagggaa tcccaggagt aaccaaggag ggggtagttg      4440

<210> SEQ ID NO 2
<211> LENGTH: 29
<212> TYPE: DNA
<213> ORGANISM: Homo sapiens

<400> SEQUENCE: 2
cgacggccag tgccaagctt tttttttt                                          29

<210> SEQ ID NO 3
<211> LENGTH: 28
<212> TYPE: DNA
<213> ORGANISM: Homo sapiens

<400> SEQUENCE: 3
aggcatcgaa gcttggcact ggccgtcg                                          28

<210> SEQ ID NO 4
<211> LENGTH: 24
<212> TYPE: DNA
<213> ORGANISM: Homo sapiens

<400> SEQUENCE: 4
cgccagggtt ttcccagtca cgac                                              24

<210> SEQ ID NO 5
<211> LENGTH: 24
<212> TYPE: DNA
<213> ORGANISM: Homo sapiens

<400> SEQUENCE: 5
gtcgtgactg ggaaaaccct ggcg                                              24

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 6
gctgcctatg ctggcggcct ggtgctggac ccaag                                  35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 7
cttggggtcc agcaccaggc cgccagcata ggcagc                                 36

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 8
cttcacctcc agccaggtgg ggcc                                              24
```

```
<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (15)
<223> OTHER INFORMATION: N = a, c, t, or g.

<400> SEQUENCE: 9
tayathttyg aygcnga                                                17

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 10
tacatctttg atgctgagac agccctggag aag                               33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 11
cttctccagg gctgtctcag catcaaagat gta                               33

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 12
gtagaacacc tgctgcagca gctcatc                                     27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (1)
<223> OTHER INFORMATION: i
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (16)
<223> OTHER INFORMATION: i
<220> FEATURE:
```

```
<221> NAME/KEY: modified_base
<222> LOCATION: (19)
<223> OTHER INFORMATION: i
<220> FEATURE:
<221> NAME/KEY: modified_base
<222> LOCATION: (22)
<223> OTHER INFORMATION: i
<220> FEATURE:
<221> NAME/KEY: misc_feature
<222> LOCATION: (1)
<223> OTHER INFORMATION: N = a, c, t, or g.
<220> FEATURE:
<221> NAME/KEY: misc_feature
<222> LOCATION: (4)
<223> OTHER INFORMATION: N = a, c, t, or g.
<220> FEATURE:
<221> NAME/KEY: misc_feature
<222> LOCATION: (7)
<223> OTHER INFORMATION: N = a, c, t, or g.
<220> FEATURE:
<221> NAME/KEY: misc_feature
<222> LOCATION: (10)
<223> OTHER INFORMATION: N = a, c, t, or g.
<220> FEATURE:
<221> NAME/KEY: misc_feature
<222> LOCATION: (16)
<223> OTHER INFORMATION: N = a, c, t, or g.
<220> FEATURE:
<221> NAME/KEY: misc_feature
<222> LOCATION: (19)
<223> OTHER INFORMATION: N = a, c, t, or g.
<220> FEATURE:
<221> NAME/KEY: misc_feature
<222> LOCATION: (22)
<223> OTHER INFORMATION: N = a, c, t, or g.

<400> SEQUENCE: 13
nttnacntcn arccangtng gncc                                              24

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:  Synthetic
<220> FEATURE:
<221> NAME/KEY: modified_base
<222> LOCATION: (1)
<223> OTHER INFORMATION: i
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (13)
<223> OTHER INFORMATION: i
<220> FEATURE:
<221> NAME/KEY: modified_base
<222> LOCATION: (16)
<223> OTHER INFORMATION: i
<220> FEATURE:
<221> NAME/KEY: modified_base
<222> LOCATION: (19)
<223> OTHER INFORMATION: i
<220> FEATURE:
<221> NAME/KEY: modified_base
<222> LOCATION: (22)
<223> OTHER INFORMATION: i
```

```
<220> FEATURE:
<221> NAME/KEY: modified_base
<222> LOCATION: (25)
<223> OTHER INFORMATION: i
<220> FEATURE:
<221> NAME/KEY: modified_base
<222> LOCATION: (28)
<223> OTHER INFORMATION: i
<220> FEATURE:
<221> NAME/KEY: modified_base
<222> LOCATION: (31)
<223> OTHER INFORMATION: i
<220> FEATURE:
<221> NAME/KEY: modified_base
<222> LOCATION: (34)
<223> OTHER INFORMATION: i
<220> FEATURE:
<221> NAME/KEY: misc_feature
<222> LOCATION: (1)
<223> OTHER INFORMATION: N = a, c, t, or g.
<220> FEATURE:
<221> NAME/KEY: misc_feature
<222> LOCATION: (4)
<223> OTHER INFORMATION: N = a, c, t, or g.
<220> FEATURE:
<221> NAME/KEY: misc_feature
<222> LOCATION: (7)
<223> OTHER INFORMATION: N = a, c, t, or g.
<220> FEATURE:
<221> NAME/KEY: misc_feature
<222> LOCATION: (10)
<223> OTHER INFORMATION: N = a, c, t, or g.
<220> FEATURE:
<221> NAME/KEY: misc_feature
<222> LOCATION: (13)
<223> OTHER INFORMATION: N = a, c, t, or g.
<220> FEATURE:
<221> NAME/KEY: misc_feature
<222> LOCATION: (16)
<223> OTHER INFORMATION: N = a, c, t, or g.
<220> FEATURE:
<221> NAME/KEY: misc_feature
<222> LOCATION: (19)
<223> OTHER INFORMATION: N = a, c, t, or g.
<220> FEATURE:
<221> NAME/KEY: misc_feature
<222> LOCATION: (22)
<223> OTHER INFORMATION: N = a, c, t, or g.
<220> FEATURE:
<221> NAME/KEY: misc_feature
<222> LOCATION: (25)
<223> OTHER INFORMATION: N = a, c, t, or g.
<220> FEATURE:
<221> NAME/KEY: misc_feature
<222> LOCATION: (28)
<223> OTHER INFORMATION: N = a, c, t, or g.
<220> FEATURE:
<221> NAME/KEY: misc_feature
<222> LOCATION: (31)
<223> OTHER INFORMATION: N = a, c, t, or g.
<220> FEATURE:
<221> NAME/KEY: misc_feature
<222> LOCATION: (34)
<223> OTHER INFORMATION: N = a, c, t, or g.

<400> SEQUENCE: 14
nttntcnggn acntcnggna tntcnaangc ntantt                    36

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (1)
```

-continued

```
<223> OTHER INFORMATION: i
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (13)
<223> OTHER INFORMATION: i
<220> FEATURE:
<221> NAME/KEY: modified_base
<222> LOCATION: (16)
<223> OTHER INFORMATION: i
<220> FEATURE:
<221> NAME/KEY: modified_base
<222> LOCATION: (19)
<223> OTHER INFORMATION: i
<220> FEATURE:
<221> NAME/KEY: modified_base
<222> LOCATION: (22)
<223> OTHER INFORMATION: i
<220> FEATURE:
<221> NAME/KEY: modified_base
<222> LOCATION: (25)
<223> OTHER INFORMATION: i
<220> FEATURE:
<221> NAME/KEY: modified_base
<222> LOCATION: (28)
<223> OTHER INFORMATION: i
<220> FEATURE:
<221> NAME/KEY: modified_base
<222> LOCATION: (31)
<223> OTHER INFORMATION: i
<220> FEATURE:
<221> NAME/KEY: misc_feature
<222> LOCATION: (1)
<223> OTHER INFORMATION: N = a, c, t, or g.
<220> FEATURE:
<221> NAME/KEY: misc_feature
<222> LOCATION: (4)
<223> OTHER INFORMATION: N = a, c, t, or g.
<220> FEATURE:
<221> NAME/KEY: misc_feature
<222> LOCATION: (7)
<223> OTHER INFORMATION: N = a, c, t, or g.
<220> FEATURE:
<221> NAME/KEY: misc_feature
<222> LOCATION: (10)
<223> OTHER INFORMATION: N = a, c, t, or g.
<220> FEATURE:
<221> NAME/KEY: misc_feature
<222> LOCATION: (13)
<223> OTHER INFORMATION: N = a, c, t, or g.
<220> FEATURE:
<221> NAME/KEY: misc_feature
<222> LOCATION: (16)
<223> OTHER INFORMATION: N = a, c, t, or g.
<220> FEATURE:
<221> NAME/KEY: misc_feature
<222> LOCATION: (19)
<223> OTHER INFORMATION: N = a, c, t, or g.
<220> FEATURE:
<221> NAME/KEY: misc_feature
<222> LOCATION: (22)
<223> OTHER INFORMATION: N = a, c, t, or g.
<220> FEATURE:
<221> NAME/KEY: misc_feature
<222> LOCATION: (25)
<223> OTHER INFORMATION: N = a, c, t, or g.
<220> FEATURE:
<221> NAME/KEY: misc_feature
```

```
<222> LOCATION: (28)
<223> OTHER INFORMATION: N = a, c, t, or g.
<220> FEATURE:
<221> NAME/KEY: misc_feature
<222> LOCATION: (31)
<223> OTHER INFORMATION: N = a, c, t, or g.

<400> SEQUENCE: 15
nttntcnarn gcngtntcng cntcnaanat nta                              33

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:  Synthetic
<220> FEATURE:
<221> NAME/KEY: modified_base
<222> LOCATION: (1)
<223> OTHER INFORMATION: i
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (13)
<223> OTHER INFORMATION: i
<220> FEATURE:
<221> NAME/KEY: modified_base
<222> LOCATION: (16)
<223> OTHER INFORMATION: i
<220> FEATURE:
<221> NAME/KEY: modified_base
<222> LOCATION: (19)
<223> OTHER INFORMATION: i
<220> FEATURE:
<221> NAME/KEY: modified_base
<222> LOCATION: (22)
<223> OTHER INFORMATION: i
<220> FEATURE:
<221> NAME/KEY: modified_base
<222> LOCATION: (25)
<223> OTHER INFORMATION: i
<220> FEATURE:
<221> NAME/KEY: modified_base
<222> LOCATION: (28)
<223> OTHER INFORMATION: i
<220> FEATURE:
<221> NAME/KEY: modified_base
<222> LOCATION: (31)
<223> OTHER INFORMATION: i
<220> FEATURE:
<221> NAME/KEY: modified_base
<222> LOCATION: (34)
<223> OTHER INFORMATION: i
<220> FEATURE:
<221> NAME/KEY: misc_feature
<222> LOCATION: (1)
<223> OTHER INFORMATION: N = a, c, t, or g.
<220> FEATURE:
<221> NAME/KEY: misc_feature
<222> LOCATION: (4)
<223> OTHER INFORMATION: N = a, c, t, or g.
<220> FEATURE:
<221> NAME/KEY: misc_feature
<222> LOCATION: (7)
<223> OTHER INFORMATION: N = a, c, t, or g.
<220> FEATURE:
```

```
<221> NAME/KEY: misc_feature
<222> LOCATION: (10)
<223> OTHER INFORMATION: N = a, c, t, or g.
<220> FEATURE:
<221> NAME/KEY: misc_feature
<222> LOCATION: (13)
<223> OTHER INFORMATION: N = a, c, t, or g.
<220> FEATURE:
<221> NAME/KEY: misc_feature
<222> LOCATION: (16)
<223> OTHER INFORMATION: N = a, c, t, or g.
<220> FEATURE:
<221> NAME/KEY: misc_feature
<222> LOCATION: (19)
<223> OTHER INFORMATION: N = a, c, t, or g.
<220> FEATURE:
<221> NAME/KEY: misc_feature
<222> LOCATION: (22)
<223> OTHER INFORMATION: N = a, c, t, or g.
<220> FEATURE:
<221> NAME/KEY: misc_feature
<222> LOCATION: (25)
<223> OTHER INFORMATION: N = a, c, t, or g.
<220> FEATURE:
<221> NAME/KEY: misc_feature
<222> LOCATION: (28)
<223> OTHER INFORMATION: N = a, c, t, or g.
<220> FEATURE:
<221> NAME/KEY: misc_feature
<222> LOCATION: (31)
<223> OTHER INFORMATION: N = a, c, t, or g.
<220> FEATURE:
<221> NAME/KEY: misc_feature
<222> LOCATION: (34)
<223> OTHER INFORMATION: N = a, c, t, or g.

<400> SEQUENCE: 16
nttntcnggn acntcnggna tntcnaangc ntantt                              36

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (3)
<223> OTHER INFORMATION: N = a, c, t, or g.
<220> FEATURE:
<221> NAME/KEY: misc_feature
<222> LOCATION: (6)
<223> OTHER INFORMATION: N = a, c, t, or g.

<400> SEQUENCE: 17
acnggnaayt tygt                                                      14

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic

<400> SEQUENCE: 18
gatctgctgg gccaggtagt actgggtgtc aatggtcagg ttggtctg                 48

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
```

-continued

```
<400> SEQUENCE: 19
ccgggactgg tcagacagga tctggccaat cacaaagttg cctgt                45

<210> SEQ ID NO 20
<211> LENGTH: 22
<212> TYPE: DNA
<213> ORGANISM: Homo sapiens

<400> SEQUENCE: 20
gaactatgct ttgagatacc tg                                         22

<210> SEQ ID NO 21
<211> LENGTH: 23
<212> TYPE: DNA
<213> ORGANISM: Homo sapiens

<400> SEQUENCE: 21
gaactatgct tttgagatac ctg                                        23

<210> SEQ ID NO 22
<211> LENGTH: 33
<212> TYPE: DNA
<213> ORGANISM: Homo sapiens

<400> SEQUENCE: 22
gtaaaaaagt ccacagctct tgaatcagcc agt                             33

<210> SEQ ID NO 23
<211> LENGTH: 27
<212> TYPE: DNA
<213> ORGANISM: Homo sapiens

<400> SEQUENCE: 23
gtaaaaagtc cacagctctt gaatcag                                    27

<210> SEQ ID NO 24
<211> LENGTH: 27
<212> TYPE: DNA
<213> ORGANISM: Homo sapiens

<400> SEQUENCE: 24
gtaaaaaagt ccacagctct taatcag                                    27

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 25
gaactatgca ttcgagatac ctga                                       24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 26
gaactatgca ttcgagatac ctg                                        23
```

-continued

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 27
cgcccagcgg gcagag                                                           16

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 28
tgaccatgta acagagag                                                         18

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 29
tctcttctct ctctcttact ctctgttaca tggtca                                     36

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 30
tctcttctcc tctcttctcc attctctgcc cgctgggcg                                  39

<210> SEQ ID NO 31
<211> LENGTH: 1462
<212> TYPE: PRT
<213> ORGANISM: Homo sapiens

<400> SEQUENCE: 31

Met Ala Pro Val His Gly Asp Asp Ser Leu Ser Asp Ser Gly Ser Phe
 1               5                  10                  15

Val Ser Ser Arg Ala Arg Arg Glu Lys Lys Ser Lys Lys Gly Arg Gln
            20                  25                  30

Glu Ala Leu Glu Arg Leu Lys Lys Ala Lys Ala Gly Glu Lys Tyr Lys
        35                  40                  45

Tyr Glu Val Glu Asp Phe Thr Gly Val Tyr Glu Glu Val Asp Glu Glu
    50                  55                  60

Gln Tyr Ser Lys Leu Val Gln Ala Arg Gln Asp Asp Asp Trp Ile Val
65                  70                  75                  80

Asp Asp Asp Gly Ile Gly Tyr Val Glu Asp Gly Arg Glu Ile Phe Asp
                85                  90                  95

Asp Asp Leu Glu Asp Asp Ala Leu Asp Ala Asp Glu Lys Gly Lys Asp
            100                 105                 110

Gly Lys Ala Arg Asn Lys Asp Lys Arg Asn Val Lys Lys Leu Ala Val
        115                 120                 125

-continued

```
Thr Lys Pro Asn Asn Ile Lys Ser Met Phe Ile Ala Cys Ala Gly Lys
    130                 135                 140
Lys Thr Ala Asp Lys Ala Val Asp Leu Ser Lys Asp Gly Leu Leu Gly
145                 150                 155                 160
Asp Ile Leu Gln Asp Leu Asn Thr Glu Thr Pro Gln Ile Thr Pro Pro
                165                 170                 175
Pro Val Met Ile Leu Lys Lys Arg Ser Ile Gly Ala Ser Pro Asn
            180                 185                 190
Pro Phe Ser Val His Thr Ala Thr Ala Val Pro Ser Gly Lys Ile Ala
        195                 200                 205
Ser Pro Val Ser Arg Lys Glu Pro Pro Leu Thr Pro Val Pro Leu Lys
    210                 215                 220
Arg Ala Glu Phe Ala Gly Asp Asp Val Gln Val Ser Thr Glu Glu
225                 230                 235                 240
Glu Gln Glu Ser Gly Ala Met Glu Phe Glu Asp Gly Asp Phe Asp Glu
                245                 250                 255
Pro Met Glu Val Glu Glu Val Asp Leu Glu Pro Met Ala Ala Lys Ala
            260                 265                 270
Trp Asp Lys Glu Ser Glu Pro Ala Glu Glu Val Lys Gln Glu Ala Asp
        275                 280                 285
Ser Gly Lys Gly Thr Val Ser Tyr Leu Gly Ser Phe Leu Pro Asp Val
    290                 295                 300
Ser Cys Trp Asp Ile Asp Gln Glu Gly Asp Ser Ser Phe Ser Val Gln
305                 310                 315                 320
Glu Val Gln Val Asp Ser Ser His Leu Pro Leu Val Lys Gly Ala Asp
                325                 330                 335
Glu Glu Gln Val Phe His Phe Tyr Trp Leu Asp Ala Tyr Glu Asp Gln
            340                 345                 350
Tyr Asn Gln Pro Gly Val Val Phe Leu Phe Gly Lys Val Trp Ile Glu
        355                 360                 365
Ser Ala Glu Thr His Val Ser Cys Cys Val Met Val Lys Asn Ile Glu
    370                 375                 380
Arg Thr Leu Tyr Phe Leu Pro Arg Glu Met Lys Ile Asp Leu Asn Thr
385                 390                 395                 400
Gly Lys Glu Thr Gly Thr Pro Ile Ser Met Lys Asp Val Tyr Glu Glu
                405                 410                 415
Phe Asp Glu Lys Ile Ala Thr Lys Tyr Lys Ile Met Lys Phe Lys Ser
            420                 425                 430
Lys Pro Val Glu Lys Asn Tyr Ala Phe Glu Ile Pro Asp Val Pro Glu
        435                 440                 445
Lys Ser Glu Tyr Leu Glu Val Lys Tyr Ser Ala Glu Met Pro Gln Leu
    450                 455                 460
Pro Gln Asp Leu Lys Gly Glu Thr Phe Ser His Val Phe Gly Thr Asn
465                 470                 475                 480
Thr Ser Ser Leu Glu Leu Phe Leu Met Asn Arg Lys Ile Lys Gly Pro
                485                 490                 495
Cys Trp Leu Glu Val Lys Ser Pro Gln Leu Leu Asn Gln Pro Val Ser
            500                 505                 510
Trp Cys Lys Val Glu Ala Met Ala Leu Lys Pro Asp Leu Val Asn Val
        515                 520                 525
Ile Lys Asp Val Ser Pro Pro Leu Val Val Met Ala Phe Ser Met
    530                 535                 540
```

-continued

```
Lys Thr Met Gln Asn Ala Lys Asn His Gln Asn Glu Ile Ile Ala Met
545                 550                 555                 560

Ala Ala Leu Val His His Ser Phe Ala Leu Asp Lys Ala Ala Pro Lys
                565                 570                 575

Pro Pro Phe Gln Ser His Phe Cys Val Val Ser Lys Pro Lys Asp Cys
                580                 585                 590

Ile Phe Pro Tyr Ala Phe Lys Glu Val Ile Glu Lys Lys Asn Val Lys
            595                 600                 605

Val Glu Val Ala Ala Thr Glu Arg Thr Leu Leu Gly Phe Phe Leu Ala
            610                 615                 620

Lys Val His Lys Ile Asp Pro Asp Ile Ile Val Gly His Asn Ile Tyr
625                 630                 635                 640

Gly Phe Glu Leu Glu Val Leu Leu Gln Arg Ile Asn Val Cys Lys Ala
                645                 650                 655

Pro His Trp Ser Lys Ile Gly Arg Leu Lys Arg Ser Asn Met Pro Lys
                660                 665                 670

Leu Gly Gly Arg Ser Gly Phe Gly Glu Arg Asn Ala Thr Cys Gly Arg
            675                 680                 685

Met Ile Cys Asp Val Glu Ile Ser Ala Lys Glu Leu Ile Arg Cys Lys
            690                 695                 700

Ser Tyr His Leu Ser Glu Leu Val Gln Gln Ile Leu Lys Thr Glu Arg
705                 710                 715                 720

Val Val Ile Pro Met Glu Asn Ile Gln Asn Met Tyr Ser Glu Ser Ser
                725                 730                 735

Gln Leu Leu Tyr Leu Leu Glu His Thr Trp Lys Asp Ala Lys Phe Ile
            740                 745                 750

Leu Gln Ile Met Cys Glu Leu Asn Val Leu Pro Leu Ala Leu Gln Ile
        755                 760                 765

Thr Asn Ile Ala Gly Asn Ile Met Ser Arg Thr Leu Met Gly Gly Arg
770                 775                 780

Ser Glu Arg Asn Glu Phe Leu Leu His Ala Phe Tyr Glu Asn Asn
785                 790                 795                 800

Tyr Ile Val Pro Asp Lys Gln Ile Phe Arg Lys Pro Gln Gln Lys Leu
            805                 810                 815

Gly Asp Glu Asp Glu Ile Asp Gly Asp Thr Asn Lys Tyr Lys Lys
            820                 825                 830

Gly Arg Lys Lys Ala Ala Tyr Ala Gly Gly Leu Val Leu Asp Pro Lys
        835                 840                 845

Val Gly Phe Tyr Asp Lys Phe Ile Leu Leu Asp Phe Asn Ser Leu
850                 855                 860

Tyr Pro Ser Ile Ile Gln Glu Phe Asn Ile Cys Phe Thr Thr Val Gln
865                 870                 875                 880

Arg Val Ala Ser Glu Ala Gln Lys Val Thr Glu Asp Gly Glu Gln Glu
                885                 890                 895

Gln Ile Pro Glu Leu Pro Asp Pro Ser Leu Glu Met Gly Ile Leu Pro
            900                 905                 910

Arg Glu Ile Arg Lys Leu Val Glu Arg Arg Lys Gln Val Lys Gln Leu
            915                 920                 925

Met Lys Gln Gln Asp Leu Asn Pro Asp Leu Ile Leu Gln Tyr Asp Ile
930                 935                 940

Arg Gln Lys Ala Leu Lys Leu Thr Ala Asn Ser Met Tyr Gly Cys Leu
945                 950                 955                 960

Gly Phe Ser Tyr Ser Arg Phe Tyr Ala Lys Pro Leu Ala Ala Leu Val
```

-continued

```
                965                 970                 975
Thr Tyr Lys Gly Arg Glu Ile Leu Met His Thr Lys Glu Met Val Gln
                980                 985                 990
Lys Met Asn Leu Glu Val Ile Tyr Gly Asp Thr Asp Ser Ile Met Ile
            995                1000                1005
Asn Thr Asn Ser Thr Asn Leu Glu Glu Val Phe Lys Leu Gly Asn Lys
       1010                1015                1020
Val Lys Ser Glu Val Asn Lys Leu Tyr Lys Leu Glu Ile Asp Ile
1025                1030                1035                1040
Asp Gly Val Phe Lys Ser Leu Leu Leu Lys Lys Lys Tyr Ala
            1045                1050                1055
Ala Leu Val Val Glu Pro Thr Ser Asp Gly Asn Tyr Val Thr Lys Gln
            1060                1065                1070
Glu Leu Lys Gly Leu Asp Ile Val Arg Arg Asp Trp Cys Asp Leu Ala
            1075                1080                1085
Lys Asp Thr Gly Asn Phe Val Ile Gly Gln Ile Leu Ser Asp Gln Ser
            1090                1095                1100
Arg Asp Thr Ile Val Glu Asn Ile Gln Lys Arg Leu Ile Glu Ile Gly
1105                1110                1115                1120
Glu Asn Val Leu Asn Gly Ser Val Pro Val Ser Gln Phe Glu Ile Asn
            1125                1130                1135
Lys Ala Leu Thr Lys Asp Pro Gln Asp Tyr Pro Asp Lys Lys Ser Leu
            1140                1145                1150
Pro His Val His Val Ala Leu Trp Ile Asn Ser Gln Gly Gly Arg Lys
            1155                1160                1165
Val Lys Ala Gly Asp Thr Val Ser Tyr Val Ile Cys Gln Asp Gly Ser
       1170                1175                1180
Asn Leu Thr Ala Ser Gln Arg Ala Tyr Ala Pro Glu Gln Leu Gln Lys
1185                1190                1195                1200
Gln Asp Asn Leu Thr Ile Asp Thr Gln Tyr Tyr Leu Ala Gln Gln Ile
            1205                1210                1215
His Pro Val Val Ala Arg Ile Cys Glu Pro Ile Asp Gly Ile Asp Ala
            1220                1225                1230
Val Leu Ile Ala Thr Trp Leu Gly Leu Asp Pro Thr Gln Phe Arg Val
       1235                1240                1245
His His Tyr His Lys Asp Glu Glu Asn Asp Ala Leu Leu Gly Gly Pro
       1250                1255                1260
Ala Gln Leu Thr Asp Glu Glu Lys Tyr Arg Asp Cys Glu Arg Phe Lys
1265                1270                1275                1280
Cys Pro Cys Pro Thr Cys Gly Thr Glu Asn Ile Tyr Asp Asn Val Phe
            1285                1290                1295
Asp Gly Ser Gly Thr Asp Met Glu Pro Ser Leu Tyr Arg Cys Ser Asn
            1300                1305                1310
Ile Asp Cys Lys Ala Ser Pro Leu Thr Phe Thr Val Gln Leu Ser Asn
       1315                1320                1325
Lys Leu Ile Met Asp Ile Arg Arg Phe Ile Lys Lys Tyr Tyr Asp Gly
       1330                1335                1340
Trp Leu Ile Cys Glu Glu Pro Thr Cys Arg Asn Arg Thr Arg His Leu
1345                1350                1355                1360
Pro Leu Gln Phe Ser Arg Thr Gly Pro Leu Cys Pro Ala Cys Met Lys
            1365                1370                1375
Ala Thr Leu Gln Pro Glu Tyr Ser Asp Lys Ser Leu Tyr Thr Gln Leu
            1380                1385                1390
```

-continued

```
Cys Phe Tyr Arg Tyr Ile Phe Asp Ala Glu Cys Ala Leu Glu Lys Leu
     1395                1400                1405

Thr Thr Asp His Glu Lys Asp Lys Leu Lys Lys Gln Phe Phe Thr Pro
 1410                1415                1420

Lys Val Leu Gln Asp Tyr Arg Lys Leu Lys Asn Thr Ala Glu Gln Phe
 1425                1430                1435                1440

Leu Ser Arg Ser Gly Tyr Ser Glu Val Asn Leu Ser Lys Leu Phe Ala
         1445                1450                1455

Gly Cys Ala Val Lys Ser
         1460

<210> SEQ ID NO 32
<211> LENGTH: 9
<212> TYPE: PRT
<213> ORGANISM: Homo sapiens

<400> SEQUENCE: 32

Val Lys Ser Pro Gln Leu Leu Asn Gln
 1               5

<210> SEQ ID NO 33
<211> LENGTH: 11
<212> TYPE: PRT
<213> ORGANISM: Homo sapiens

<400> SEQUENCE: 33

Val Lys Lys Ser Thr Ala Leu Glu Ser Ala Ser
 1               5                   10

<210> SEQ ID NO 34
<211> LENGTH: 9
<212> TYPE: PRT
<213> ORGANISM: Homo sapiens

<400> SEQUENCE: 34

Val Lys Lys Ser Thr Ala Leu Asn Gln
 1               5

<210> SEQ ID NO 35
<211> LENGTH: 5433
<212> TYPE: DNA
<213> ORGANISM: Homo sapiens

<400> SEQUENCE: 35
ggggagattc gggaccatgg cacctgtgca cggcgacgac tctctgtcag attcagggag      60
ttttgtatct tctcgagccc ggcgagaaaa aaaatcaaag aaggggcgcc aagaagccct    120
agaaagactg aaaaaggcta aagctggtga aagtataaa tatgaagtcg aggacttcac    180
aggtgtttat gaagaagttg atgaagaaca gtattcgaag ctggttcagg cacgccagga    240
tgatgactgg attgtggatg atgatggtat tggctatgtg aagatggcc gagagatttt    300 tgatgatgac cttgaagatg atgcccttga tgctgatgag aaaggaaaag atggtaaagc    360
acgcaataaa gacaagagga atgtaaagaa gctcgcagtg acaaaaccga caacattaa    420 gtcaatgttc attgcttgtg ctggaaagaa aactgcagat aaagctgtag acttgtccaa    480
ggatggtctg ctaggtgaca ttctacagga tcttaacact gagacacctc aaataactcc    540
accacctgta atgatactga agaagaaaag atccattgga gcttcaccga atcctttctc    600
tgtgcacacc gccacggcag ttccttcagg aaaaattgct tcccctgtct ccagaaagga    660
```

-continued

```
gcctccatta actcctgttc ctcttaaacg tgctgaattt gctggcgatg atgtacaggt      720
cgagagtaca gaagaagagc aggagtcagg ggcaatggag tttgaagatg gtgactttga      780
tgagcccatg gaagttgaag aggtggacct ggagcctatg gctgccaagg cttgggacaa      840
agagagtgag ccagcagagg aagtgaaaca agaggcggat tctgggaaag ggaccgtgtc      900
ctacttagga agttttctcc cggatgtctc ttgttgggac attgatcaag aaggtgatag      960
cagtttctca gtgcaagaag ttcaagtgga ttccagtcac ctcccattgg taaaaggggc     1020
agatgaggaa caagtattcc acttttattg gttggatgct tatgaggatc agtacaacca     1080
accaggtgtg gtatttctgt ttgggaaagt ttggattgaa tcagccgaga cccatgtgag     1140
ctgttgtgtc atggtgaaaa atatcgagcg aacgctttac ttccttcccc gtgaaatgaa     1200
aattgatcta aatacgggga agaaacagg aactccaatt tcaatgaagg atgtttatga     1260
ggaatttgat gagaaaatag caacaaaata taaaattatg aagttcaagt ctaagccagt     1320
ggaaaagaac tatgcttttg agatacctga tgttccagaa aaatctgagt acttggaagt     1380
taaatactcg gctgaaatgc cacagcttcc tcaagatttg aaaggagaaa cttttttctca     1440 tgtatttggg accaacacat ctagcctgga actgttcttg atgaacagaa agatcaaagg     1500
accttgttgg cttgaagtaa aaaagtccac agctcttaat cagccagtca gttggtgtaa     1560
agttgaggca atggctttga aaccagacct ggtgaatgta attaaggatg tcagtccacc     1620
accgcttgtc gtgatggctt tcagcatgaa gacaatgcag aatgcaaaga accatcaaaa     1680
tgagattatt gctatggcag ctttggtcca tcacagtttt gcattggata agcagcccc      1740 aaagcctccc tttcagtcac acttctgtgt tgtgtctaaa ccaaaggact gtatttttcc     1800
atatgctttc aaagaagtca ttgagaaaaa gaatgtgaag gttgaggttg ctgcaacaga     1860
aagaacactg ctaggttttt tccttgcaaa agttcacaaa attgatcctg atatcattgt     1920
gggtcataat atttatgggt ttgaactgga agtactactg cagagaatta atgtgtgcaa     1980
agctcctcac tggtccaaga taggtcgact gaagcgatcc aacatgccaa agcttggggg     2040
ccggagtgga tttggtgaaa gaaatgctac ctgtggtcga atgatctgtg atgtggaaat     2100
ttcagcaaag gaattgatt gttgtaaaag ctaccatctg tctgaacttg ttcagcagat     2160
tctaaaaact gaagggttg taatcccaat ggaaaatata caaatatgt acagtgaatc     2220 ttctcaactg ttatacctgt tggaacacac ctggaaagat gccaagttca ttttgcagat     2280
catgtgtgag ctaaatgttc ttccattagc attgcagatc actaacatcg ctgggaacat     2340
tatgtccagg acgctgatgg gtggacgatc cgagcgtaac gagttcttgt tgcttcatgc     2400 atttacgaa aacaactata ttgtgcctga caagcagatt ttcagaaagc ctcagcaaaa     2460
actgggagat gaagatgaag aaattgatgg agataccaat aaatacaaga aaggacgtaa     2520
gaaaggagct tatgctggag gcttggtttt ggaccccaaa gttggttttt atgataagtt     2580
cattttgctt ctggacttca acagtctata tccttccatc attcaggaat ttaacatttg     2640
ttttacaaca gtacaaagag ttgcttcaga ggcacagaaa gttacagagg atggagaaca     2700
agaacagatc cctgagttgc cagatccaag cttagaaatg ggcattttgc ccagagagat     2760
ccggaaactg gtagaacgga gaaaacaagt caaacagcta atgaaacagc aagacttaaa     2820
tccagacctt attcttcagt atgacattcg acagaaggct ttgaagctca cagcgaacag     2880
tatgtatggt tgcctgggat tttcctatag cagattttac gccaaaccac tggctgcctt     2940
ggtgacatac aaaggaaggg agattttgat gcatacgaaa gagatggtac aaaagatgaa     3000
tcttgaagtt atttatggag atacagattc aattatgata aacaccaata gcaccaatct     3060
```

-continued

```
ggaagaagta tttaagttgg gaaacaaggt aaaaagtgaa gtgaataagt tgtacaaact      3120
gcttgaaata gacattgatg gggttttcaa gtctctgcta ctgctgaaaa aaaagaagta      3180
cgctgctctg gttgttgagc caacgtcgga tgggaattat gtcaccaaac aggagctcaa      3240
aggattagat atagttagaa gagattggtg tgatcttgct aaagacactg gaaactttgt      3300
gattggccag attctttctg atcaaagccg ggacactata gtggaaaaca ttcagaagag      3360
gctgatagaa attggagaaa atgtgctaaa tggcagtgtc ccagtgagcc agtttgaaat      3420
taacaaggca ttgacaaagg atccccagga ttaccctgat aaaaaagcc tacctcatgt      3480 acatgttgcc ctctggataa attctcaagg aggcagaaag gtgaaagctg agatactgt      3540 gtcatatgtc atctgtcagg atggatcaaa cctcactgca agtcagaggg cctatgcgcc      3600
tgagcagctg cagaaacagg ataatctaac cattgacacc cagtactacc tggcccagca      3660
gatccaccca gtcgtggctc ggatctgtga accaatagac ggaattgatg ctgtcctcat      3720
tgcaacgtgg ttgggacttg accccaccca atttagagtt catcattatc ataaagatga      3780
agagaatgat gctctacttg gtggcccagc acagctcact gatgaagaga atacaggga      3840 ctgtgaaaga ttcaaatgtc catgccctac atgtggaact gagaatattt atgataatgt      3900
ctttgatggt tcgggaacag atatggagcc cagcttgtat cgttgcagta acatcgattg      3960
taaggcttca cctctgacct ttacagtaca actgagcaac aaattgatca tggacattag      4020
acgtttcatt aaaaagtact atgatggctg gttgatatgt gaagagccaa cctgtcgcaa      4080
tcgaactcgt caccttcccc ttcaattctc ccgaactggg cctctttgcc cagcctgcat      4140
gaaagctaca cttcaaccag gtattctga caagtccctg tacacccagc tgtgcttta      4200 ccggtacatt tttgatgcgg agtgtgcact ggagaaactt actaccgatc atgagaaaga      4260
taaattgaag aagcaatttt ttaccccccaa agttctgcag gactacagaa aactcaagaa      4320
cacagcagag caattcttgt cccgaagtgg ctactccgaa gtgaatctga gcaaactctt      4380
cgctggttgt gccgtgaaat cctaagggaa tcccaggagt aaccaaggag ggggtagttg      4440
aaaaatccca gcttcctctg tgcctccact ctggccctaa atgctcctcc agcatctgtt      4500
tctcccttgg gactgtgtct catgtttgtg tgaatgtaga ccaggaaagg gggctgcaaa      4560
aatgttgagt ctaatgttcg taagcatcat agaaattcct gtcttcatat taagatgtac      4620
tgctttaaaa cacaactcca gagcccctcc ccaagctccc ctccccaagc tcctgaagac      4680
ccggtttctg agggagggaa attgctactt ggattgagag tagctggaat gtaagtgacc      4740
ccaggctttg ctcagggcct ttagcctatg tcccccccac ataaagagag cttctcagag      4800
cctgactgaa gagctgacgt tttgcttttt catatgccaa ttaaacccgg tctaaatcca      4860
aatgcttctc cagccatcca ggagtggctg tccttttcag tcttgtcttt tatataggta      4920
gctgaggggg aagatttaga agccttgcac tcactaaata gattaaacag agcaggcttg      4980
tttgttgaat tgctccaaag tccaacagac acacactgag caggtgtttt acactcacat      5040 tcccttttg cccccttaaat agaaagtgca ggtaaaggtt tatacaacaa gaaagcacat      5100
tgaaaataat ttgatactct aacaatccat taacatgtgt agggggttacg gtgaggatca      5160 tgtgttgtat tcgaaaaacg gggagaggga tgcttaattg gccctcgctt gctatttttt      5220
tctcatttct tcacaatagg accgtctttg gcagcagcaa aatgtatttc agtatggcag      5280
```

```
tctttcctct cttacattat tggtaagatt atactaacaa aatgtttccc cttgtacaat    5340
tatgctgtgt ttttaaaaaa cattgacctg tgtgttttta taaaagaaaa agtatgttgt    5400
gccttcttct taagaataaa gttttctaaa ggg                                 5433
```

MUTAGENICITY SCREENING METHOD USING HUMAN DNA POLYMERASE OR CATALYTIC POLYPEPTIDE

This is a Divisional of application Ser. No. 07/792,600 filed on Nov. 15, 1991 U.S. Pat. No. 6,008,045.

FIELD OF THE INVENTION

The present invention relates to compositions and methods for template-dependent enzymatic synthesis of nucleic acid, and more specifically, replication of nucleic acid by human polymerase α. The present invention is particularly useful for screening chemotherapeutics for potential mutagenicity and carcinogenicity.

BACKGROUND

The term "chemotherapy" simply means the treatment of disease with chemical substances. The father of chemotherapy, Paul Ehrlich, imagined the perfect chemotherapeutic as a "magic bullet"; such a compound would kill an invading organism without harming the host. This target specificity is sought in all types of chemotherapeutics, including antimicrobial and anticancer agents.

Unquestionably, the greatest success with antimicrobials in terms of specificity has been with antibiotics. The antibiotic penicillin is widely known for its ability to block the synthesis of the cell wall for particular bacteria without interfering with the biochemistry of mammalian cells. What is not widely known is that penicillin is the exception rather than the rule; only a fraction of the thousands of identified antimicrobial drugs are non-toxic to humans.

Efforts to treat viral infection have been largely ineffective for precisely this reason. While a virus is essentially nothing more than nucleic acid surrounded by a lipid-protein envelope, a virus invades a host cell and uses the host cell's machinery to replicate itself. The latter characteristic makes it especially difficult to find drugs which block viral replication and yet leave intact the ability of the host cell to replicate.

Specificity has also been the major problem with anticancer agents. In the case of anticancer agents, the drug needs to distinguish between host cells that are cancerous and host cells that are not cancerous. The vast bulk of anticancer drugs are indiscriminate at this level. For this reason, only a few types of cancer are appropriate for chemotherapy. Surgery and radiation continue to be the favored types of cancer treatment.

Drug Screening

While there has been little success with viral infection and cancer, there is continued hope that drugs can be found or designed with the requisite specificity for the treatment of human afflictions. However, even if compounds can be found that do not have immediate toxicity, exhaustive screening is necessary to ensure that the selected compounds are neither carcinogens nor mutagens.

A mutation is a change in the sequence, number or nature of nucleotide bases in DNA. A certain amount of mutation is normal (and perhaps even necessary) in all organisms. A mutagen is a compound that increases the normal frequency of mutation.

One source of mutation is caused by direct modification of a normal base by a mutagen so as to alter its normal base pairing. Another type of mutation is caused by the incorporation of analogs of the normal nucleotide bases during DNA replication. Still other mutations are caused by the incorporation of additional bases or the loss of bases during replication.

Importantly, not all mutagens will result in carcinogenicity. Nonetheless, all carcinogens are mutagens.

It has proven difficult to directly measure mutagenicity of compounds in higher organisms such as mammals. Mutations are rare and it takes great numbers of organisms before they are seen. Current approaches, therefore, utilize microorganisms such as bacteria.

The most widely used mutagen/carcinogen screening assay is the Ames test. The Ames test utilizes several unique strains of *Salmonella typhimurium* that are histidine-dependent for growth and that lack the usual DNA repair enzymes. The frequency of normal mutations that render the bacteria independent of histidine (i.e., the frequency of spontaneous revertants) is low. Thus, the test can evaluate the impact of a compound on this revertant frequency.

Since some substances are not mutagenic by themselves but are converted to a mutagen by metabolic activation, the compound to be tested is mixed with the bacteria on agar plates along with a liver extract. The liver extract is needed to mimic metabolic activation in an animal. Control plates have only the bacteria and the extract.

The mixtures are allowed to incubate. Growth of bacteria (if any) is checked by counting colonies. A positive Ames test is one where the number of colonies on the plates with mixtures containing the compound significantly exceeds the number on the corresponding control plates.

When known carcinogens are screened in this manner with the Ames test, approximately ninety percent are positive. When known noncarcinogens are similarly tested, approximately ninety percent are negative.

Drawbacks to the Bacterial Model

For many compounds, the Ames test is quite adequate. These compounds (e.g., pesticides, dyes, etc.) are those thought to cause mutations by direct modification of the chemistry of a normal base. It is believed that this nucleic acid modification chemistry will be the same in the bacteria as in mammalian cells. Thus, the change in the revertant frequency of the bacteria is predictive of mutagenicity in mammals.

The Ames test is, however, not definitive for all chemotherapeutics. Indeed, it may be particularly ill-suited to test nucleotide analogs designed as antiviral and anticancer agents. These agents are designed to be incorporated in the target cell nucleic acid during replication. Unfortunately, they may also be incorporated by normal host cells during normal replication and cause subsequent mutations.

In contrast to nucleic acid modification chemistry, incorporation of nucleotide analogs occurs via the replication machinery. It is known that the bacterial replication machinery is distinctly different from that of mammalian cells. Consequently, there is a concern that there will be a class of nucleotide analogs that will not be incorporated by bacteria but that will be incorporated by normal replicating mammalian cells. These compounds would test negative by the Ames test and yet be mutagenic in mammals.

SUMMARY OF THE INVENTION

The present invention relates to compositions and methods for template-dependent enzymatic synthesis of nucleic acid, and more specifically, replication of nucleic acid by human polymerase α. The use of human DNA polymerase α is particularly appropriate for screening chemotherapeutics for potential mutagenicity and carcinogenicity. Unlike current screening approaches, the screening approach of the present invention is predictive of the mutagenicity (if any) of nucleotide analogs in mammals.

The present invention contemplates the over-expression of recombinant human DNA polymerase α that is functional, and yet free of contaminating protein typically associated with human DNA polymerase α purified by traditional biochemical isolation techniques. The expression of recombinant human DNA polymerase α of the present invention relies on the construction of a full-length cDNA. This full-length cDNA has been found to generate full-length translation products.

The present invention contemplates the use of recombinant human DNA polymerase α for the screening of chemotherapeutics for potential mutagenicity and carcinogenicity. In one embodiment, recombinant human DNA polymerase α is employed to test for incorporation of analogs of the normal nucleotide bases during DNA replication.

The present invention further contemplates the use of recombinant human DNA polymerase α to test for the binding of viral proteins. In one embodiment, the present invention contemplates co-infection of cells with two expression vectors, one vector coding for the viral protein of interest and the other vector coding for human DNA polymerase α.

It is not intended that the present invention be limited by the expression system for recombinant human DNA polymerase α. The present invention contemplates all forms and sources of expression systems.

DESCRIPTION OF THE DRAWINGS

FIG. 1 is the restriction map of the cDNA for human DNA polymerase α, showing overlapping cDNA clones (triangles designate the locations of the frame-shift mutations. In addition, this figure shows the nucleotide sequences for the frameshift mutations in polymerase α cDNA clones E1–19 (SEQ ID NO: 20), E-12 (SEQ ID NO:21) and BC2# (SEQ ID NO:26) at nucleotide position 1336. This figure also shows the nucleotide sequences and the corresponding amino acid sequences for EMBO cDNA clone (SEQ ID NOS: 24, 34), E1-12 (SEQ ID NOS: 22, 33) and E1-19 (SEQ ID NOS: 23, 32) frameshift mutations at nucleotide positions 1519–1538. The E1-14b8 missense mutation at nucleotide position 2526 is also shown.).

DESCRIPTION OF THE INVENTION

Figure 2:
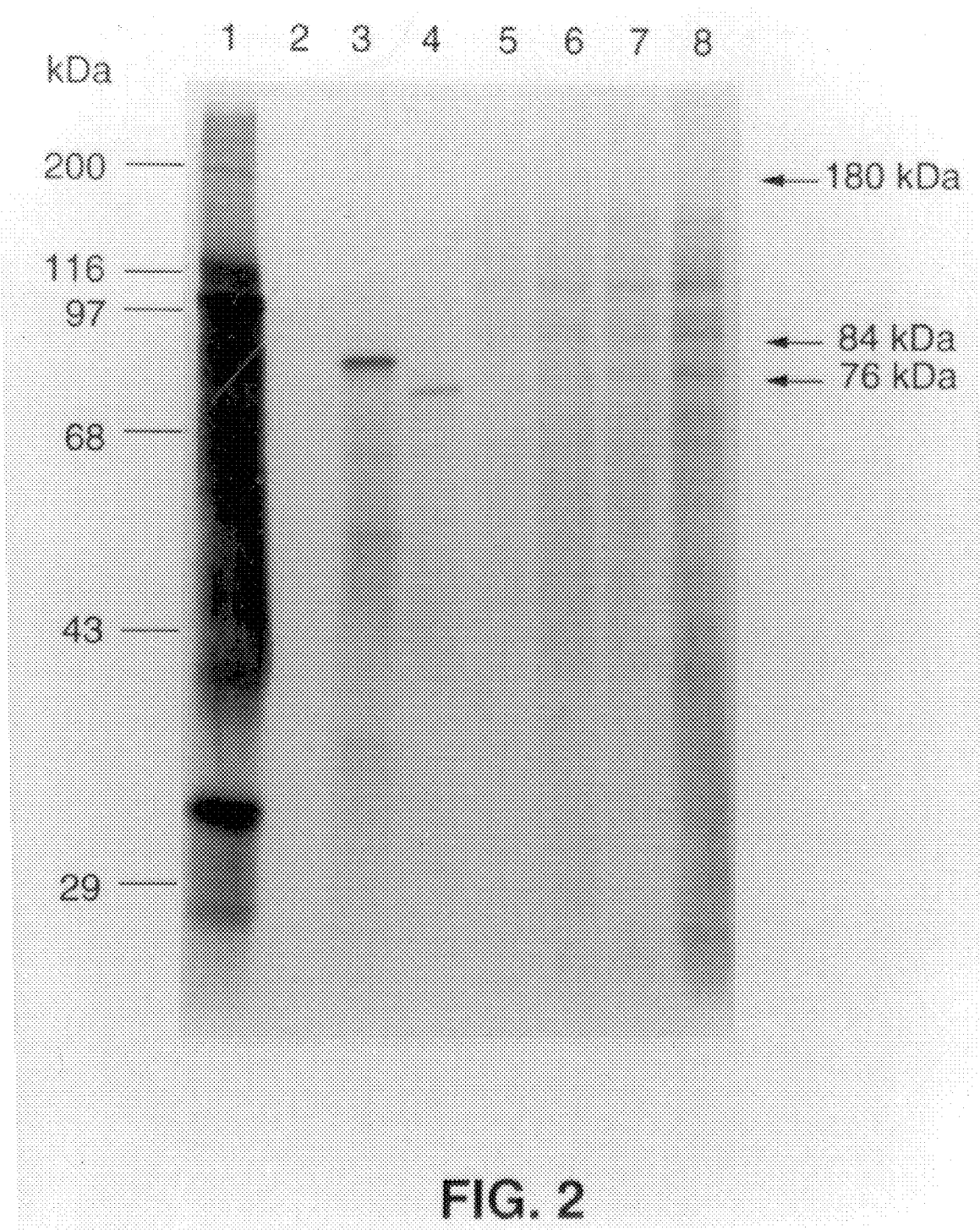
FIG. 2 is a photograph of an autoradiograph, following in vitro translations used to confirm the correct sequence of the full-length cDNA for human DNA polymerase α.

The present invention relates to compositions and methods for template-dependent enzymatic synthesis of nucleic acid. More specifically, the present invention relates to replication of nucleic acid by human polymerase α.

It is believed that eukaryotic DNA replication requires at least two DNA polymerases, α and δ, for the lagging and leading strand synthesis, respectively. See B. Stillman, Ann. Rev. Cell Biol. 5:197 (1989). M. D. Challberg and T. J. Kelly, Ann. Rev. Biochem. 58:671 (1989). DNA polymerase α/primase complex is responsible for the synthesis of the nascent DNA fragment during initiation of DNA replication and for lagging strand DNA synthesis during elongation. Evidence from several laboratories suggests that interactions between DNA polymerase α and other replication proteins are highly stringent and species specific. See T. Tsurimoto et al., Nature 346:534 (1990).

Studies of the structure and biological function of DNA polymerase α have been problematic due to its low abundance in cells and susceptibility to proteolysis during purification. Nonetheless, development of immunoaffinity and biochemical purification protocols in recent years has allowed the demonstration that polymerase α activity purified from a wide phylogenetic range of species contains a similar set of constituent subunit components. The enzyme complex is made up of a cluster of large phosphopolypeptides of predominantly 165 to 180 kDa with catalytic function, a 70 kDa phosphoprotein of unknown function, and two polypeptides, 55 and 49 kDa, containing the primase activity. This four subunit component containing polymerase α and primase activities has been designated polymerase α/primase complex. T. Wang, Ann Rev. Biochem. 60:513 (1991). Peptide mapping of the p180 and p165 subunits indicate that they are derivatives of the same polypeptide. S. W. Wong et al., J. Biol. Chem. 261:7958 (1986).

The present disclosure describes the isolation of the correct, full-length cDNA of the catalytic polypeptide of human DNA polymerase α (SEQ ID NO:1). The full length human cDNA has been constructed to be functionally over-expressed in a baculovirus transfer vector for expression in insect cells. However, it also is constructed to be functionally over-expressed in monkey COS7 cells and in yeast.

Indeed, it is not intended that the present invention be limited by the expression system for recombinant human DNA polymerase α. The present invention contemplates all forms and sources of expression systems.

Importantly, the human DNA polymerase α catalytic polypeptide has been functionally over-expressed at >1000 fold higher levels than that found in cultured normal human cells. The recombinant polymerase α protein is translated from its natural translation start codon producing a protein of 180 kDa, identical in size to that isolated from cultured human cells. This recombinant polymerase α, immunopurified as a single polypeptide, is phosphorylated and reactive to a panel of monoclonal antibodies directed against the native polymerase α/primase complex and to polyclonal antisera against N- and C-terminal peptides of the polymerase α catalytic polypeptide. The single subunit recombinant polymerase α has no detectable 3'-5' exonuclease activity. The $k_M$ for primer-template and dNTP, reactivity to inhibitors, thermosensitivity, and DNA synthetic processivity and fidelity of the recombinant polymerase α are identical to that observed with the four subunit polymerase α/primase complex immunopurified from cultured human cells.

The present invention contemplates using human polymerase α for template-dependent enzymatic synthesis of nucleic acid, and more specifically, for replication of nucleic acid. The present invention is useful for screening chemotherapeutics for potential mutagenicity and carcinogenicity. As noted above, one type of mutation is caused by the incorporation of analogs of the normal nucleotide bases during DNA replication. The present invention is particularly useful for screening chemotherapeutics that are analogs of the normal nucleotide bases.

The present invention further contemplates the use of recombinant human DNA polymerase α to test for the binding of viral proteins. In one embodiment, the present invention contemplates co-infection of cells with two expression vectors, one vector coding for the viral protein of interest and the other vector coding for human DNA polymerase α.

DETAILED DESCRIPTION OF THE INVENTION

The detailed description of the invention is divided into seven major sections: I) cDNA Construction, II) Protein Expression, III) Protein Purification and Characterization, IV) Template-Dependent Enzymatic Synthesis, V) Chemotherapeutic Screening, VI) Drug Design and VII) Viral Protein Binding.

I. cDNA CONSTRUCTION

Construction of cDNA was performed as generally described by Maniatis et al., Molecular CLoning. A Laboratory Manual, (Cold Spring Harbor Press, N.Y. 1982). Essentially, this involved a) biochemical isolation of the polymerase, b) peptide sequencing, c) probe design, d) preparation of a cDNA library, e) screening of the library with the probes, f) isolation of the positive clone(s), and g) sequencing of the cDNA.

Biochemical Isolation. Biochemical isolation of human polymerase α is well-known. See e.g., F. J. Bollum, J. Biol. Chem. 235:2399 (1960). M. Mechali et al., J. Biol. Chem. 255:2114 (1980). L. S. Kaguni et al., Proc. Natl. Acad. Sci. USA 80:2221 (1983). L. Chang et al., J. Biol. Chem. 259:14679 (1984). P. Plevani et al., J. Biol. Chem. 260:7102 (1985). F. Grosse and G. Krauss, J. Biol. Chem. 260:1881 (1985). S. W. Wong et al., J. Biol. Chem. 261:7958 (1986). R. Lehman and L. S. Kaguni, J. Biol. Chem. 264:4265 (1989). However, progress in understanding the structure and properties of the native enzyme has been severely hindered by the low abundance of the enzyme, the apparent complexity and heterogeneity of the polymerase activity in impure fractions, and the arduous purification schemes that have resulted in polymerase inactivation.

In this case, biochemical isolation was as generally described by T. Wang et al., J. Biol. Chem. 259:1854 (1984) and S. W. Wong et al., J. Biol. Chem. 261:7958 (1986). The KB cell line was used; this is a human epidermoid carcinoma cell line available from the American Type Culture Collection (ATCC) (Rockville, Md.). The isolation of human DNA polymerase α catalytic polypeptides from this cell line proceeded as follows. DNA polymerase α antigen polypeptides from six, 18 liter cultures of human KB cells ($3.5 \times 10^5$ cells/ml) were purified with a monoclonal IgG-Sepharose 4B column. The monoclonal, SJK287, was raised against a biochemically-purified, catalytically-active polymerase preparation. See S. Tanaka et al., J. Biol. CHem 257:8386 (1982). The polypeptides were suspended in 0.36 M Tris-Hcl, pH 8.6, 3.3 mM EDTA, 8 M urea and then reduced for 3 h at 37° C. under $N_2$ with 10 mM dithiothreitol. The reduced polypeptides were alkylated with 22 mM iodoacetic acid at 4° C. for 1 h and dialyzed in 50 mM $NH_4HCO_3$, 0.01% SDS. The dialyzed, reduced and alkylated DNA polymerase α protein was lyophilized, resuspended in 100 mM $NaPO_4$, pH 6.5, and 0.1% SDS and heated at 75° C. for 10 min. These polypeptides were then purified by HPLC through two coupled gel permeation columns (TSK 3000, 7.5×300 mm) in 100 mM $NaPO_4$, pH 6.5, and 0.1% SDS at a flow rate of 0.5 ml/min. The absorbance of the eluate was monitored at 280 nm. Fractions containing the 180–140 kd DNA polymerase α catalytic polypeptides were dialyzed in 50 mM $NH_4HCO_3$ containing 0.01% SDS and lyophilized.

Peptide sequencing. Peptide sequence analysis was performed as follows. Human DNA polymerase α catalytic polypeptides (500 pmol), isolated as described above, were resuspended in $H_2O$ and ethanol-precipitated twice to remove excess SDS from the samples. The polypeptides were then resuspended in 0.1 M $NH_4HCO_3$, 10 mM $CaCl_2$ and digested with 2 μg of TPCK treated trypsin at room temperature for 20 h. The trypsin digested peptides were first separated on an Aquapore RP300 (2.1×220 mm, Brownlee Lab) HPLC column equilibrated in 0.1% trifluoroacetic acid. A linear gradient from 0–60% acetonitrile was run over 45 min. at 0.2 ml/min. Absorbance at 220 nm was monitored by Spectraflow 755 Variable Wavelength detector. Selected peptides peaks were further purified by an RP300 (1×100 mm) column equilibrated in 50 mM ammonium acetate, pH 6.5. A linear gradient of 0–75% acetonitrile was run over 30 min at 0.08 ml/min. and absorbance monitored at 215 nm. Each of the separated peptides was subjected to automated Edman degradation performed on a model 470A gas phase sequencer with on-line PTH amino acid analysis (Model 120A) (Hunkapiller et al., 1983).

The amino acid sequences of seven peptides (hereinafter designated T9, T19, T23, T24, T25, T264, and T265) were determined as described in Table 1 of S. W. Wong et al., The EMBO Journal 7:37 (1988). In all, the sequences of 85 amino acids were established.

Probe design. Using the amino acid data, single long anti-sense oligonucleotide probes SEQ ID NOS: 6–19 were designed according to R. Lathe, J. Mol. Biol. 183:1 (1985). The probes were synthesized on an Applied Biosystems model 380A oligonucleotide synthesizer at DNAX Research Institute (the degenerate code is as follows: 3
= C/G, 4 = A/T, 5 = A/G, 6 = C/T, 7 = A/C/G/T, 8 = A/C/T,
9-A/C):
Polalpha #19A
Position: peptide T19
Sequence: GCTGCCTATGCTGGCGGCCTGGTGCTGGACCCAAG Polalpha #19B
Position: peptide T19
Sequence: CTTGGGGTCCAGCACCAGGCCGCCAGCATAGGCAGC Polalpha #23A
Position: peptide T23
Sequence: CTTCACCTCCAGCCAGGTGGGGCC Polalpha 25
Position: peptide T25
Sequence: TA6AT8TT6GA6GC7GA Polalpha 25
Position: peptide T25
Sequence: TACATCTTTGATGCTGAGACAGCCCTGGAGAAG Polalpha 25A
Position: peptide T25
Sequence: CTTCTCCAGGGCTGTCTCAGCATCAAAGATGTA Polalpha 26A
Position: peptide T26
Sequence: GTAGAACACCTGCTGCAGCAGCTCATC Polalpha #23AI
Position: peptide T23
Sequence: ITTIACITCIA5CCAIGTIGGICC Polalpha #24AI
Position: peptide T24
Sequence: ITTITCIGGIACITCIGGIATITCIAAIGCITAITT Polalpha #25AI
Position: peptide T25
Sequence: ITTITCIA5IGCIGTITCIGCITCIAAIATITA Polalpha #26AI
Position: peptide T26
Sequence: ITTITCIGGIACITCIGGIATITCIAAIGCITAITT P264a
Position: peptide T264
Sequence: AC7GG7AA6TT6GT P265
Position: peptide T265
Sequence: GATCTGCTGGGCCAGGTAGTACTGGG
          TGTCAATGGTCAGGTTGGTCTG T-26-4
Position: peptide T264
CCGGGACTGGTCAGACAGGATCTGGCCAATCACAAAGTTGCCTGT These probes SEQ ID NOS:6–19 were used to screen cDNA libraries for positive clones.

Preparation of a cDNA library. Ninety µg of poly(A)+ mRNA from early mid-log human KB cells was heated at 65° C. for 1 min. and loaded onto a 5.3 ml sucrose gradient of 5–25% containing 100 mM NaCl, 10 mM Tris-HCl, pH 7.4, 1 mM EDTA and 0.1% SDS. Centrifugation was carried out at 52 300 g for 25 h at 5° C. and fractionated into 20 fractions. mRNA samples of each fraction were precipitated by ethanol and resuspended into 5 µl of $H_2O$. Ten percent of each fraction was used to estimate the size by reverse transcription, followed by analyzing the product on a 1% alkaline agarose gel. Fractions containing mRNA of >4 kb were used to construct a cDNA library in pcD vector as described. See H. Okayama and P. Berg, Mol. Cell. Biol. 2:161 (1982) and 3:280 (1983). An aliquot of this library containing $1 \times 10^5$ recombinants was used for the screening with oligonucleotide probes.

Screening of the library. The hybridization conditions used for screening were 6×SSPE, 0.1% SDS 100 µg/ml *E. coli* tRNA. Washing conditions were 2×SSPE, 0.1% SDS. Temperature of hybridization and washing depended on the individual oligonucleotide probe used. Stringency of hybridization and washing of each individual oligonucleotide probe was based on $T_m$ (melting temperature) and $T_w$ (washing temperature) values estimated at >85% probe-target homology. See R. Lathe, J. Mol. Biol. 183:1 (1985).

Isolation of the positive clones. Screening of $1 \times 10^5$ colonies of this size-selected library yielded a single distinct positive clone designated as pcD-KBpolα, which hybridizes with oligo-deoxynucleotide probes, corresponding to peptides T264 SEQ ID NO:18, T265 SEQ ID NOS:17–19 and T25 SEQ ID NOS:9–11 (see above).

Sequencing of the cDNA. Preliminary sequence analysis of pcD-KBpolα indicated that it contained a 2893-bp cDNA insert with an open reading frame of 1865 bp terminated by a stop codon and followed by a 1028-bp non-coding region. See S. W. Wong et al., The EMBO Journal 7:37 (1988). In this 1865-bp coding sequence there are four regions of deduced amino acid sequences that appeared perfectly homologous to the previously determined amino acid sequences, T264, T265, T25 and T9. The 3'-non-translated region contains several in-frame stop codons, and the consensus polyadenylation signal AATAAA (N. J. Proudfoot and G. G. Brownlee, Nature 263:211 1976) 13 nucleotides upstream from the polyadenylation tail. This strongly suggested that pcD-KBpolα contained the 3'-end of the cDNA for human DNA polymerase α.

To extend this truncated cDNA clone the 5'-most restriction fragment of pcD-KBpolα, PstI/HindIII, was used to screen 2×10$_6$ phage of a human pre-B cell cDNA library (E1 library) constructed in λgt10. See Cleary et al., Cell 47:19 (1986). The very 5'-terminal restriction fragments of the newly extended cDNA clones were used to further screen the E1 library. Some of the clones were sequenced in both directions as described (R. M. K. Dale et al., Plasmid 13:31 1985).

II. PROTEIN EXPRESSION

Initial attempts to functionally express the full length cDNA clone of the human DNA polymerase α catalytic subunit SEQ ID NO:1 resulted in truncated translation products. Resequencing of the five overlapping cDNA clones in conjunction with in vitro translation analysis revealed two frame-shift mutations and two missense mutations in the two previously isolated cDNA clones, E1–19 SEQ ID NO:20 and E1–12, SEQ ID NO:21 that contain the 5' end of the cDNA sequence. FIG. 1 is the restriction map of the cDNA for human DNA polymerase α, showing overlapping cDNA clones (triangles designate the locations of the frame-shift mutations).

The deletion frame-shift in E1–19 shifted translation by +1 at the nucleotide 1336 and caused termination of the protein after translation of nucleotides 1419–1421 (TGA). FIG. 2 is a photograph of an autoradiograph, following in vitro translations used to confirm the correct sequence of the full-length cDNA for human DNA polymerase α SEQ ID NO: 1. Translation products were labelled with [35S]-L-methionine and subjected to electrophoresis (SDS-PAGE, 10% gels) followed by autoradiography for four days. Positive and negative controls are in Lanes 1 and 2, respectively. Lane 4 shows the translation (in vitro translations) of the cDNA containing the E1–19 cDNA clone SEQ ID NO: 20, producing an apparent polypeptide of 76,000 daltons in the rabbit reticulocyte lysate system (Promega Corp., Madison, Wisconsin). This region of the E1–19 cDNA clone SEQ ID NO:20 was not sequenced previously (see S. W. Wong et al., The EMBO Journal 7:37 1988) and thus went undetected.

The insertion frame-shift in the E1–12 (SEQ ID NO:22) clone when spliced to the first half of the E1–19 (SEQ ID NO:23)clone shifted translation by –1 at the stretch of 6 A's causing termination in protein synthesis after nucleotides 1558–1560 (TAA). This gave an apparent translation product in vitro of 84,000 daltons (see lane 3 of FIG. 2). Previously (see S. W. Wong et al., The EMBO Journal 7:37 1988) the outlined G was dropped from the sequence which shifted the predicted reading frame back in frame (SEQ ID NO:24). In this area of the sequence only the E1–12 clone (SEQ ID NO:22) was sequenced so there was no comparison to the correct sequence found in the E1–19 clone (SEQ ID NO:23).

To correct the frame-shifts it was easier to change the mutation in the E1–19 (SEQ ID NOS:20,23) clone and use that clone with E1–14a to reconstruct the full length cDNA. The alternative would have been to splice the first third of the E1–19 (SEQ ID NOS:20,23) clone with a small portion of E1–12 (SEQ ID NOS:21,22) covering the E1–19 (SEQ ID NOS:20,23) mutation, and then splicing the last part of E1–19 (SEQ ID NOS:20,23) to cover the E1–12 (SEQ ID NOS:21,22) mutation. Because of the close proximity of these mutations it was much easier to change the E1–19 (SEQ ID NOS:20,23) mutation by site-directed mutagenesis using a custom designed oligo (hereinafter "BC2"(SEQ ID NO:25): 5'-G AAC TAT GCA TTC GAG ATA CCT GA-3'. BC2 (SEQ ID NO:25) also contains an NsiI restriction endonuclease site for monitoring the presence of the mutation throughout the subcloning steps.

Briefly, the BC2 oligo (SEQ ID NO: 25) was annealed to single stranded M13 phage uracil rich (SEQ ID NO:25) DNA containing the 1505 bp PstI-PstI fragment of E1–19 and extended by T4 DNA polymerase and selected in JM101 *E. coli*. The correct mutation was confirmed by DNA sequencing and reconstructed into the E1–19 cDNA clone (SEQ ID NOS:20,23). The full length cDNA clone was reconstructed from the corrected E1–19 clone and the E1–14a clone by splicing them together at the SalI site at nucleotide position 2004. Lanes 5 and 6 of FIG. 2 show the products from translation of the full length cDNA with the corrected E1–19 cDNA clone. The same translations were performed in lanes 7 and 8 of FIG. 2, but these were performed in the presence of caffeine to stimulate full length translation. Note the production of a band at 180 kDa (top arrow).

Figure 3A:
FIG. 3 sets forth the correct nucleotide sequence (both (SEQ NO:1) which encompasses a coding region corresponding to nucleotide positions 1–4440, and (SEQ ID NO:35) which encompasses a coding region plus a non-coding region corresponding to nucleotide positions 1–5433) and amino acid sequence SEQ ID NO:31 (corresponding to the gene product generated from the nucleic acids set out in (SEQ ID NO:1) which encompass a coding region corresponding to nucleotide positions 1–4440) of the human DNA polymerase α catalytic polypeptide (newly corrected sequences are boxed in).

As a result of these findings and according to the sequence data of the panel of overlapping cDNA clones, the amino acid sequence of the human DNA polymerase α (SEQ ID NO:31) was corrected as follows: the previously reported amino acids KSTA from amino acid residue position 499 to 503 are changed to SPQL, and amino acid residue G at position 837 have been corrected to A by site-directed mutagenesis to give a continuous open reading frame of 1462 amino acids. FIG. 3 sets forth the correct nucleotide sequence associated with (SEQ ID NO:1) which encompasses a coding region, corresponding to nucleotide positions 1–4440 and amino acid sequence (SEQ ID NO:31) of the human DNA polymerase α catalytic polypeptide (newly corrected sequences are boxed in).

In one embodiment, protein expression is carried out using a recombinant baculovirus expression vector, capable of expression in a host insect cell. Such systems are known to the art. For example, G. E. Smith and M. D. Summers, U.S. Pat. Nos. 4,745,051 and 4,879,236, hereby incorporated by reference, describe a method wherein baculovirus DNA is cleaved to produce a DNA fragment comprising a polyhedrin gene, including a polyhedrin promoter. A recombinant shuttle vector is prepared by inserting the fragment into a cloning vehicle and thereafter inserting a selected gene into the modified cloning vehicle such that it is under the transcriptional control of the polyhedrin promoter. The recombinant shuttle vector is contacted with a baculovirus DNA so as to effect recombination and incorporation of the selected gene into the baculovirus genome. The resultant recombinant baculovirus is then used to infect susceptible insects or cultured insect cells and the protein product from the incorporated selected gene is produced from the infection.

Many recombinant baculovirus expression vectors and shuttle vectors are on deposit at the ATCC or the Agricultural Research Culture Collection (Peoria, Ill.).

In this case, the corrected full length cDNA insert was subcloned into the pBlueBac transfer vector (see J. Vialard et al., J. Virology 64:37 1990) under the polyhedron promoter and cotransfected into Spodoptera frugiperda cells ("Sf9 cells") with wild type baculovirus DNA. (Sf9 cells were either grown in T150 tissue culture flasks in TNM-PH media or as suspension cultures in EX-CELL 401 (JRH Biosciences) in shaker flasks.) The advantage of selecting the pBlueBac transfer vector (commercially available from Invitrogen Corp., San Diego, Calif.) is the coexpression of the β-galactosidase protein from the ETL promoter allowing easy selection of recombinant baculoviral plaques in the presence of X-gal.

Figure 4:
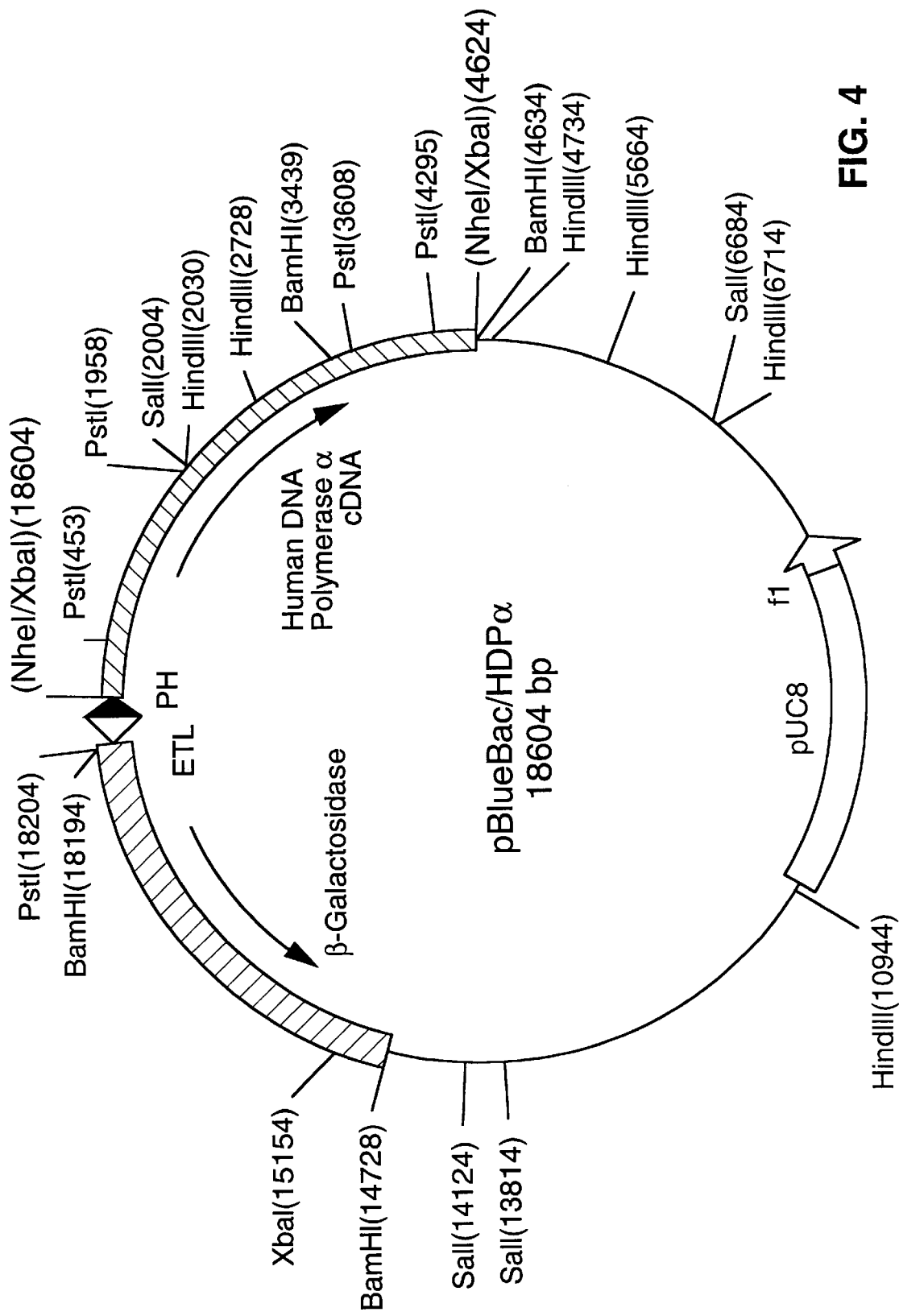
FIG. 4 schematically shows the pBlueBac/HDPα expression system.

To construct the pBlueBac transfer vector, part of the E1–19 cDNA clone was first subcloned into M13mp19 followed by site-directed mutagenesis (as noted above) to correct a frame-shift mutation. This insert was re-sequenced and ligated into E1–19 in the pUC18 vector. The full length cDNA was constructed in a pT7-7 vector (see S. Tabor and C. C. Richardson, Proc. Natl. Acad. Sci. USA 82:1074 1985) by ligation of the corrected E1–19 clone with E1–14a at the unique SalI site. The 5' NcoI site of E1–19 at the initiation ATG codon was filled in using Klenow fragment and ligated to EcoR1 linkers for insertion into the pT7-7 vector. This clone, designated pT7/HDPα, was restricted with EcoRI and filled in with Klenow. This DNA was then digested with DraI to remove most of the 3' untranslated region, and ligated with XbaI linker followed by subsequent restriction with XbaI and ligated into the unique NheI site in the pBlueBac transfer vector. The 5' end manipulations and site-directed changes of the frame-shift error in E1–19 were confirmed by dideoxy sequencing. The resulting construct was named pBlueBac/HDPα (see FIG. 4). This pBlueBac/HDPα transfer vector was then co-transfected with wild type baculovirus DNA into Sf9 cells by $CaPo_4$ transfection as described by M. Summers and G. E. Smith, Bulletin No. 1555, Texas Agriculture Experimentation Station (College Station, Tex.) (1988). Recombinant AcHDPα baculovirus was detected by X-gal in agarose overlays. A second recombinant virus was made by ligating the EcoRI-DraI fragment containing the full length cDNA from pT7/HDPα plasmid into EcoRI-SmaI digested pVL1392 transfer vector. This plasmid, pVL1392/HDPα was also co-transfected with wild type baculovirus DNA into Sf9 cells. The resulting recombinant virus, 1392α, was detected by staining with neutral red in agarose overlays. A control recombinant baculovirus, AcβGal, expressing the E. coli β-galactosidase protein was also made using the pAc360βGal transfer plasmid.

Ten occlusion minus blue viral plaques were plaque purified and screened for the presence of human DNA polymerase α by immunoblot analysis using two polyclonal antisera, DPN and DPC, specific for peptide sequences at the N- and the C-terminals of the human DNA polymerase α catalytic polypeptide (SEQ ID NO:31). See K. Hsi et al., Nucleic Acids Res. 18:6231 (1990). After four rounds of plaque purification, 7 of the plaque purified viruses expressed the human polymerase α. The resulting recombinant virus, named AcHDPα, expresses the full length recombinant human DNA polymerase α catalytic subunit from its natural ATG start codon under control of the polyhedron promoter. In addition, the full length human DNA polymerase α cDNA (SEQ ID NO:1) was inserted into the pVL1392 transfer vector and recombinant virus isolated after co-transfection into Sf9 cells. This virus, 1392α, also expresses equivalent amounts of functional recombinant human polymerase α as does the AcHDPα virus.

The level of expression and solubility of recombinant DNA polymerase α in Sf9 insect cells has been analyzed. The AcHDPα baculovirus infected Sf9 cells were harvested every 12 hours after infection and analyzed for the expression of human polymerase α protein by SDS-PAGE (FIG. 5A, 5B, 5C, 5D, and 5E) and for enzymatic activity (FIG. 5F) by polymerase assays. The SDS gels were stained by Coomassie Blue (FIGS. 5A, 5C to 5E). The presence of human DNA polymerase α was verified by immunoblot analysis (FIG. 5B) with serum antibodies directed against the N- or the C-terminal peptides of human DNA polymerase α catalytic polypeptide named DPN and DPC, respectively.

In FIGS. 5A–E, lanes 0, 12, 24, 36, 48, 60, 72, and 84, represent the hours of cell harvest post-infection. FIG. 5 is a Coomassie stained gels of whole cell lysates from $3\times10^5$ Sf9 cells. The arrows indicate the expressed intact 180 kDa recombinant polymerase α protein which appears to be the most abundant protein expressed. A second most abundant polypeptide expressed is of 140 kDa. Several proteins in minor quantity ranged from 160 to 105 kDa appeared after 36 to 84 hours post-infection are proteolytically degraded forms of the expressed recombinant polymerase.

Figure 5A:
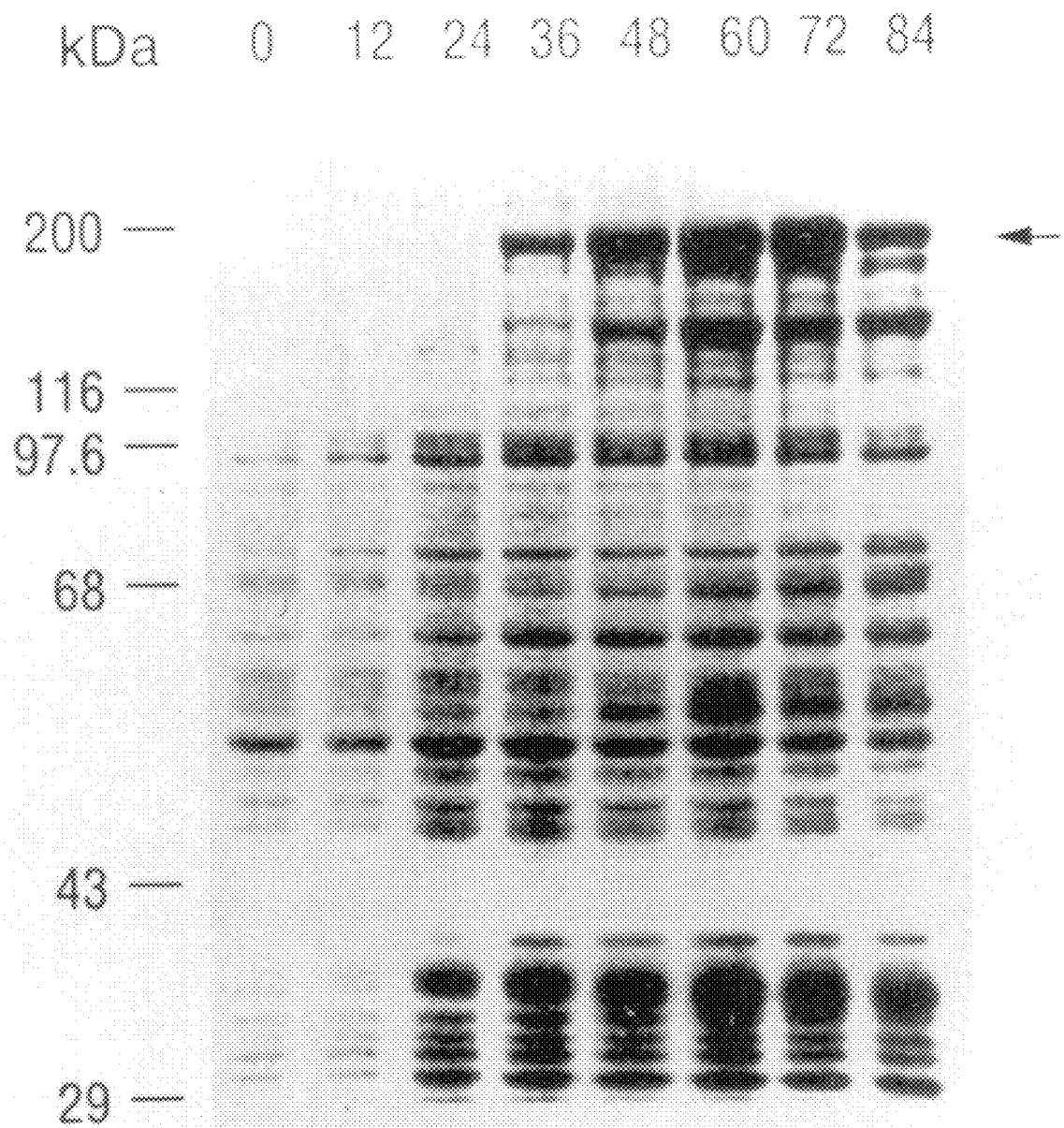
FIGS. 5A, 5C, 5D and 5E are photographs of Coomassie-stained gels following electrophoresis (SDS-PAGE).
Figure 5B:
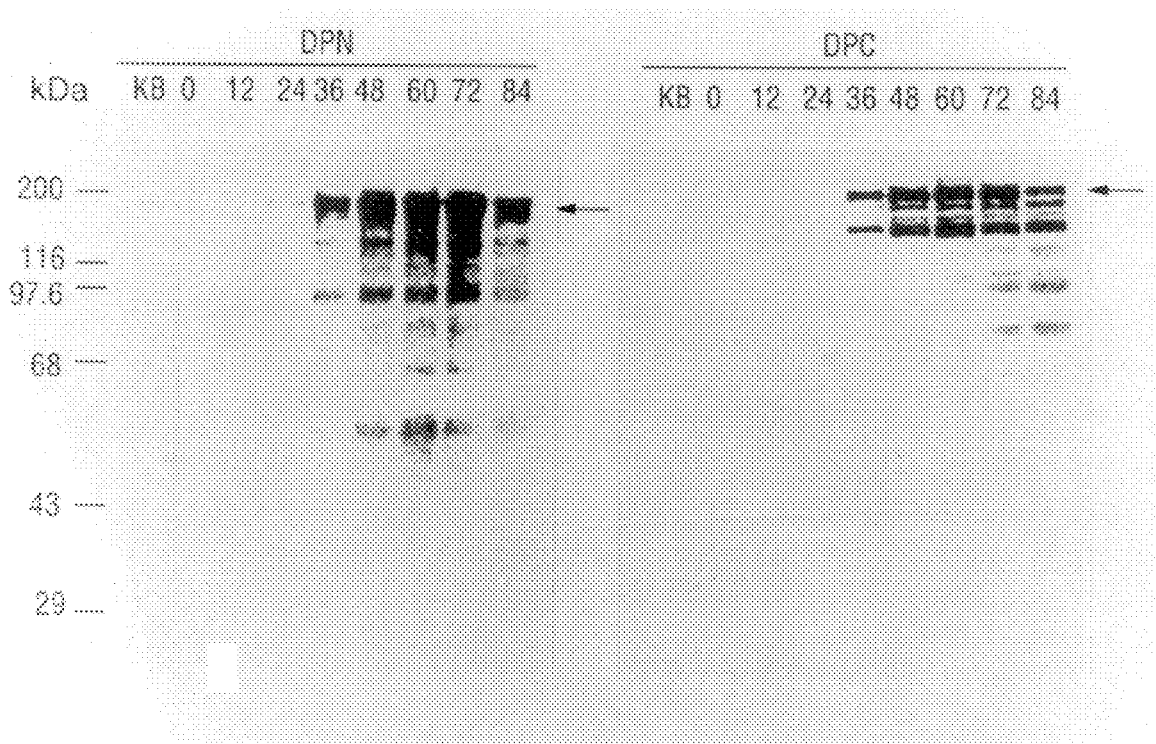
FIG. 5B is an immunoblot.

FIG. 5B is an immunoblot of the whole cells lysates shown in FIG. 5A equivalent to $3\times10^4$ cells, along with polymerase α isolated from human "KB" cells used as standard for comparison by the antisera, DPN and DPC. DPN detects the intact 180 kDa recombinant human polymerase α and also detects several proteolytic species of the recombinant human polymerase α protein of 140, 90, and 50 kDa. DPC detects the intact 180 kDa recombinant protein and proteins of 160 and 140 kDa, and several minor proteolytic species ranged from 105 to 60 kDa.

Figure 5C:
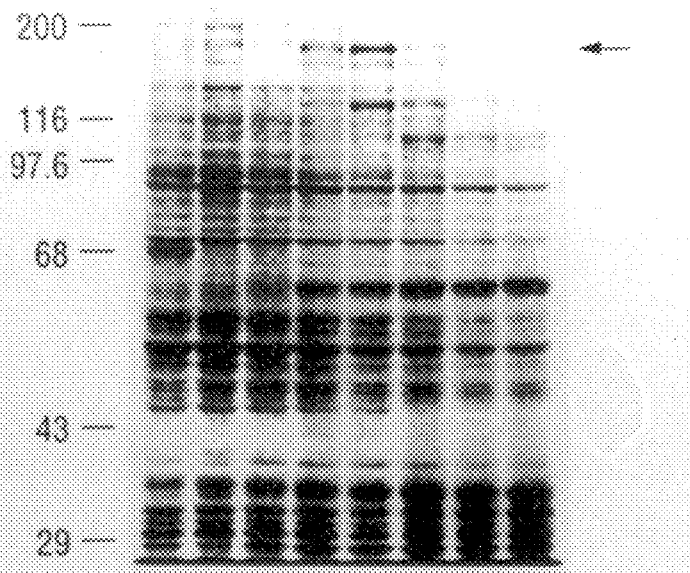

FIG. 5C is a gel showing the electrophoresis of 100 µg protein from the soluble cell lysates which are equivalent to the amount of protein from $5\times10^5$ Sf9 cells. The accumulation of a protein of ~105 kDa after 60 hr post-infection detected by neither DPN nor DPC are possible proteolytic degraded recombinant human polymerase α from both the N- and C-termini.

Figure 5D:
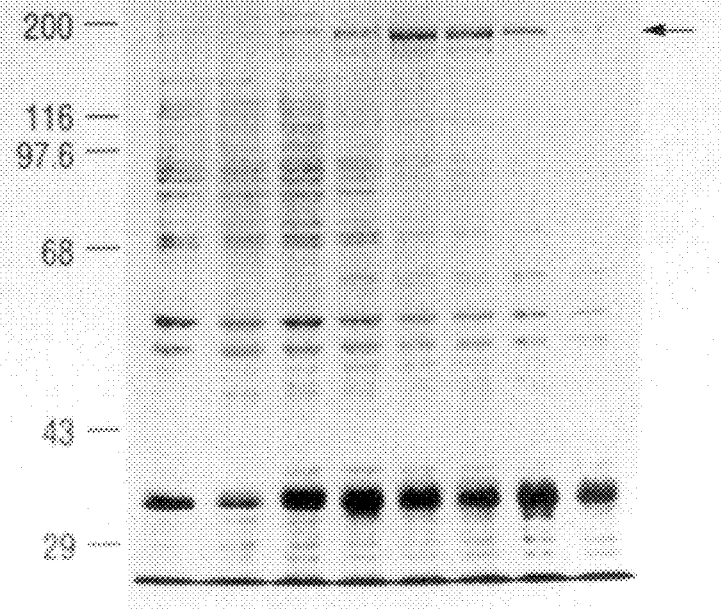
Figure 5E:
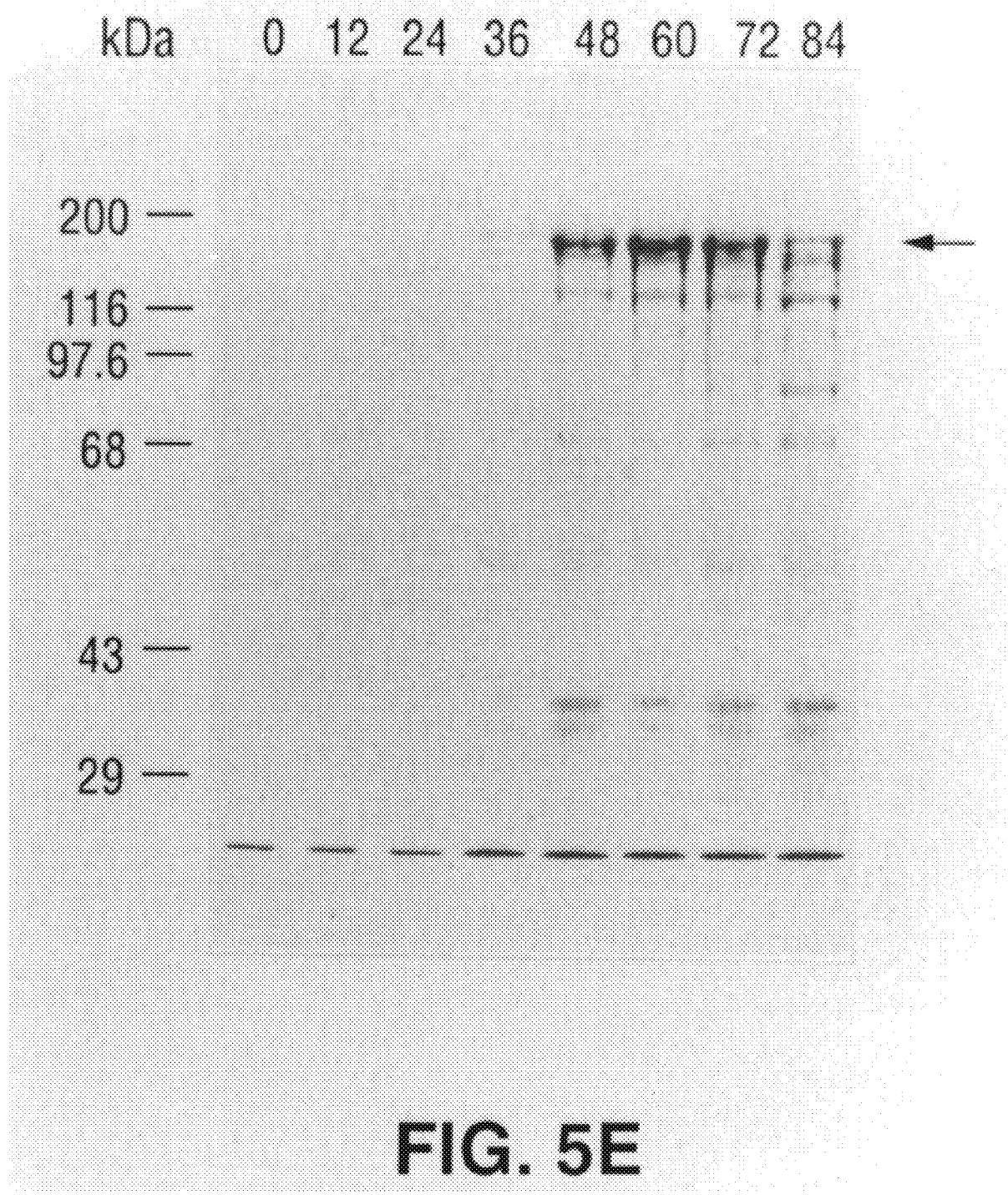

FIG. 5D is a gel showing the electrophoresis of polymerase α resolubilized from a high salt extraction. Fifty (50) µg of protein was loaded onto the gel which is equivalent to the amount of protein resolubilized from $1.6\times10^6$ cells. FIG. 5E is a Coomassie stained gel of the insoluble polymerase pellet from $1.5\times10^6$ cells.

Figure 5F:
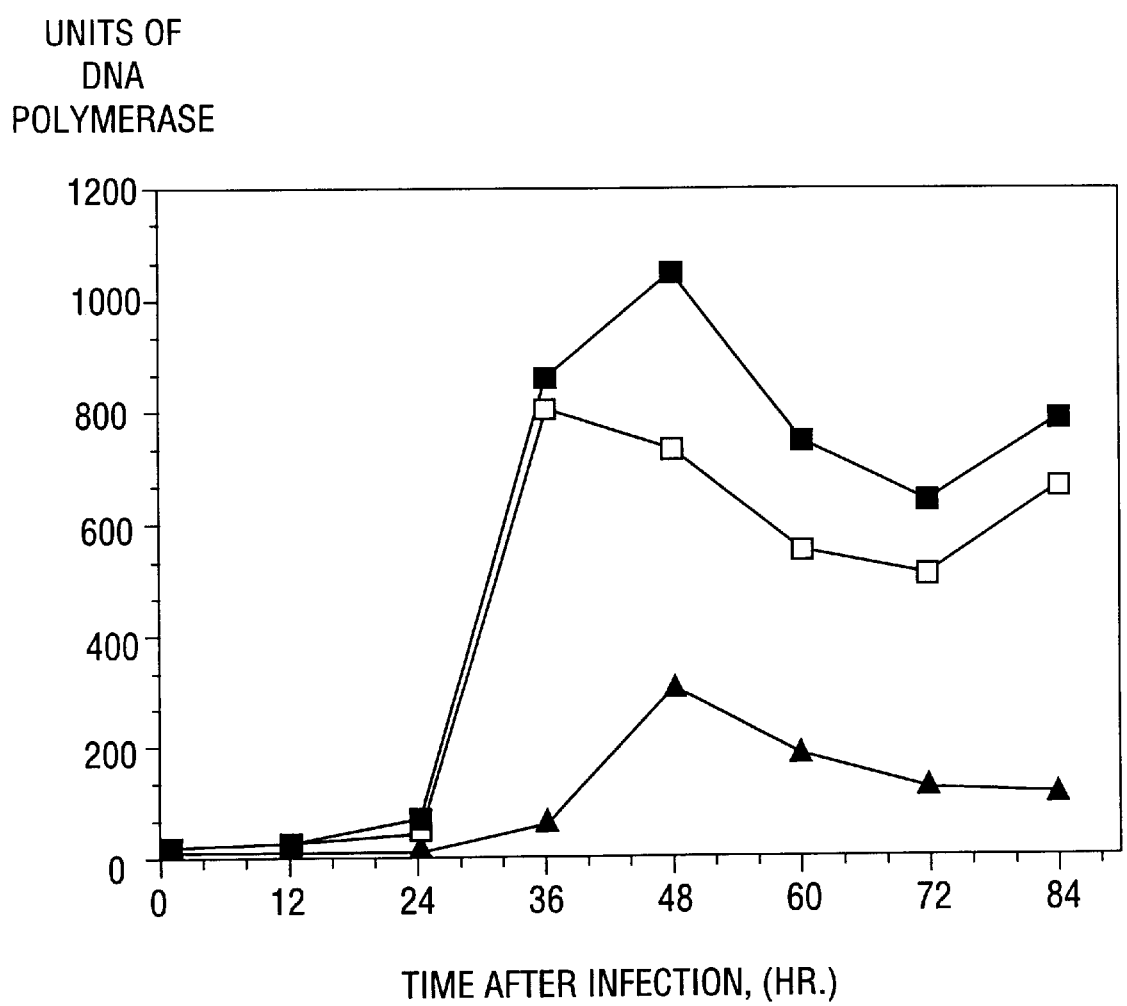
FIG. 5F schematically shows the enzymatic activity by polymerase assays.

FIG. 5F shows the total DNA polymerase units recovered in the soluble and high salt resolubilized lysates from each time point. (-□-), activity from the soluble lysates; (-▲-), activity from the resolubilized lysates by high salt extraction; (-■-), the sum total activities in the soluble and the high salt resolubilized lysates.

In general, the data shows that expression of recombinant human polymerase α can be detected in whole cell extracts as early as 24 hours after infection with AcHDPα and reaches a maximum level of expression between 48 and 60 hours post-infection (FIG. 5A, 5B and 5F). Therefore, the optimal time for isolation of enzymatically active recombinant polymerase α therefore is 48 hours when Sf9 cells are infected with AcHDPα at a multiplicity of infection (M.O.I.) of 10.

The amount of recombinant polymerase α protein expressed in insect cells was quantitated by densitometric analysis of Coomassie blue stained gels. It is expressed at a level of approximately 12% of the total cellular protein. The amount of soluble and enzymatically active recombinant human polymerase α obtained is dependent on the time of harvest as well as on the method used for cell lysis. Cells were lysed either by sonication in isotonic buffer or by hypotonic Dounce homogenization or treatment with nonionic detergents such as Triton X-100 or Nonidet P-40. These methods yield near 50% soluble recombinant polymerase α protein at 48 hours post-infection. To minimize proteolytic degradation and time of manipulation, sonication has been used in most of the experiments described here. About 50% of the expressed polymerase α protein can be isolated in soluble enzymatically active form by sonication of insect cells at 48 hours post-infection in isotonic buffer (FIG. 5C). An additional 15–20% of the polymerase α activity could be resolubilized from the insoluble pellet by a high salt extraction (FIG. 5D). After high salt extraction, the most abundant protein remaining in the insoluble pellet was the recombinant human polymerase α protein which comprised approximately 30–35% of the total expressed recombinant polymerase α protein. After 48 hours of infection, the solubility of the produced recombinant polymerase α protein decreased as post-infection time progressed. At later time points such as 72 and 84 hours post-infection, a much lower amount of undegraded recombinant p180 polymerase α protein is detected in soluble cellular lysates by Coomassie staining (FIG. 5C).

Using previously produced polyclonal antisera directed against 20 amino acid residues at the N- and C-termini of human polymerase α catalytic polypeptide (SEQ ID NO:31) which are designated DPN and DPC, respectively, a specific labile site was defined near the N-terminus of the catalytic polypeptide. See K. Hsi et al., Nucleic Acids Res. 18:6231 (1990). To analyze the proteolytic susceptibility of the over-produced recombinant polymerase α, whole cell lysates were transferred to membrane and immunoblotted with antisera, DPN and DPC. Immunoblot analysis indicates substantial degradation of the expressed polymerase α protein from both the N- and C-termini even at 36 hours post-infection (FIG. 5B). The predominant protein detected by the antisera was 180 kDa and the most abundant proteolytic product is the p140 detected only by the DPC antibody. The degradations of recombinant protein detected by the DPN antisera have not been observed in polymerase α protein purified from cultured human cells. The degraded polymerase protein may not be detectable in preparations from cultured human cell due to the low quantity of polymerase.

FIG. 5F illustrates the total enzymatic activity of the soluble recombinant polymerase α in the cell lysates and the activity resolubilized by high salt extraction of the cell pellet. The amount of soluble and assayable recombinant human polymerase a activity reaches a maximal level after 48 hours post-infection. After 48 hours, the soluble activity slightly decreases in the later post-infection harvested cells. As shown in the profile (FIG. 5C and 5F), the degraded p180 protein retains nearly full activity. This is in agreement with several previous reports in which demonstrate that degraded forms of the polymerase α protein retain full enzymatic activity. The assayable recombinant DNA polymerase α activity at 48 hours post-infection is approximately 1000 fold over that in uninfected Sf9 cells. This over-production can be improved by infection of Sf21 cells in serum free media. When human polymerase α molecule is quantitated on a per cell basis, the Sf9 cells grown in TNM-FH media produce about $6 \times 10^6$ molecules of soluble and catalytically active recombinant enzyme per cell. Sf21 cells produce approximately twice this much recombinant polymerase α per cell. Furthermore, when Sf21 cells are grown in EX-CELL 401 media, they produce four times the amount of recombinant human polymerase α in approximately $2.4 \times 10^7$ molecules per cell as compared to Sf9 cells grown in TNH-FH media (data not shown). Comparing the expression of the recombinant human polymerase α in insect cells to those described in transformed or normal cultured human cells, the recombinant human polymerase α is overproduced greater than 1,000-fold. Moreover, AcHDPα infected insect cells grown in suspension culture produce comparable levels of recombinant polymerase activity. The assayable polymerase activity solely represents the recombinant human DNA polymerase activity and not the endogenous baculovirus DNA polymerase activity, since the baculovirus polymerase gene is transcribed as early as 2 hours post-infection, reaches a maximum level at 6 hours and declines to negligible level by 12 hours post-infection.

III. PROTEIN PURIFICATION AND CHARACTERIZATION

For protein purification, Sf9 cells infected at a multiplicity of infection (M.O.I) of 10 were harvested as early as 36 hours to 55 hours post-infection. Briefly, cells were removed from T150 flasks by shaking and harvested by centrifugation at <200×g. The cells were washed in serum free Grace media and sonicated for 10 seconds in 20% ethylene glycol, 100 mM Tris HCl, pH7.5, 100 mM NaCl, 1 mM EDTA, 1 mM β-mercaptoethanol, 1 mM phenylmethanesulfonyl fluoride and 1 mM Sodium bisulfite. This extract was centrifuged for 10 minutes at 12,000×g. The supernatant was removed and saved as the soluble extract while the insoluble pellet was extracted with 600 mM NaCl, 50 mM potassium phosphate, pH 7.5, 20% ethylene glycol, 1 mM EDTA, 1 mM β-mercaptoethanol, 1 mM phenylmethane-sulfonyl fluoride and 1 mM Sodium bisulfite. This extraction was again centrifuged at 12,000×g for 10 minutes and the supernatant designated as the high salt solubilized fraction. The soluble and high salt solubilized fractions were then combined and adjusted to 100 mM ionic strength with 20% ethylene glycol, 1 mM EDTA and 1 mM β-mercaptoethanol, and batch adsorbed onto phospho-cellulose equilibrated in 20% ethylene glycol, 100 mM potassium phosphate, pH 7.5, 1 mM EDTA and 1 mM β-mercaptoethanol. The resin was washed extensively with the equilibration buffer and the enzyme removed by step elution with 300 mM potassium phosphate as described by T. Wang et al., J. Biol. Chem. 259:1854 (1984).

Figure 6A:
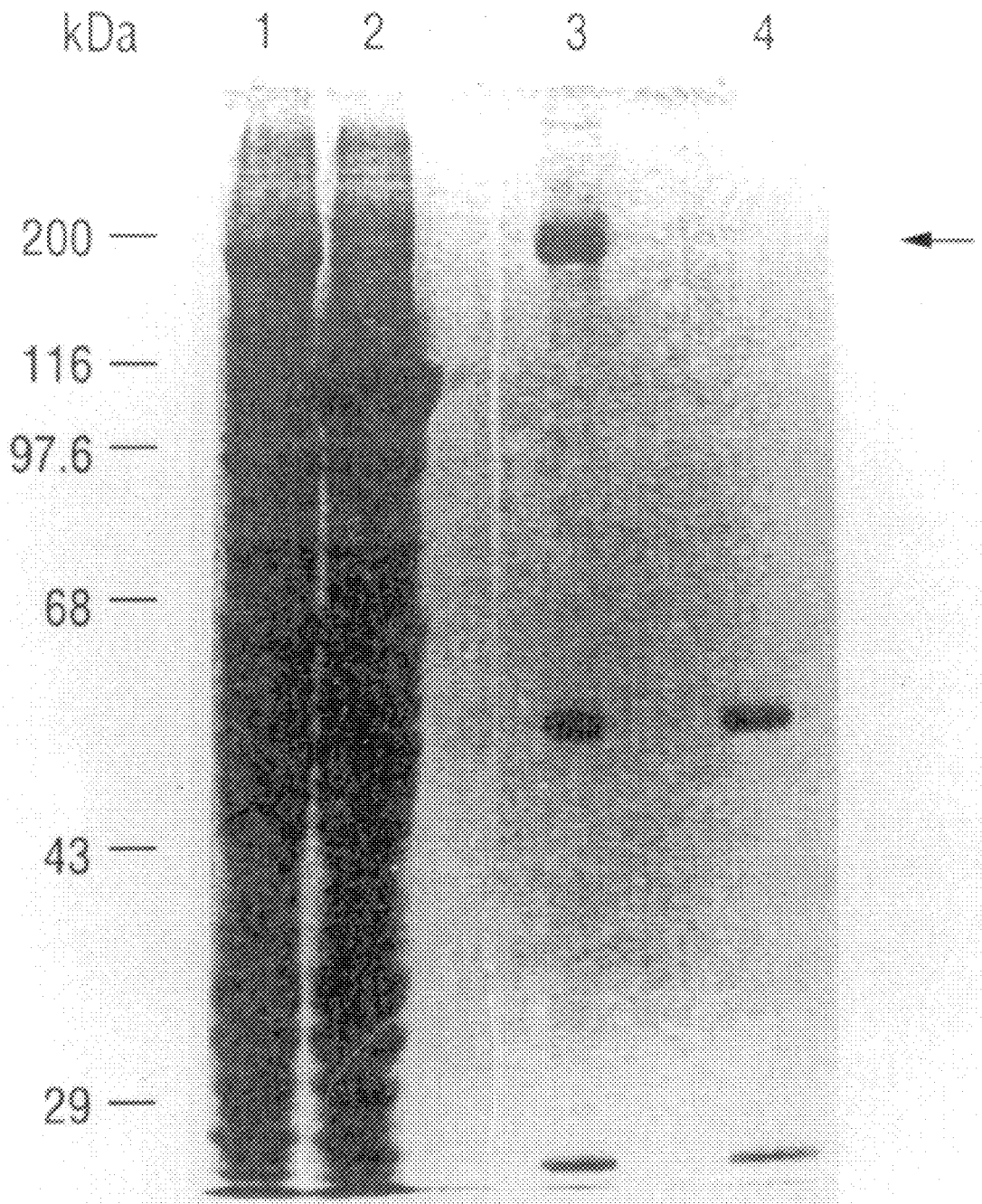
FIG. 6A is a photograph of an SDS-PAGE gel stained with Coomassie blue following electrophoresis.

Immunoprecipitation. Immunoprecipitation of the recombinant human DNA polymerase α polypeptide was performed generally as described by S. W. Wong et al., J. Biol. Chem. 261:7958 (1986) and P. A. Fisher and D. Korn, J. Biol. Chem 252:6528 (1977). Briefly, monoclonal SJK-237-71 (ATCC Catalogue # CRL 1645, 6th Ed. 1988), was used to immunoprecipitate antigen proteins from Sf9 cell lysates which were infected with either AcHDPα or with a control recombinant baculovirus, AcμGal. After separation on SDS-PAGE the gel was stained with Coomassie blue (FIG. 6A). Lanes 1 and 2, 100 μg of $^{32}PO_4$-labeled AcHDPα and AcβGal-infected cell soluble lysates, respectively. Lanes 3 and 4 are immunoprecipitations from the AcHDPα infected cell soluble lysate, and AcβGal-infected cell soluble lysate, respectively. The 55 and 25 kDa peptides in all the immunoprecipitations represent the heavy and light chains.

A densely staining polypeptide of 180 kDa is immunoprecipitated from Sf9 cells infected by AcHDPα, (FIG. 6A, lane 3), whereas no protein of this size range is immunoprecipitated from the mock infected cell lysates (FIG. 6A, lane 4). Because of the large excess of β-galactosidase present in the lysate from the AcβGal infected cells, a small amount of β-galactosidase was carried over in the immunoprecipitation. The two neutralizing monoclonal antibodies, SJK-132-20 and SJK-287-38 (ATTC Catalogue #CRL 1640 and 1644), are also able to immunoprecipitate the single subunit recombinant polymerase α (data not shown).

It has been reported that human polymerase α catalytic polypeptide (p180) and the p70 subunit are phosphoproteins and the phosphoamino acids are phosphoserine and phosphothreonine. Furthermore, it was found that the catalytic subunit p180 is phosphorylated through the cell cycle but hyperphosphorylated during mitotic phase. The p70 subunit is only phosphorylated in mitotic cells. To test whether the single subunit recombinant human polymerase α is phosphorylated in AcHDPα infected insect cells, AcHDPα infected Sf9 cells were incubated with $^{32}$P-orthophosphate 24 hours post-infection in normal TNM-FH media which contains 1.0 g/liter of cold sodium phosphate.

Figure 6B:
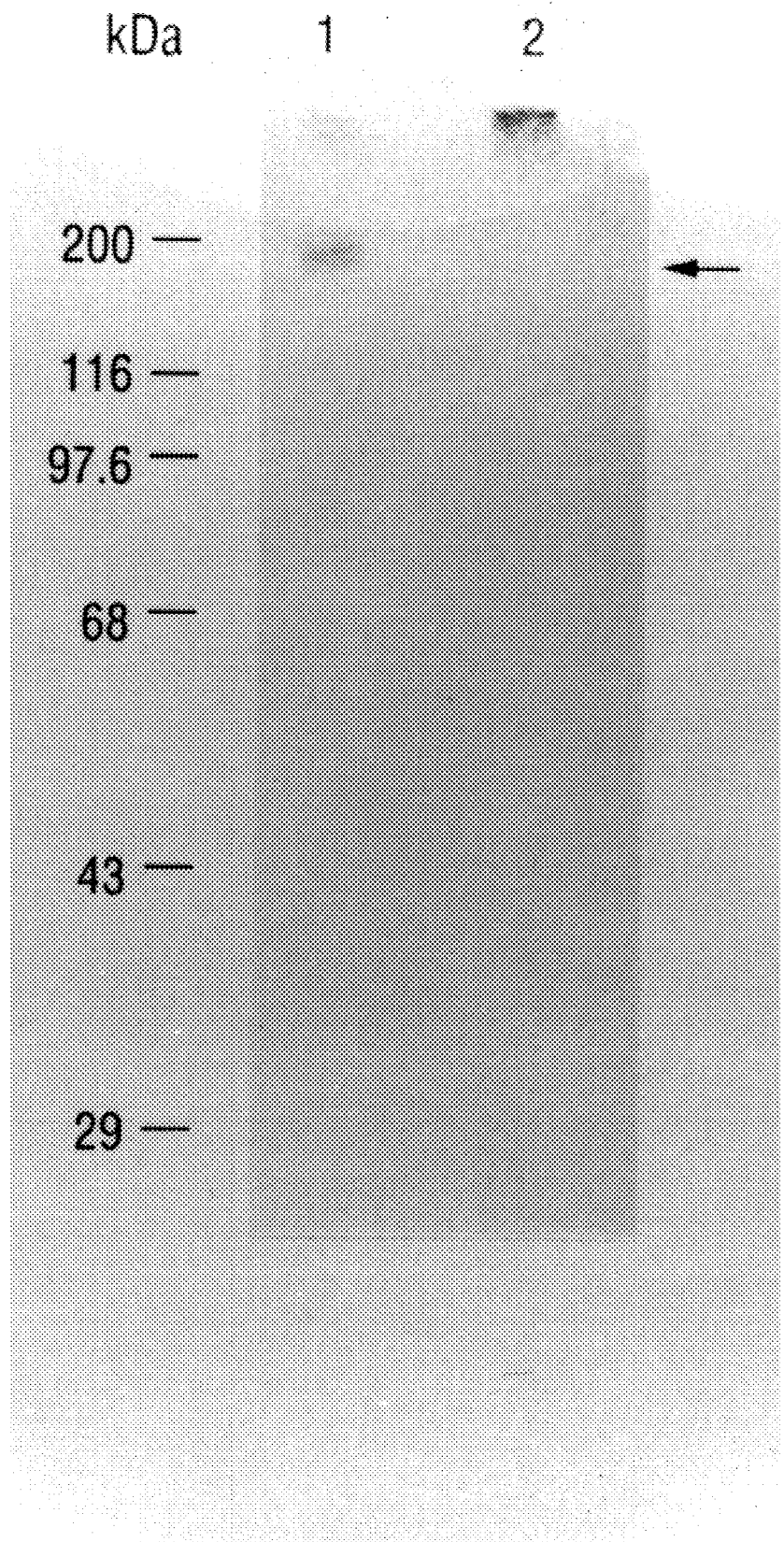
FIG. 6B is a photograph of an autoradiogram of lanes 3 and 4 of FIG. 6A.

Specifically, in vivo phospholabeling of polymerase α in Baculovirus infected cells was accomplished by adding (at 26 hours post-infection) 330 μCi of inorganic ortho-$^{32}$PO$_4$ to 1.5×10$^7$ Sf9 cells in a T150 flask in normal TNM-FH media (1.8 mCi/mmol). Sf9 cells were harvested at 38 hours post-infection, lysed by sonication and immunoprecipitated with SJK237-71 monoclonal antibody covalently linked to Sepharose 4B by mixing the lysate end over end with the Sepharose beads at 4° C. for 1 hour. Beads were then washed 10 times with radioimmune precipitation buffer followed by boiling in SDS gel loading dye and loaded directly onto an 8% SDS polyacrylamide gel. After electrophoresis (SDS-PAGE) the gel was then stained with Coomassie brilliant blue, destained, dried and subjected to autoradiography. FIG. 6B is the autoradiogram of immunoprecipitation of lanes 3 and 4 of FIG. 6A (24 hour exposure).

Immunoprecipitation of labeled cell lysates with SJK237-71 demonstrates a readily detectable phosphoprotein of 180 kDa from lysates of AcHDPα infected Sf9 cells labeled in the high phosphate medium (FIG. 6B, lane 1).

Immunoaffinity Purification. Immunoaffinity purification of the recombinant human DNA polymerase α polypeptide was performed generally as described by T. Wang et al., J. Biol. Chem. 259:1854 (1984). Fifteen-T150 flasks each containing 1.5×10$^7$ Sf9 cells infected with AcHDPα at multiplicity of 10 were harvested at 40 hours post-infection as described above and a crude cytoplasmic extract was prepared. The crude lysate containing the recombinant polymerase α was batch absorbed on phosphocellulose in buffer (1 mM mercaptoethanol, 1 mM EDTA and 20% ethylene glycol). After extensive washing, the enzyme was removed by step elution in 0.3 M KPO$_4$ (pH 7.5). Monoclonal antibody SJK237-71 was preadsorbed on a Protein A-sepharose CL-4B column (Sigma Chemical Co.) to make an IgG-Protein A matrix. The phosphocellulose eluate was adjusted to pH 8.2 and added to the matrix. After washing the column with buffer, the retained polymerase activity was eluted with 50 mM Na acetate (pH 5.5) containing 1 M KCL. After dialysis, the enzyme was further purified on a denatured calf thymus DNA-cellulose column.

Figure 7A:
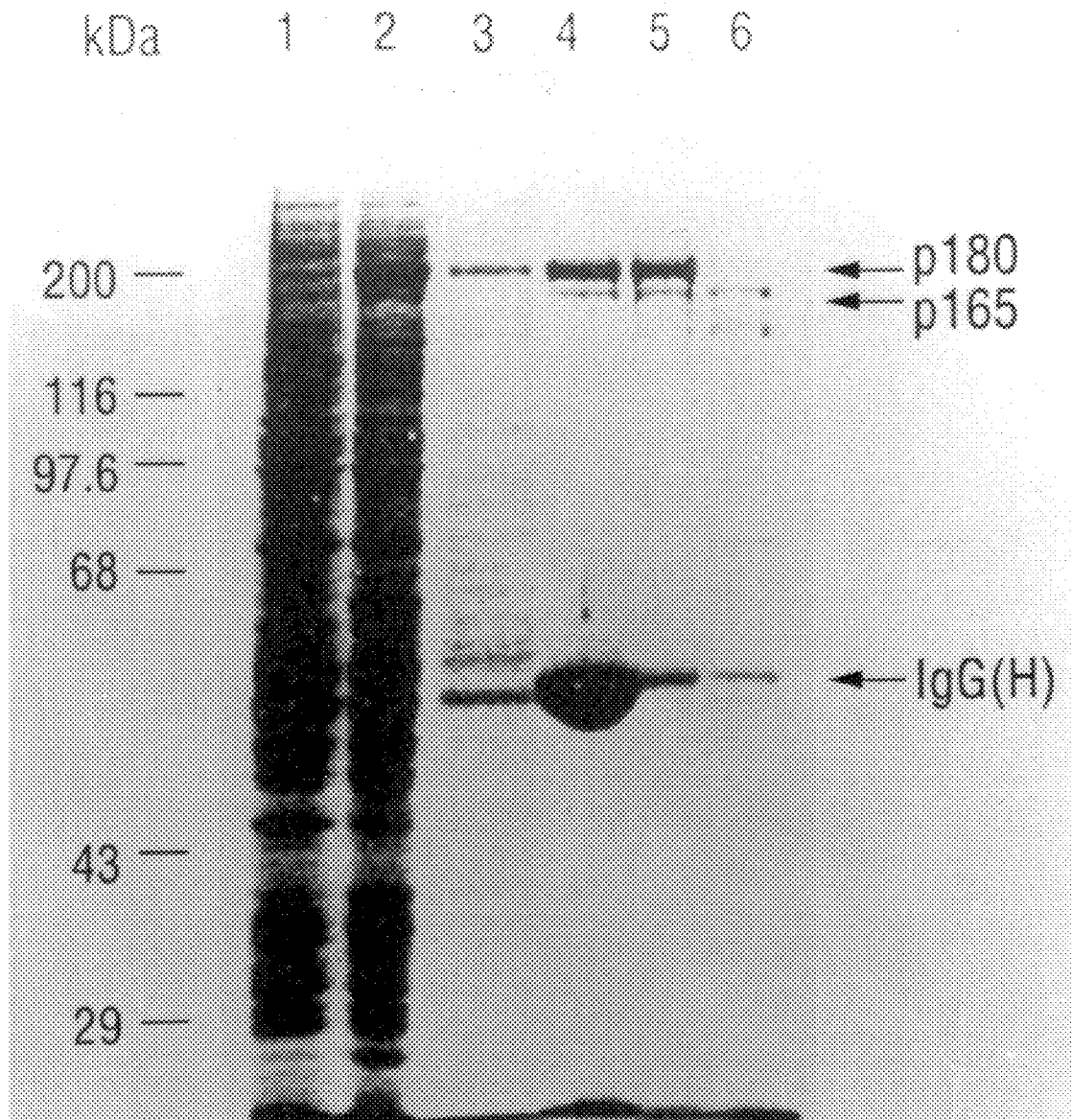
FIG. 7A is a photograph of a Coomassie stained gel following electrophoresis.

The results of the immunopurification protocol are presented in Table I and the recombinant polymerase α protein profiles for each step of the purification are shown in FIG. 7. FIG. 7A is a Coomassie stained gel of active polymerase α fractions throughout the purification. Lane 1, 120 μg of soluble crude cell lysate from uninfected Sf9 cells. Lane 2, 120 μg of soluble crude cell lysate from AcHDPα infected Sf9 cells. Lane 3, 20 μg of the phosphocellulose peak fraction. Lane 4, 50 units of polymerase α activity from the pooled SJK-237-IgG Protein A column eluate. Lane 5, 50 units of polymerase α activity from the pooled DNA-cellulose fractions. Lane 6, 40 units of active four subunit-DNA polymerase α/primase complex from cultured KB cells used as a standard for comparison. Less amount of proteins appears to be loaded in lane 6 than in lane 5 as indicated by the tightly associated monoclonal antibody heavy chain in 1:1 ratio in lane 5 and 6. In lane 6, the catalytic polypeptide of KB polymerase α contains not only the intact 180 kDa species but also the proteolytically degraded forms ranged from 160 to 120 kDa. Comparable specific activity of the recombinant single subunit polymerase α and the four subunit polymerase is estimated according to the combined amount of catalytic polymerase α protein of the KB cells.

Figure 7B:
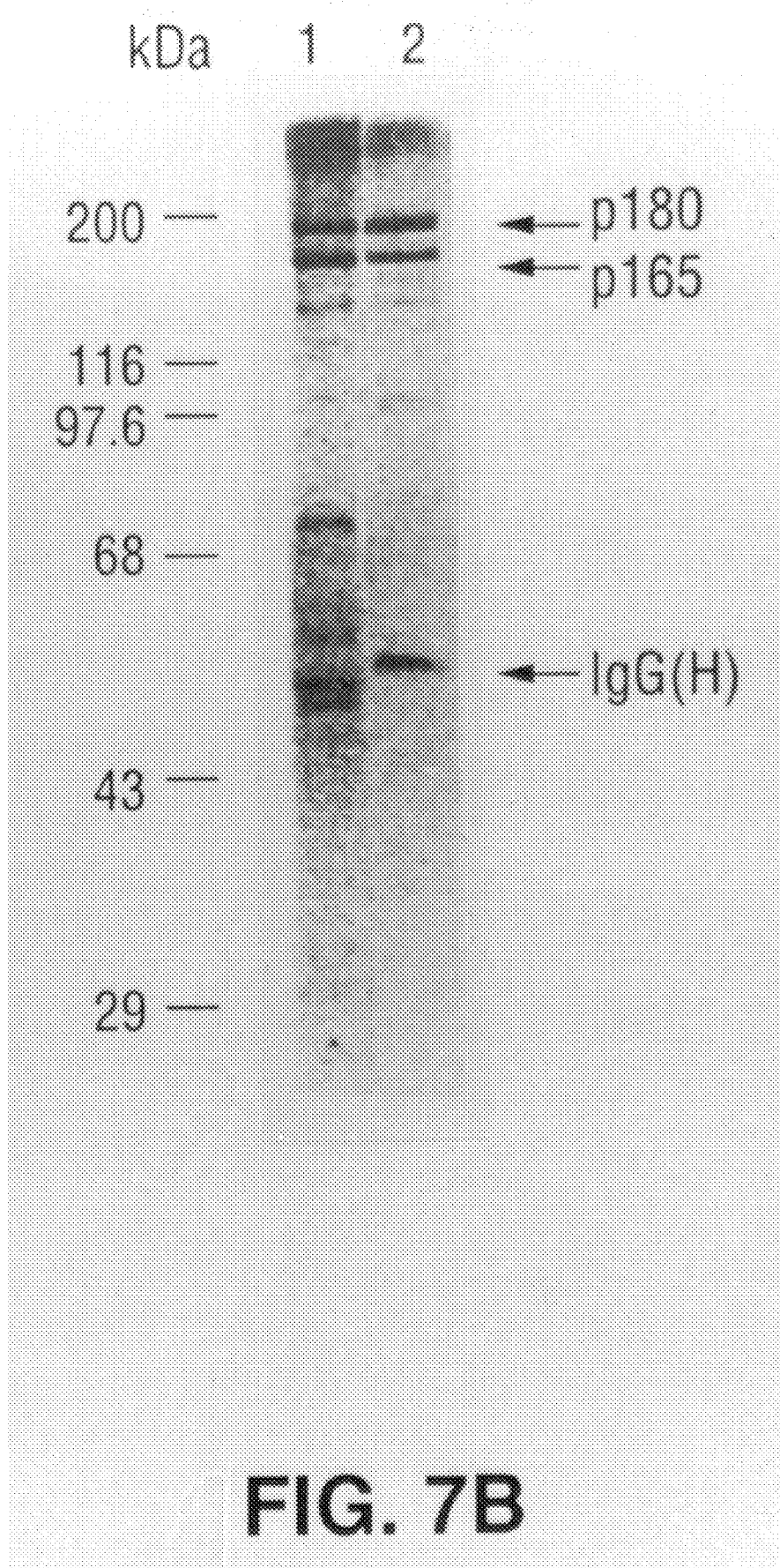
FIG. 7B is a photograph of a silver stained gel following electrophoresis.

FIG. 7B is a silver stained gel of immunopurified polymerase α. Lane 1, 5 units of 4 subunit-DNA polymerase α/primase from KB cells from an antigen preparation using covalently linked SJK237-Sepharose 4B. Lane 2, 5 units of active single subunit recombinant polymerase α immunopurified from AcHDPα infected Sf9 cells by SJK237-Protein A Sepharose 4B, a similar immunopurified preparation to that shown in lane 5 of FIG. 7A. Arrows designate the p180 and p165 polypeptides of the polymerase as well as the heavy chain from the hybridoma SJK237-IgG.

TABLE 1

Immunopurification of the recombinant human DNA polymerase α from insect Sf9 cells

| Active Fraction | Total Protein[a] | Total Units[b] | Sp. Activity[c] | % Yield |
|---|---|---|---|---|
| Crude cell lysate | 98.4 mg | 38,400 | 390 | 100 |
| Phosphocellulose | 18.7 mg | 35,710 | 1910 | 93 |
| IgG-Protein A | 0.18 mg | 13,050 | 70,000[d] | 34 |
| DNA Cellulose | 38 μg | 7,680 | 200,000[d] | 20 |

[a]Protein concentrations of crude cell lysates and phosphocellulose fractions were determined by Bradford analysis using BSA as the standard. IgG-protein A and DNA cellulose protein fractions were determined by densitometric analysis of Coomassie blue stained gels containing known amounts of BSA standard.
[b]One unit of DNA polymerase is defined as the amount of protein to incorporate one nmole of labeled dNMP per hour.
[c]Specific Activity is defined as units DNA polymerase per total mg of protein.
[d]Specific activity of non-IgG protein. Specific activity with IgG is 9700 and 57,000 units/mg for IgG-protein A and DNA cellulose fractions, respectively.

From the data, it is apparent that, in the soluble crude cell lysate, the specific activity of the polymerase activity is at least 100-fold higher than that obtained by a traditional crude human KB cell extract (compare, for example, with the data in Table I of T. Wang et al., J. Biol. Chem. 259:1854 on page 1856). Subsequent purification increases this specific activity. In particular, immunoaffinity chromatography separates the polymerase from other cellular protein and renders it substantially purified.

Importantly, no protein species of a size corresponding to the baculovirus polymerase (114 kDa) was detected by electrophoresis following the last two purification steps, i.e., the SJK237-71-Protein A fraction and DNA cellulose fraction, (FIG. 7A, lanes 4 and 5). This further confirms the species specificity of monoclonal antibody SJK237-71, eliminating the possible cross-reactivity of Sf9 insect cell polymerase in the immunoaffinity purified enzyme fractions. (This species specificity was also demonstrated above in FIG. 6A, lane 4 with the immunoprecipitation of mock-infected Sf9 cell control.)

Characterization of Affinity. The four subunit-DNA polymerase α/primase complex was purified from human KB cells as described T. Wang et al., J. Biol. Chem. 259:1854 (1984) and used for comparison to the single polypeptide recombinant polymerase α for their respective affinities for dNTP, primer-terminus, and gapped DNA. Prior to the comparison, both the immunopurified recombinant single subunit-polymerase α and the four subunit-polymerase α/primase complex were stored in buffer containing 30% sucrose, 20% ethylene glycol, 50 mM Tris HCL, pH 8.6, 1 mM βME, 1 mM EDTA at −80° C. or stored on packed ice at 4° C.

The standard assay for DNA polymerase α with gapped DNA was performed according to P. A. Fisher and D. Korn, J. Biol. Chem 252:6528 1977). Reactions were performed using optimally gapped salmon sperm DNA in 20 mM Tris-HCl, pH 8.0, 2 mM β-mercaptoethanol ("βME"), 200 μg/ml BSA, 10 mM $MgCl_2$, 50 μM dNTP's with [α-$^{32}$P] dATP as the label. One unit of DNA polymerase is defined as the amount of polymerase that incorporates 1 nmole of labeled dNTP into acid-insoluble DNA at 37° C. in 60 min. $K_m$ values for primer terminus were performed on oligo(dT)$_{12}$: poly(dA)$_{290}$, where an average of five oligodT molecules were annealed per polydA molecule and reaction was performed in 20 mM Tris.HCl, pH 8.0, 2 mM βME, 200 μg/ml BSA, 2 mM $MgCl_2$ and 50 μM [α-$^{32}$P]dTTP. All Kinetic parameters were calculated from Lineweaver-Burk plots by the method of least squares. Km was calculated of the basis of 3'-OH primer termini.

The kinetic parameters determined for dNTPs, primer-terminus and gapped DNA are summarized in Table II and demonstrate no apparent differences between the two forms of DNA polymerase α. The rate of catalysis of these two forms was also measured. The Kcat values determined for the two forms of polymerase α are of a similar order of magnitude.

Reactivity to Aphidicolin and $N^2$-(p-n-butylphenyl)-dGTP. DNA polymerase α is distinct from DNA polymerases δ or ε for its sensitivity to the dNTP analog, $N^2$-(p-n-butylphenyl)-dGTP. This compound is a potent inhibitor of the DNA synthetic capacity of DNA polymerase α, but not of DNA polymerases δ or ε. Another compound, aphidicolin, a potent DNA synthesis inhibitor in vivo, inhibits all three DNA polymerases in vitro. The recombinant single subunit-polymerase α and the four subunit-polymerase α/primase complex from cultured human KB cells were comparatively assayed in the presence of increasing concentrations of $N^2$-(p-n-butylphenyl)-dGTP or aphidicolin. These inhibitor studies were performed as standard DNA polymerase assays with the amount of added inhibitors as following: $N^2$-(p-n-butylphenyl)-dGTP inhibition reactions were performed in the concentration range of 0.1 to 50 μM, while the aphidicolin inhibition reactions were performed in the concentration range of 1 to 1000 μM. Inhibition curves were plotted and data presented as concentration of each inhibitor which causes 50% inhibition. Both forms of polymerase α were extremely sensitive to these compounds and their levels of sensitivity were identical, Table II.

Thermosensitivity. The thermostability of the two forms of polymerase α was also compared; this was done by preincubation at 37° C. for various times before assaying polymerase activity. Both forms of polymerase α activity were found to decay at a nearly identical rate to ~67% of the original activity after 30 minutes at 37° C., Table II. Moreover, activities of both forms of the polymerase α also were found to decrease at approximately the same rate when stored at 4° C. (data not shown). These decreases in polymerase activity was not due to proteolysis of the polymerase protein. Gel analysis of the two forms of enzyme after prolonged storage at 4° C. or after incubation at 37° C. demonstrates only nominal degradation of the 180 kDa catalytic polypeptide (data not shown).

TABLE II

Properties of the four subunit and single subunit recombinant DNA Polymerase α

| Property* | Enzyme | |
|---|---|---|
| | 4 subunit Pol α | Single subunit recombinant Pol α |
| $K_m$ (dNTP), μM | 1.55 | 1.20 |
| $K_m$ (primer terminus), μM | 0.3 | 0.4 |
| $K_m$ (DNA in nucleotide), mM | 0.22 | 0.19 |
| $K_{cat}$ sec$^{-1}$ | 1.3 | 1.6 |
| 50% BuPdGTP inhibition, μM | 0.22 | 0.22 |
| 50% Aphidicolin inhibition, μM | 13 | 20 |
| Thermostability, % activity after 30 min at 37° C. | 66 | 68 |

*Reactions were performed using optimally gapped salmon sperm DNA in 20 mM Tris HCl, pH 8.0, 2 mM βME, 200 μg/ml BSA, 10 mM $MgCl_2$, 50 μM dNTP's with [α − $^{32}$P] dATP as the label. $K_m$ values for primer terminus were performed on oligo (dT)$_{12}$: poly (dA)$_{290}$ in 20 mM Tris HCl, pH 8.0, 2 mM βME, 200 μg/ml BSA, 2 mM $MgCl_2$ and 50 μM [α − $^{32}$P] dTTP. All Kinetic parameters were calculated fromLineweaver-Burk plots by the method of least squares.

Absence of Associated Exonuclease Activity. Purified four subunit-DNA polymerase α/primase complex from a variety of species does not contain detectable 3'-5' exonuclease proofreading activity. It has been reported that a cryptic proofreading 3'-5' exonuclease is present in the Drosophila DNA polymerase α catalytic subunit when separated from the other associated subunits. The over-produced single subunit recombinant human polymerase α from AcHDPα infected Sf9 cells provides an ideal enzyme to investigate the presence of a cryptic exonuclease in the polymerase α from somatic human cells.

Proofreading exonuclease activity of the recombinant single subunit polymerase α was assayed with a singly primed M13mp18 template (SEQ ID NO:5), primed either with a matched 24mer (SEQ ID NO:4) (FIG. 8B) or a mismatched 29mer (SEQ ID NO:2) (FIG. 8A), each $^{32}$P-labeled at the 5' end by T4 polynucleotide kinase. The mismatched 29mer (SEQ ID NO:2) contains 9 mismatched T's on the 3' terminus. Correct proofreading of this 29mer (SEQ ID NO:2) annealed to M13mp18 (SEQ ID NO:3) would produce a 20mer in the absence of deoxynucleotide triphosphates (dNTPs).

To perform the assay, two oligonucleotides, the universal primer, a 24mer (matched primer) and RD29mer (mismatched primer), were 5'-end labeled with $^{32}$P-ATP and annealed to M13mp18 single stranded template. 0.1 pmole of this primed M13 was incubated in 20 mM Tris.HCl, pH 7.5, 10 mM $MgCl_2$, 20 mM KCl and 2 mM dithiothreitol at 37° C. in the presence of polymerase in a final volume of 12 μl. Aliquots of 3 μl each were removed at 0, 2.5, 10 and 30 minutes into an equal volume of deionized formamide containing 1 mM EDTA, 0.1% xylene cyanol and 0.1% bromophenol blue and placed on ice. After heating at 95° C. for 5 minutes, one-half of the sample was loaded onto an 18% polyacrylamide, 7 M urea, Tris-borate-EDTA gel.

The recombinant single subunit polymerase α of the present invention was assayed and compared to the four subunit-polymerase α/primase complex, human DNA polymerase ε, and T4 DNA polymerase, FIG. 8. In both Figures (A) and (B) lanes 1 represents the incubation of the primed M13 with no enzyme for 2.5 minutes; lanes 2, 3, and 4 are the incubations with the primed M13 substrate for 2.5, 10, and 30 minutes at 37° C. in the presence of 1.0 units of the four subunit-polymerase α/primase complex from KB cells, respectively; lanes 5, 6, and 7, are incubations with 1.0 units of the single subunit recombinant polymerase α immunopurified from AcHDPα infected Sf9 cells for 2.5, 10, and 30 minutes, respectively; lanes 8, 9, and 10, are incubations in the presence of 0.4 units of purified HeLa cell DNA polymerase ε for 2.5, 10, and 30 minutes, respectively; and lanes 11, 12, and 13 are incubations in the presence of 0.02 units of phage T4 DNA polymerase for 2.5, 10, and 30 minutes, respectively.

Figure 8A:
FIG. 8A is an autoradiogram of the exonuclease assay using 0.1 pmole of the $^{32}$P-5'-labeled mismatched 29mer SEQ ID NO:2 annealed to M13 mp18 single stranded DNA SEQ ID NO:3 as substrate.
Figure 8B:
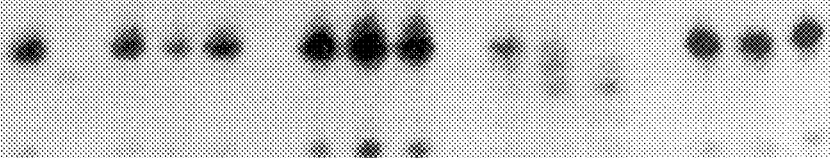
FIG. 8B is an autoradiogram of the exonuclease assay using 0.1 pmole of the $^{32}$P-5'-labeled matched 24mer SEQ ID NO:4 annealed to M13 mp18 single stranded DNA SEQ ID NO:5 as substrate.

It is clear that after 30 minutes of incubation, no apparent 3'-5 exonuclease was detected in either the recombinant single subunit-polymerase α or the four subunit-polymerase α/primase complex assayed with either the mismatched primer-template (the 29mer (SEQ ID NOS:2,3); FIG. 8A) or the matched primer-template (the 24mer (SEQ ID NOS:4,5); FIG. 8B). (The matched primer (SEQ ID NO:4) contains a small amount of contaminating primer of 19 bases in length and is not the result of exonuclease activity as seen in the control in lane 1.) In contrast, both the polymerase ε from HeLa cells and T4 DNA polymerase digested both the mismatched (SEQ ID NOS:2,3) and the matched primer-templates (SEQ ID NOS:4,5) but with a specificity for the mispaired primer. These results demonstrate that, unlike the finding of a cryptic exonuclease in Drosophila embryo polymerase α, the catalytic polypeptide of human DNA polymerase α either in the four-subunit complex form or as a single-subunit lacks detectable proofreading exonuclease.

A recent report describes the purification and reconstitution of the yeast polymerase α catalytic subunit with the p86 subunit. The exonuclease activity of the four subunit yeast polymerase α/primase complex versus the single catalytic subunit yeast polymerase α and the reconstituted p180-p86 complex were investigated. See R. G. Brooke et al. J. Biol. Chem 266:3005 (1991). No proofreading activity was detected in any of the yeast polymerase forms, but a 3'-5' exonuclease activity was detected using substrates such as poly(T)$_{600}$·[$^{32}$P]dCMP$_{0.4}$ and on longer polynucleotides but not with short polynucleotides such as poly(dT)$_{25}$ or poly (dT)$_{50}$ as substrate.

Figure 9:
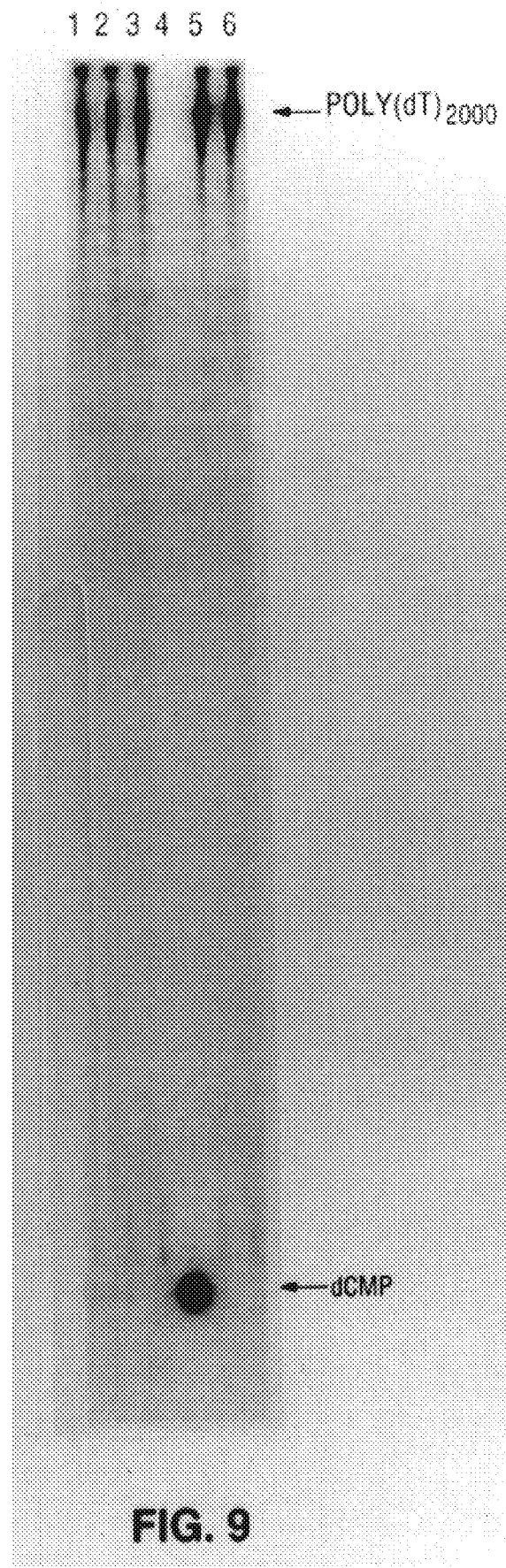
FIG. 9 is an autoradiogram following electrophoresis showing the lack of exonuclease activity of the polymerase of the present invention on a polynucleotide template.

To test whether the recombinant human single subunit of the present invention could release label from this kind of nonphysiological synthetic substrate, poly(dT)$_{2000}$ was end-labeled with [α-$^{32}$P]dCTP by calf thymus terminal deoxynucleotide transferase. Possible 3'-5' exonuclease activity was tested using the poly(dT)$_{2000}$[$^{32}$P]dCMP$_{0.5}$ as substrate in the nucleotide release assay described by Brooke et al. After 30 minutes at 30° C. 35 μl of the 40 μl reaction was removed and acid precipitated with carrier DNA as performed in the standard DNA polymerase assay. The remaining 5 μl of reaction was mixed with an equal volume of 95% formamide sequencing loading dye of which 2 μl was loaded onto a 7 M urea, 8% polyacrylamide sequencing gel followed by electrophoresis and autoradiography. FIG. 9 shows the results from this assay. Incubation of substrate with 4 subunit-polymerase α/primase complex, (lane 1); recombinant single subunit-polymerase α, (lane 2); recombinant human polymerase β, (lane 3); T4 DNA polymerase, (lane 4); and buffer only controls, (lanes 5 and 6). The released dCMP label is designated by the lower arrow and the poly(dT)$_{2000}$·[$^{32}$P]dCMP$_{0.5}$ substrate is designated by the upper arrow.

The results of FIG. 9 indicate that both the four subunit and single subunit recombinant polymerase α do not contain any detectable exonuclease activity on this nonphysiological synthetic substrate. As control for the assay, the recombinant human polymerase β and T4 DNA polymerase were used as negative and positive controls, respectively. As with the native human polymerase β, no detectable exonuclease activity was found with the recombinant human polymerase α of the present invention, while the T4 DNA polymerase released all of the dCMP label.

Aliquots of the reaction were also quantitated by acid precipitation and counted. The exclusion of exonuclease activity from polymerase activity in recombinant human single subunit and four subunit polymerase α/primase complex as well as the recombinant human DNA polymerase β demonstrate <3×10$^{-6}$ nuclease/polymerase activity. In contrast, the T4 DNA polymerase released >99% of the label. This quantitative analysis makes it clear that the human recombinant single subunit polymerase α is devoid of any detectable 3'-5' exonuclease activity.

IV. TEMPLATE-DEPENDENT ENZYMATIC SYNTHESIS

Enzymatic synthesis that involves nucleic acid, either solely as a template (e.g., translation involves the use of nucleic acid as a template to make polypeptides) or as both a template and a product (replication and transcription use nucleic acid as a template to produce nucleic acid) is hereinafter referred to as "template-dependent enzymatic synthesis."

In the case of replication, nucleic acid polymerases replicate a nucleic acid molecule ("template") to yield a complementary ("daughter") nucleic acid molecule. For example, DNA polymerase I, isolated from E. Coli, catalyzes the addition of deoxyribonucleoside triphosphates to the 3' end of a short segment of DNA ("primer") hybridized to a template strand to yield a daughter of the template, starting from a mixture of precursor nucleotides (dATP, dGTP, dCTP, and dTTP).

This 5' to 3' template-dependent enzymatic synthesis is also called "primer extension." Importantly, the reaction will not take place in the absence of template and primer.

While all DNA polymerases require a 3'-hydroxyl terminus of a preexisting primer for reaction, DNA polymerase α (in its native form) is the only eukaryotic polymerase with a tightly associated primase. See T. Wang, Ann. Rev. Biochem 60:5413 (1991). A "primase" is a class of enzymes capable of accomplishing physiologically significant de novo primer synthesis. T. Wang et al., J. Biol. Chem. 259:1854 (1984).

When the single subunit recombinant human polymerase α of the present invention was compared with the four subunit DNA polymerase α/primase complex obtained by traditional methods (see Table II above), the kinetic parameters of the two forms of the polymerase appeared indistinguishable, suggesting that the absence of the other subunits was not critical to these functions.

The issue of the absence of the other subunits has been further examined. The single subunit recombinant polymerase α of the present invention was tested for its processivity and DNA synthetic fidelity.

DNA Synthetic Processivity. Enzymes that synthesize polymers may dissociate after each catalytic event, i.e., they may be "nonprocessive." On the other hand, they may remain bound to the polymer until many cycles of reaction are completed, i.e., they may be "processive." See A. Kornberg, DNA Replication (Freeman and Co. 1980). It is known that the four subunit DNA polymerase α/primase complex is moderately processive, polymerizing 10–20 bases per binding event. See T. Wang, Ann Rev. Biochem. 60:513 (1991).

The processivity of the polymerase subunit of the present invention was determined on singly primed M13mp18 ssDNA in the absence or presence of E. coli single stranded DNA binding protein (SSB) or on oligo(dT) primed poly (dA). For each reaction, 0.6 pmole of [$^{32}$P]-5' end labeled singly primed M13mp18 DNA where only one primer molecule was annealed per M13 template molecule was incubated in 50 µl with 0.015 pmole of designated DNA polymerase in 20 mM Tris.HCl, pH 8.0, 1 mM dithiothreitol, 200 µg/ml BSA, 10 mM MgCl$_2$, 100 µM each of dGTP, dCTP, dATP, and dTTP, at 37° C. E. coli SSB was present at a ratio of 8:1 nucleotides:SSB monomer.

Processivity on Poly(dA) was performed according to J. Syvaoja and S. Linn J. Biol. Chem 264:2489 (1989). Forty six pmole (in molecules) of oligo(dT)$_{12}$:poly(dA)$_{290}$, where only one oligo(dT)$_{12}$ molecule was annealed on average per one poly(dA)$_{290}$ molecule, was incubated with 1.1 fmol of DNA polymerase in a 40 µgl volume with 50 µM [$^{32}$P]dTTP (40,000 cpm/pmol) in 2 mM MgCl$_2$, 20 mM Tris.HCl, pH 8.0, 200 µg/ml BSA and 1 mM dithiothreitol at 37° C. For both the M13 and poly(dA) processivity reactions aliquots were removed at the indicated times indicated in the figure legends, phenol:chloroform extracted and ethanol precipitated with 10 µg salmon sperm DNA as carrier. Reaction samples were resuspended in deionized formamide containing 1 mM EDTA, 0.1% xylene cyanole and 0.1% bromophenol blue, and one-half of the sample loaded onto a 8% polyacrylamide, 7 M urea, Tris-borate-EDTA gel.

Figure 10A:
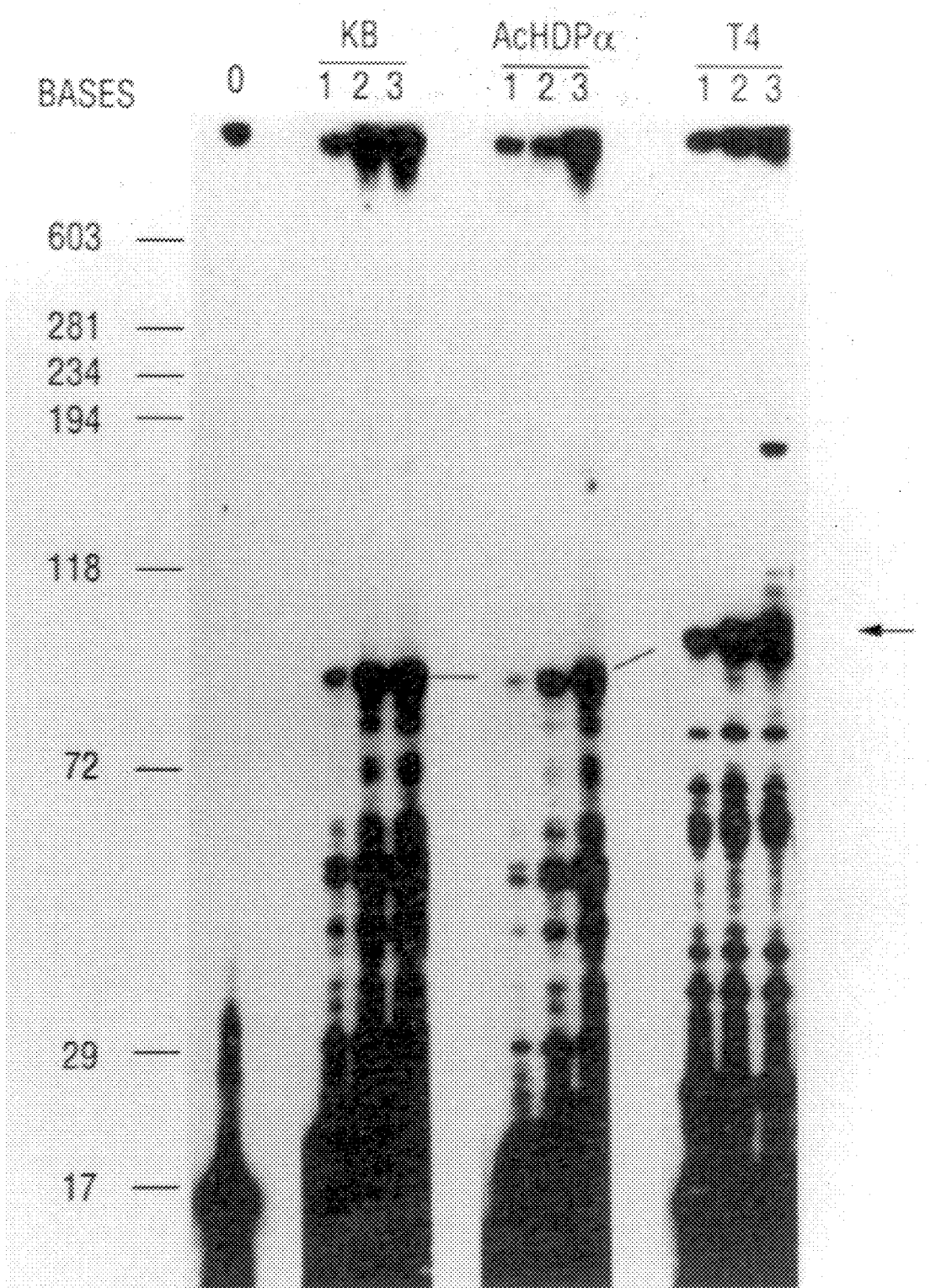
FIGS. 10A and 10B show a comparative analysis of DNA synthetic processivity on primed M13 single-stranded DNA and oligo(dT) primed poly(dA).

The DNA synthetic processivity of the single subunit recombinant human polymerase α of the present invention, using two kinds of primer-templates, is shown in FIG. 10. Processivity was measured by using singly primed M13 template in 40 to 1 excess molar ratio of primer-template to polymerase (FIG. 10A). $^{32}$P-5'-end labeled 17mer (0.6 pmole) annealed to 0.6 pmole M13mp18 single stranded DNA was extended by 0.015 pmole of polymerase for 2.5, 10, and 30 minutes. Samples were subjected to electrophoresis and autoradiography. Lane 0, incubation of the singly primed M13 in the absence of any added polymerase. Lanes 1, 2, and 3, represent incubation with the indicated polymerase for 2.5, 10 and 30 minutes, respectively. KB designates the four subunit human KB DNA polymerase α/primase complex, AcHDPα designates the single subunit recombinant polymerase α from AcHDPα infected Sf9 cells, and T4 designates the T4 DNA polymerase. Molecular weight markers are labeled HaeIII-digested φX174 DNA, 29mer and 17mer. The arrow indicates a pause site by the polymerases, corresponding to the lacZ operator sequence located 101 bases from the universal 17mer annealing site.

The single subunit recombinant polymerase α and the four subunit-polymerase α/primase complex exhibited similar DNA synthetic processivity on singly primed M13 (FIG. 10A). The presence of secondary structure in the M13 has reproducibly found to cause pausing for the polymerases. Synthesis by all the polymerases tested appeared to pause at the lacZ operator structure as indicated by the arrow in FIG. 10A. E. coli SSB could relieve this pause for the T4 DNA polymerase but had a slight inhibitory effect for the single and four subunit DNA polymerase a (data not shown).

Figure 10B:
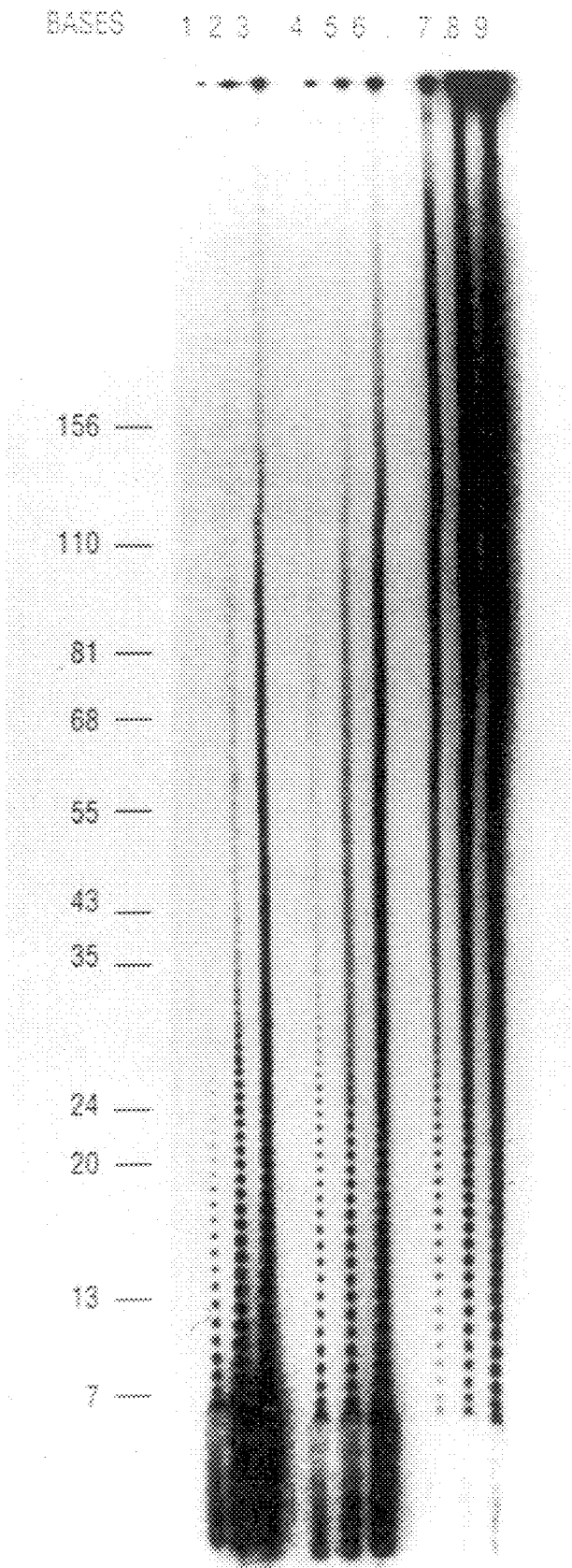

The singly primed M13 substrate, the bulk of which is single stranded DNA, has been documented to cause non-productive binding and inhibition to the polymerase α synthetic ability. Thus, DNA synthetic processivity of the two forms of DNA polymerase α were further evaluated on oligodT primed polydA as primer-template in >40,000 to 1 excess molar ratio of primer-template to polymerase (FIG. 10B). The recombinant single subunit polymerase and four subunit polymerase α/primase complex and T4 DNA polymerase, 1.1 fmol of each, were separately incubated with 46 pmol oligo(dT)$_{12}$·poly(dA)$_{290}$ at a primer-template ratio of 1:1, respectively, in 40 µl volume with 50 µM [$^{32}$P]-dTTP (40,000 cpm/pmol) in 2 mM MgCl$_2$ for 4, 12.5, and 30 minutes. Lanes 1, 2, and 3, incubations with KB four subunit polymerase α/primase complex, lanes 4, 5, and 6, incubations with the single recombinant polymerase α and lanes 7, 8, and 9, incubations with T4 DNA polymerase. The molecular weight marker is derived from a dideoxy sequencing reaction. The primer length of 12 has been subtracted from the molecular weight marker to reflect the nucleotides synthesized.

Like the results obtained when using singly primed M13 DNA, both forms of the DNA polymerase α exhibited near identical DNA synthetic processivity on this primer-template. Moreover, the products synthesized by the single subunit and four subunit polymerase α/primase complex on this primer-template demonstrate only an increase in net quantity of the same length with increasing incubation time which reflects a true measure of the processivity. The average length products synthesized by the single subunit and four subunit polymerase α were between 7 and 13 nucleotides which is in excellent agreement with the previous published data. These results demonstrate that both the single subunit-recombinant polymerase α and the four subunit polymerase α/primase complex synthesize DNA in a similarly moderate processivity.

DNA Synthetic Fidelity. The fidelity of the single catalytic subunit and the four subunit polymerase α/primase was measured and compared. Three methods were used to measure a single round of gap filling synthesis within the lacZ α-complementing gene in M13mp2 DNA. See T. A. Kunkel et al. Mol. Cell. Biol. 9:4447 (1989). In all three assays, a gapped, double-stranded M13mp2 DNA is constructed which contains a single-stranded gap as the mutation target. The three assays are: (A) forward mutation assay, (B) opal codon reversion assay, and (C) assay for −1 base frame-shift.

The DNA synthetic mutational frequency and the error rate of the two forms of DNA polymerase α measured by these three methods are summarized in Table III. The values for mutational frequency and error rate as measured by all three assays for the single subunit recombinant polymerase α and the four subunit polymerase α/primase complex are comparable if not identical. The DNA synthetic fidelity values obtained are also in agreement with the values previously determined for the four subunit polymerase α. These results further support the conclusion that proofreading 3'-5' exonuclease activity is absent in both the single subunit recombinant polymerase α and the four subunit polymerase α/primase complex (FIG. 8).

V. CHEMOTHERAPEUTIC SCREENING

The recombinant human polymerase α of the present invention is particularly useful for screening chemotherapeutics for potential mutagenicity and carcinogenicity. In one embodiment, recombinant human DNA polymerase α is employed to test for incorporation of analogs of the normal nucleotide bases during DNA replication.

One analog of a normal nucleotide base that has been of particular interest lately is 3'-azido-thymidine ("AZT"). AZT was prepared in 1978 by Prusoff and T. S. Lin at Yale University. It has been found active as an antiviral, exclusively against retroviruses. Samuel Broder and Robert C. Gallo of the National Cancer Institute and scientists from Wellcome Research have found that AZT blocks in vitro cytopathic effects of the AIDS virus; 3'-azido-thymidine

TABLE III

Fidelity of AcHDPα single catalytic polypeptide and KB 4 subunit polymerase α/primase

| DNA Polymerase | Plaques scored total | Plaques scored mutant | Mutant frequency | Error rate[1] |
|---|---|---|---|---|
| Forward mutation assay | (light blue and colorless) | | $(\times 10^{-4})$ | |
| Single catalytic polypeptide | 4,966 | 148 | 300 | |
| 4 subunit polymerase/primase | 5,119 | 145 | 280 | |
| Base-substitution reversion assay | | (blue) | $(\times 10^{-6})$ | |
| Single catalytic polypeptide | 420,000 | 154 | 370 | 1/4900 |
| 4 subunit polymerase/primase | 420,000 | 157 | 370 | 1/4900 |
| Minus-one frame-shift reversion assay[2] | | (blue) | $(\times 10^{-5})$ | |
| Single catalytic polypeptide | 750,000 | 1243 | 170 | 1/1800 |
| 4 subunit polymerase/pimase | 730,000 | 1122 | 150 | 1/2200 |

The background mutant frequency for uncopied DNA was $6.7 \times 10^{-4}$ for the forward mutation assay, $2 \times 10^{-6}$ for the base-substitution reversion assay and $1 \times 10^{-5}$ for the frame-shift reversion assay.
[1]Error rate is calculated as described in reference (25).
[2]The percentage of light blue of total blue plaques was 9%. The light blue plaques represent nonreiterated base frame-shifts and dark blue plaques represent -T errors in the TTTTT run.

5'-triphosphate apparently inhibits the viral reverse transcriptase, thereby inhibiting viral replication.

To test the usefulness of the recombinant human DNA polymerase α of the present invention as a reagent to screening analogs, the recombinant human DNA polymerase α enzyme was purified from Sf9 cells infected with the AcHDPα recombinant baculovirus and the purified polymerase α enzyme was used to test the incorporation of AZT into DNA. Briefly, a running start (SEQ ID NO:27) and standing start (SEQ ID NO:28) primer were separately 5' end labeled with [$^{32}$P] and annealed to their respective templates (SEQ ID NOS:29,30) as shown below:

Standing start primer-template pair:
    5'-$^{32}$P-TGA CCA TGT AAC AGA GAG-3"
       3'-ACT GGT ACA TTG TCT CTC ATT CTC TCT
          CTC TTC TCT-5'

Running start primer-template pair:
    5-32P-CGC CCA GCG GGC AGA G-3'
       3'-GCG GGT CGC CCG TCT CTT ACC TCT TCT
          CTC CTC TTC TCT-5'

Figure 11A:
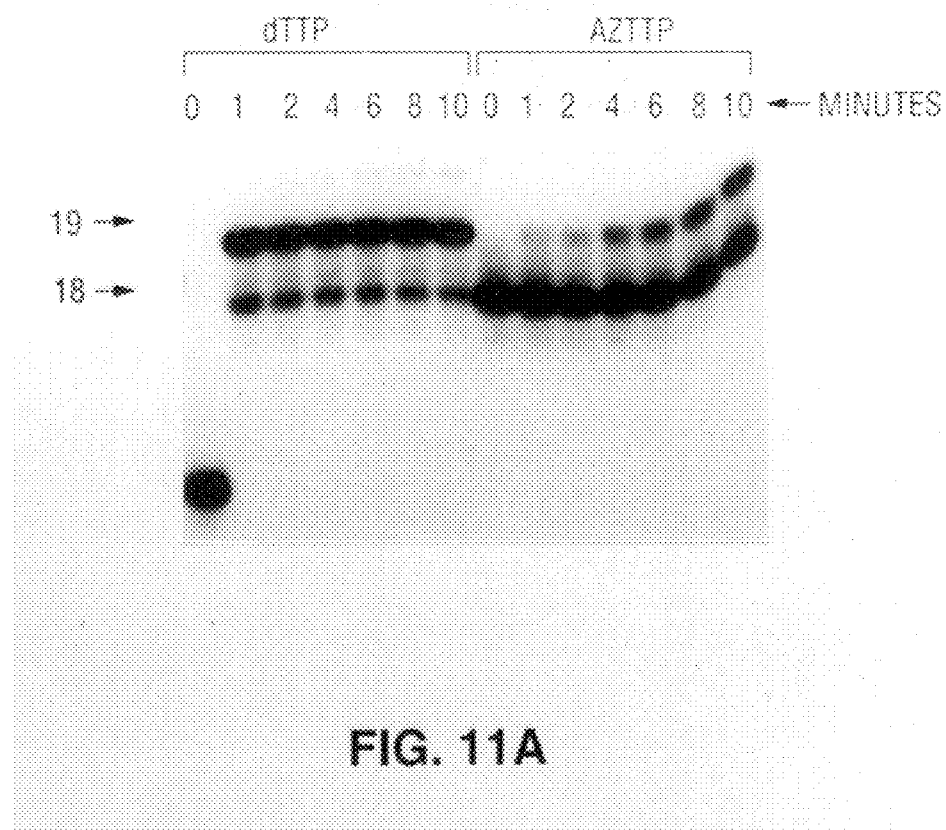
FIG. 11A is an autoradiogram following electrophoresis of "standing start" primer-templates used to test for the incorporation of either dTTP or AZTTP.

These primer-templates were used to test for the incorporation of either dTTP or AZTTP at the site complementary to the outlined "A". The standing start primer-template (SEQ ID NO:27,29) was extended by the 0.07 units recombinant polymerase α using either dTTP or AZTTP over a time course from 0 to 10 minutes. Following the reaction, the samples were subjected to denaturing gel electrophoresis and autoradiography. Incorporation by either dTTP or AZTTP extends the original primer length of 18 bases to 19 bases (see arrows in FIG. 11A).

Figure 11B:
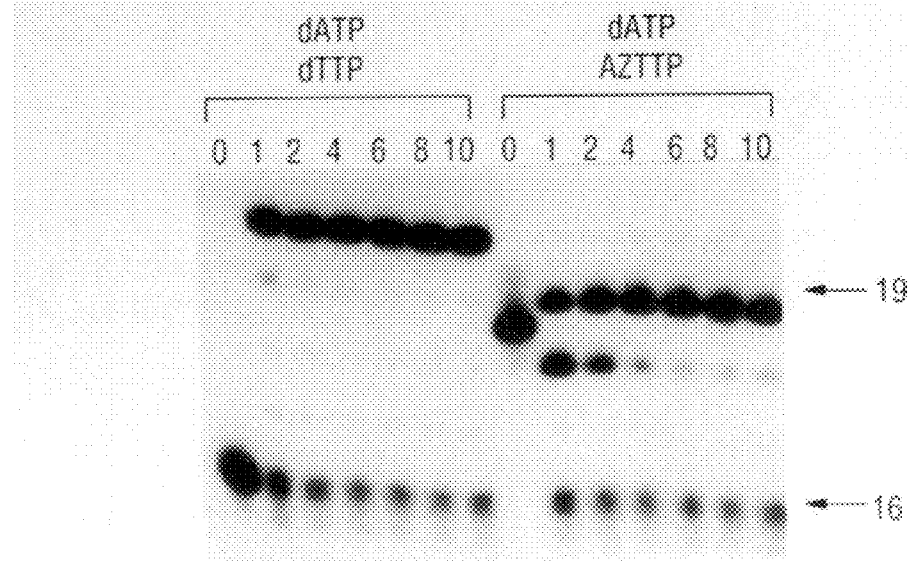
FIG. 11B is an autoradiogram following electrophoresis of "running start" primer-templates used to test for the incorporation of either dTTP or AZTTP.

Similarly, the running start primer-template (SEQ ID NO:27) was extended by the 0.09 units recombinant polymerase α in the presence of dATP and either dTTP or AZTTP over a time course from 0 to 10 minutes. Incorporation by AZTTP extends the original primer length of 16 bases to 19 bases (see arrows in FIG. 11B).

The data of FIG. 11 indicates that the recombinant human DNA polymerase α of the present invention is useful as a reagent for screening analogs. This finding that the anti-viral agent AZT is incorporated by the human replication machinery is predictive of mutations in humans.

VI. DRUG DESIGN

The previous section illustrates how the present invention is particularly useful for screening chemotherapeutics for potential mutagenicity and carcinogenicity. It is also contemplated, however, that the present invention be used to design drugs, including drugs with polymerase inactivation properties.

For example, while AZT appears to be the drug of choice at this time for treating AIDS, some results indicate that AZT exhibits toxicity in a clinical setting (in addition to its potential mutagenicity shown by the data described above). Clearly, there remains a strong need for new antiviral agents, especially those with low toxicity to normal cells.

Intensive efforts to develop therapies which can prevent or block the development of serious clinical symptoms in AIDS patients are under way. For the most part, these efforts have focused on the use of nucleotide analogue drugs which inhibit reverse transcriptase. See e.g., U.S. Pat. No. 4,916,122 by Chu et al., hereby incorporated by reference. The goal is to find drugs which are more selective and demonstrate greater specificity.

Traditionally, the search for new drugs capable of interacting with a particular biomolecule, such as a retroviral enzyme, has been somewhat random. The polymerase of the present invention, by contrast, allows for drug design using the knowledge of specific characteristics of the biomolecule as a starting point.

One specific characteristic of the human polymerase α catalytic polypeptide that has heretofore not been known is its detailed structure. This is because, prior to this invention, sufficient amounts of pure polymerase have not been available. By virtue of the present invention, sufficient amounts of the catalytic polypeptide are present to perform analytical work, including x-ray crystallography.

The design of compounds that interact preferentially with, for example, a viral polymerase and not with the polymerase of the present invention can be developed using computer analysis of the three-dimensional structures. Using a set of coordinates for each enzyme, a computer program, and a compound database, putative specific-binding compounds can be identified based on a simple function of interatomic distances.

The interatomic distances can themselves be previously determined by a number of methods known in the art. For example, two-dimensional homonuclear correlated spectroscopy (COSY) generally is the first 2D experiment to be used in analyzing a protein. For those skilled in the art with one-dimensional NMR spectroscopy, COSY provides the kind of information available from a single-frequency decoupling experiment, e.g., which spins are scaler coupled to one another. In a COSY plot, the 1D spectrum lies along the diagonal, and the off-diagonal elements are present at the intersection of chemical shifts of groups that are J coupled. The "fingerprint" region contains ($^{1}H^{N}$, $^{1}H^{\alpha}$) cross-peaks from the peptide backbone. The degree of resolution of the "fingerprint" region of a COSY map obtained in $H_2O$ is a good predictor of the success of sequence-specific assignments to be obtained without recourse to isotopic labeling.

Transferred nuclear Overhauser effect (TRNOE) spectra ($^{1}H$ NMR) relies on different 2D NOE spectra, and, in essence, looks at the conformation of the ligand just after it has dissociated from the protein. The use of TRNOE presumes, however, that the bound and free ligands are in fast exchange on the chemical shift time scale which translates to a ligand $K_D$ greater than or equal to about $10^{-4}$ M. TRNOE methods are useful to cross-check and augment the distance information obtained by other approaches.

It is not intended that the present invention be limited by the particular method used to obtain structural information. Furthermore, it is not intended that the present invention be limited to a search for any one type of drug; one or more of the molecules may be naturally occurring or may be synthetic. If synthetic, they may be, for example, drug-receptor complexes. If naturally occurring they may or may not be biomolecules ("biomolecules" are herein defined as molecules found in a living organism). If biomolecules, they may be, for example, enzyme-substrate or enzyme-inhibitor complexes.

Finally, it is not intended that the drug design always involve a comparison with another polymerase. For example, it may be desired that nucleic acid binding drugs be developed. In such a case, a predictive analysis of the potential impact on the polymerase of the present invention may rely on structural information concerning the polymerase-DNA complex. Such data can be obtained in may ways. For example, De Jong et al. studied the interaction of *E. coli* phage DNA binding protein with single-stranded DNA. E. A. M. De Jong et al., J. Mag. Res. 80:197 (1988). The technique utilized spin-labeled oligonucleotides; the dipolar interaction between the free electron spin of the spin-label on the substrate causes an increase in the relaxation rate of nearby protons. Spin labels such as TEMPO are good to about 15 angstroms.

VII. VIRAL PROTEIN BINDING

The present invention further contemplates the use of recombinant human DNA polymerase α to test for the binding of viral proteins. In one embodiment, the present invention contemplates co-infection of cells with two expression vectors, one vector coding for the viral protein of interest and the other vector coding for human DNA polymerase α.

As an example of recombinant human DNA polymerase α interaction with viral proteins, the SV40 virus large T antigen was specifically examined. The SV40 virus large T antigen has a wide range of functions, one of which is the ability to transform a permissive cell to the cancerous state. It has already been established that the SV40 large T antigen protein can bind the catalytic subunit of the DNA polymerase α in vitro. See Dornreiter et al. EMBO J. 9:3329 (1990).

To detect this binding in vivo, baculoviruses were constructed that express both the large T antigen and the human DNA polymerase α catalytic subunit of the present invention in insect cells. For this purpose the 941T baculovirus was employed. See R. Lanford Virol. 167:72 (1988). This expresses the SV40 large T antigen.

The baculoviruses 941T and AcHDPα were singly and co-infected into insect Sf9 cells. The cells were incubated for 44 hours, harvested, lysed and proteins immunoprecipitated with either monoclonal antibodies against the human polymerase α catalytic subunit (using monoclonal SJK237-71) or against the large T antigen (using Pab101).

Figures 12A, 12B:
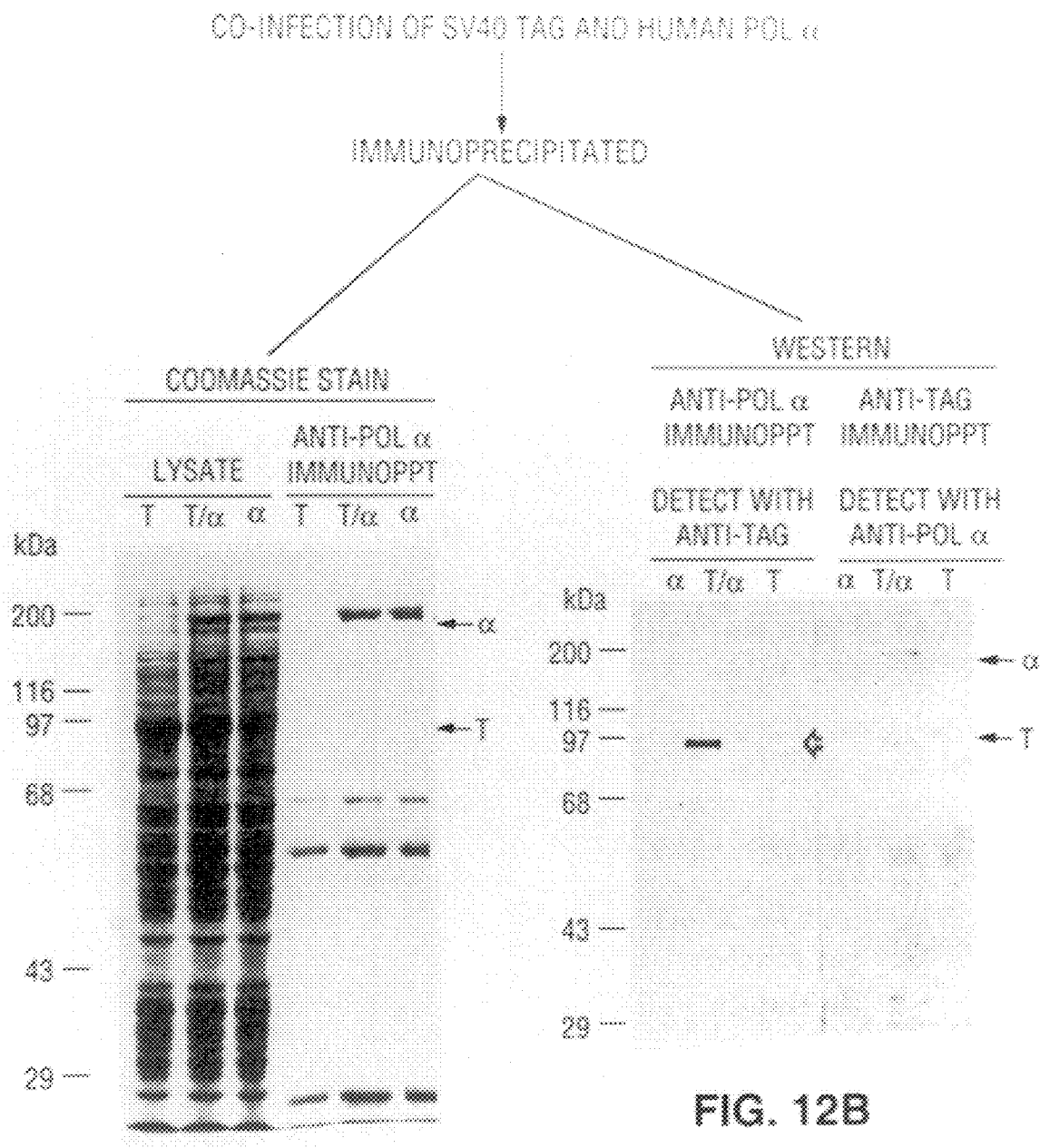
FIG. 12A is a Coomassie Blue stained gel of cell lysates and anti-polymerase α immunoprecipitations.
FIG. 12B is a (Western) immunoblot.

FIG. 12 shows both the strategy and results of such an experiment. FIG. 12A is a Coomassie Blue stained gel of the lysates and anti-Pol α immunoprecipitations. "T" designates the lysate and immunoprecipitation from 941T infected insect cells, "α" from AcHDPα infected cells, and "T/α" from the co-infection insect cells demonstrates the association of a protein with identical mass as that of the SV40 T antigen. This protein was confirmed to be the T antigen by a (Western) immunoblot assay (FIG. 12B). The T antigen associated with Pol α was detected with the anti-T antigen ("anti-Tag") monoclonal, Pab101.

The reverse experiment was also performed (see right hand panel of FIG. 12B). The anti-T antigen monoclonal was used to immunoprecipitate and the anti-polymerase monoclonal was as shown of the right side of the Western blot.

These experiments demonstrate that expression of the human DNA polymerase α in the baculovirus system provides an amendable method to study the interaction of cellular and viral proteins, such as the SV40 T antigen, with the polymerase α catalytic subunit.

It is not intended that the present invention be limited to a particular viral protein. In particular, this binding approach is in no way limited to SV40 T antigen. This approach may be extended to other viral proteins.

By way of a further example, the present invention contemplates binding to papillomaviruse proteins. The papillomaviruses are small DNA viruses that induce benign proliferative squamous epithelial and fibroepithelial lesions in their natural hosts. The Bovine papillomavirus type 1 (BPV-1) has served as the prototype for the genetic analysis of the papillomavirus functions. Transformation of rodent cells by BPV-1 has enabled functions important for viral transformation, replication, and transcription regulation to be mapped.

Such studies have revealed that products encoded by the BPV-1 E5 and E6 genes are required for full transformation, E1 products are necessary for viral DNA replication, and E2 polypeptides function both in replication and transcription regulation. To understand BPV-1 replication, Botchan and co-workers have developed an in vitro replication assay. See L. Yang, et al., Nature, in press, (1991). This assay involves adding purified BPV-1 E1 and E2 proteins, a DNA plasmid containing the BPV-1 origin of replication, and radiolabeled nucleotides to murine or human cell extracts and assaying for replication of the plasmid.

The present invention contemplates involvement of the DNA polymerase α complex. Demonstration of this involvement in replication is achieved using the neutralizing antibody SJK-132–20. SJK-132-20 was able to abolish in vitro BPV-1 replication while the non-neutralizing antibody, SJK237-71, had no affect on this replication. This experiment suggests that either E1 or E2 or the E1/E2 complex is able to bind and sequester the DNA polymerase α complex at the BPV-1 origin of replication. In this manner, the polymerase of the present invention is useful to map the interaction of the BPV-1 E1 and/or E2 proteins.

From the above it is evident that the present invention provides polymerase α that is functional, and yet free of contaminating protein typically associated with human DNA polymerase α purified by traditional biochemical isolation techniques. This reagent is useful for, aomg other things, the screening of chemotherapeutics for mutagenicity, particularly where mutations are caused by the incorporation of analogs of the normal nucleotide bases during DNA replication.

What is claimed is:

1. A screening method for determining the mutagenicity of chemotherapeutic agents, comprising:
   a) providing an isolated human DNA polymerase α catalytic polypeptide, wherein said polymerase comprises the amino acid sequence shown in FIG. 3;
   b) providing a chemotherapeutic agent suspected of having mutagenic activity;
   c) providing a nucleic acid template for replication; and
   d) combining said polymerase, said chemotherapeutic agent, and said nucleic acid template under reaction conditions such that, in the absence of said chemotherapeutic agent, said template is replicated.

2. The screening method of claim 1, wherein said chemotherapeutic agents are analogs of a normal nucleotide base.

3. The screening method of claim 2, wherein said analog is incorporated into a polynucleotide during replication of said nucleic acid template.

4. The screening method of claim 3, further comprising the step of measuring the amount of said analog incorporated into said polynucleotide.

* * * * *